United States Patent
Converso et al.

(10) Patent No.: US 11,648,250 B2
(45) Date of Patent: May 16, 2023

(54) TETRAHYDROQUINAZOLINE DERIVATIVES AS SELECTIVE CYTOTOXIC AGENTS

(71) Applicant: Merck Sharp & Dohme LLC, Rahway, NJ (US)

(72) Inventors: Antonella Converso, Elkins Park, PA (US); Abdellatif El Marrouni, Ambler, PA (US); Anthony W. Shaw, Harleysville, PA (US); David N. Hunter, Hatfield, PA (US); Ashley Forster, Gilbertsville, PA (US); Cheng Wang, Fort Washington, PA (US); Yunlong Zhang, Valhalla, NY (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 23 days.

(21) Appl. No.: 17/411,341

(22) Filed: Aug. 25, 2021

(65) Prior Publication Data

US 2022/0062284 A1 Mar. 3, 2022

Related U.S. Application Data

(60) Provisional application No. 63/223,748, filed on Jul. 20, 2021, provisional application No. 63/071,024, filed on Aug. 27, 2020.

(51) Int. Cl.
| | | |
|---|---|---|
| *A61K 31/513* | (2006.01) | |
| *A61P 31/18* | (2006.01) | |
| *A61K 45/06* | (2006.01) | |
| *C07D 401/06* | (2006.01) | |
| *C07D 403/06* | (2006.01) | |

(52) U.S. Cl.
CPC ............ *A61K 31/513* (2013.01); *A61K 45/06* (2013.01); *A61P 31/18* (2018.01); *C07D 401/06* (2013.01); *C07D 403/06* (2013.01)

(58) Field of Classification Search
None
See application file for complete search history.

(56) References Cited

U.S. PATENT DOCUMENTS

| | | |
|---|---|---|
| 6,124,302 A | 9/2000 | Corbett et al. |
| 6,127,375 A | 10/2000 | Corbett |

OTHER PUBLICATIONS

Ait-Ammar, et al, Current Status of Latency Reversing Agents Facing the Heterogeneity of HIV-1 Cellular and Tissue Reservoirs, Frontiers in Microbiology, 2020, 3060 1-23, 10.
Dinoso, J.B. et al., Treatment intensification does not reduce residual HIV-1 viremia in patients on highly active antiretroviral therapy, PNAS, 2009, 9403-9408, 106(23).
Figueiredo, A. et al., Potent Nonnucleoside Reverse Transcriptase Inhibitors Target HIV-1 Gag-Pol, PLoS Pathogens, 2006, 1051-1059, 2(11): e119.
Jochmans, Dirk et al., Selective killing of human immunodeficiency virus infected cells by non-nucleoside reverse transcriptase inhibitor-induced activation of HIV protease, Retrovirology, 2010, 1-14, 7:89.
Singh, et al, Latency Reversal 2.0: Giving the Immune System a Seat at the Table, Current HIV/AIDS Reports, 2021, 117-127, 18.
Sudo, Sho et al., Efavirenz Enhances HIV-1 Gag Processing at the Plasma Membrane through Gag-Pol Dimerization, Journal of Virology, 2013, 3348-3360, 87(6).
Tachedjian, Gilda et al., Efavirenz enhances the proteolytic processing of an HIV-1 pol polyprotein precursor and reverse transcriptase homodimer formation, FEBS Letters, 2005, 379-384, 579.
Tachedjian, Gilda et al., Nonnucleoside reverse transcriptase inhibitors are chemical enhancers of dimerization of the HIV type 1 reverse transcriptase, PNAS, 2001, 7188-7193, 98(13).
Van Der Sluis, Combination Immune Checkpoint Blockade to Reverse HIV Latency, Journal of Immunology, 2020, 1242-1254, 204.
Zerbato, Jennifer et al., Nonnucleoside Reverse Transcriptase Inhibitors Reduce HIV-1 Production from latently Infected Resting CD4 + T Cells following latency Reversal, Antimicrobial Agents and Chemotherapy, 2017, 1-5, 61(3).

*Primary Examiner* — Jeffrey S Lundgren
*Assistant Examiner* — Michael J Schmitt
(74) *Attorney, Agent, or Firm* — Patricia A. Shatynski; John C. Todaro

(57) ABSTRACT

The present disclosure is directed to tetrahydroquinazoline derivatives of Formula I

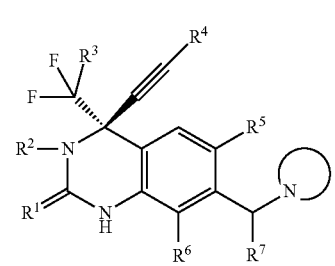

and their use for selectively killing HIV infected GAG-POL expressing cells without concomitant cytotoxicity to HIV naïve cells, and for the treatment or prophylaxis of infection by HIV, or for the treatment, prophylaxis or delay in the onset or progression of AIDS or AIDS Related Complex (ARC).

30 Claims, No Drawings

TETRAHYDROQUINAZOLINE DERIVATIVES AS SELECTIVE CYTOTOXIC AGENTS

BACKGROUND OF THE INVENTION

Human immunodeficiency virus (HIV) is the causative agent of acquired immunodeficiency syndrome (AIDS). In the absence of viral suppression, people living with HIV exhibit severe immunodeficiency which makes them highly susceptible to debilitating and ultimately fatal opportunistic infections. Multiple clinically approved antiretroviral drugs are available which demonstrate multi-log reductions in viral loads. Treated patients are at risk for acquiring mutations which render the virus in their bodies resistant to available therapies and rapid rebound of viremia is seen when therapy is removed, indicating that current regimens are not curative.

HIV is a retrovirus whose life cycle involves reverse transcription of a viral RNA genome into DNA via an enzyme known as reverse transcriptase and subsequent integration of the DNA copy into the host chromosomal DNA via the virally encoded integrase. Viral RNA is transcribed and viral proteins are translated using the host cellular machinery in conjunction with viral accessory proteins. Many viral proteins are contained within the GAG and GAG-POL polyproteins, with GAG containing structural proteins and GAG-POL resulting from a frameshift near the carboxy-terminus of GAG and containing protease (PR), reverse transcriptase (RT), and integrase (IN) viral enzymes, in addition to the structural proteins. GAG and GAG-POL are cleaved into individual proteins through the process of maturation which occurs during budding of virions from the infected cell. At this time GAG-POL dimerizes and the now dimeric HIV PR within the GAG-POL dimer forms an active enzyme which can cleave itself out of the polyprotein and catalyze further cleavage to form the remaining viral enzymes and structural proteins.

Available antiretroviral drugs act by blocking the virus at different stages in the viral life cycle. For example, reverse transcriptase inhibitors target the viral reverse transcriptase and prevent the RNA genome from being copied into DNA, integrase inhibitors block the ability of the copied DNA from being integrated into the host cell, and protease inhibitors prevent viral maturation so that virions produced from cells treated with protease inhibitors are immature and non-infectious. Once integration has occurred, a cell is infected until it dies through either normal cell death pathways, accelerated death due to viral factors, or is targeted by the immune system. While most infected cells are expected to die within ~2 days of being infected, the rapid rebound of viremia when therapy is removed is an indication that infected cells remain even after years on therapy (See, e.g., J. B. Dinoso et al., Proc. Natl. Acad. Sci. U.S.A., 2009, 106(23): 9403-9408). These latently infected and/or persistently virus-expressing cells that remain even during antiretroviral therapy are collectively termed the HIV reservoir and are the reason that people living with HIV require life-long treatment with a high level of adherence to maintain virus at undetectable levels. Thus, new therapies that can selectively kill the HIV infected cells would provide new treatment options for HIV infection. Treatment with compounds that can accelerate death of HIV infected cells and decrease the overall number of virally infected cells that persist within patients has the potential to decrease residual viremia in HIV suppressed individuals and address co-morbidities associated with chronic viral infection such as chronic inflammation, immune dysfunction, accelerated aging, cardiovascular disease (CVD), central nervous system (CNS) and other tissue and end-organ damage. Furthermore, treatment with compounds that can purge the remaining HIV reservoir may prolong viral remission off therapy and play a role in an HIV cure strategy.

SUMMARY OF THE INVENTION

The present disclosure is directed to tetrahydroquinazoline derivatives and their use as HIV-Targeted Activator of Cell Kill agents which accelerate the death of HIV GAG-POL expressing cells without concomitant cytotoxicity to HIV naïve cells. Accordingly, the compounds disclosed herein are useful for the treatment or prophylaxis of infection by HIV, or for the treatment, prophylaxis or delay in the onset or progression of AIDS or AIDS Related Complex (ARC). Additionally, the compounds are useful for selectively killing HIV infected, GAG-POL expressing cells in a subject infected with HIV. Compositions and methods of use comprising the compounds of this disclosure are also provided.

DETAILED DESCRIPTION OF THE INVENTION

The present disclosure is directed to tetrahydroquinazoline derivative compounds and their use for accelerating the death of HIV GAG-POL expressing cells without concomitant cytotoxicity to HIV naïve cells. In the absence of compounds such as those from the present invention, protease (PR) activation takes place during viral maturation and the concentration of mature PR in the cytoplasm is limited. In contrast, the present compounds promote the desired phenotype by catalyzing GAG-POL dimerization inside the infected cell by binding to the immature RT binding site and triggering premature activation of the HIV PR enzyme inside the host infected cell prior to budding. As a result, PR cleaves host substrates within the cell, leading to cytotoxicity and cell death. This effect can be blocked in the presence of an HIV protease inhibitor such as indinavir or darunavir demonstrating the role of HIV protease in the process.

The compounds presently disclosed herein also have activity as Non-Nucleoside Reverse Transcriptase Inhibitors (NNRTIs), due to the homology between the mature and immature RT pocket in HIV that allows the compounds to bind to the mature hydrophobic pocket near the active site of the viral RT enzyme. Binding to mature RT results in inhibition of enzymatic activity and production of the DNA provirus, which prevents infection of naïve CD4+ T-cells.

While effects of NNRTIs on dimerization of RT and GAG-POL have been documented (Tachedjian et al. Proc. Natl. Acad. Sci. U.S.A. 2001, 98(13):7188; Tachedjian et al. FEBS Lett. 2005, 579:379; Figueiredo et al. PLOS Path. 2006, 2(11):1051; Sudo et al. J. Virol. 2013, 87(6):3348), selective killing of HIV infected cells as a result of enhanced dimerization was first reported by Jochmans et al. (Jochmans et al. Retrovirology 2010, 7:89). The authors generated data showing these effects in chronically infected MT-4 cells, PBMCs, and CD4+ cells. Based on the potencies of tested molecules they concluded that "These data present proof of concept for targeted drug induced elimination of HIV producing cells. While NNRTIs themselves may not be sufficiently potent for therapeutic application, the results provide a basis for the development of drugs exploiting this mechanism of action." More recently, Zerbato et al. (Zerbato et al. Antimicrob. Agents Chemother. 2017, 61(3)) measured the activity of NNRTIs in a primary cell model for HIV latency. They saw significant reduction in virus production for certain NNRTIs compared to other classes of antiretrovirals and inferred that this was due to these compounds' ability to eliminate cells expressing HIV GAG-POL proteins. More recently, in their paper Trinité et al. (Trinité et al., Retrovirology, 2019, 16(17)) stated that NNRTI-induced PR-activation triggers apoptotic cell death of productively HIV-infected resting or activated T-cells.

The present disclosure is directed to a compound of Formula I

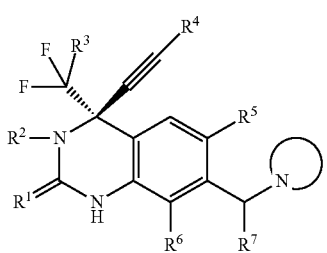

I or a pharmaceutically acceptable salt thereof, wherein:
$R^1$ is O or S;
$R^2$ is —H or —$C_{1-8}$alkyl unsubstituted or substituted with 1 to 17 of F;
$R^3$ is halo or —$C_{1-8}$alkyl;
$R^4$ is —$C_{1-8}$alkyl or $C_{3-6}$cycloalkyl;
$R^5$ is —H, halo, —CN, —$C_{1-8}$alkyl, —$C_{2-8}$alkenyl, —C(O)O$C_{1-8}$alkyl, —C(O)$C_{1-8}$alkyl or —C(O)NR$^8$R$^9$;
$R^6$ is —H or halo;
$R^7$ is —H or halo;

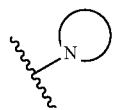

represents a 6-membered heterocyclic ring attached by a nitrogen atom in said ring to the carbon atom in —C(R$^7$)—, wherein the 6-membered heterocyclic ring is selected from pyridinone, pyrimidinone, pyrimidin-dione, pyrazinone, pyrazin-dione and pyridazinone, wherein each ring is unsubstituted or substituted with one or more substituents up to the maximum number allowed by valence, independently selected at each occurrence from:
(i) halo, (ii) —NR$^8$R$^9$, (iii) —CN,
(iv) —$C_{1-8}$alkyl unsubstituted or substituted with 1 to 8 substituents independently selected at each occurrence from —OH and halo (e.g., F, Cl or Br);
(v) —$C_{1-4}$alkyl-O—$C_{1-4}$alkyl unsubstituted or substituted with 1 to 8 substituents independently selected at each occurrence from —OH or halo (e.g., F, Cl or Br), and
(vi) —$C_{3-6}$cycloalkyl unsubstituted or substituted with 2 to 5 substituents independently selected at each occurrence from —OH or halo, and
(vii) —O$C_{1-8}$alkyl unsubstituted or substituted with 1 to 8 substituents independently selected at each occurrence from —OH and halo;
$R^8$ is —H or —$C_{1-8}$alkyl unsubstituted or substituted with 1 to 8 substituents independently selected at each occurrence from —OH and halo; and $R^9$ is —H or —$C_{1-8}$alkyl unsubstituted or substituted with 1 to 8 substituents independently selected at each occurrence from —OH and halo.

In Embodiment 1 of this disclosure are compounds of Formula I, or pharmaceutically acceptable salts thereof, wherein $R^2$ is —H or —$C_{1-6}$alkyl unsubstituted or substituted with 1 to 13 of F; or in a class thereof $R^2$ is —H or —$C_{1-3}$alkyl unsubstituted or substituted with 1 to 7 of F; or in a further class thereof $R^2$ is —H, —$CH_3$ or —$CH_2CH_3$.

In Embodiment 2 of this disclosure are compounds of Formula I or Embodiment 1, and each class thereof, or pharmaceutically acceptable salts of the foregoing, wherein $R^3$ is halo or —$C_{1-6}$alkyl; or in a class thereof $R^3$ is F, Cl, Br or $C_{1-3}$alkyl; or in a further class thereof $R^3$ is F or —$CH_3$.

In Embodiment 3 of this disclosure are compounds of Formula I, Embodiment 1 or Embodiment 2, and each class thereof, or pharmaceutically acceptable salts of the foregoing, wherein $R^4$ is —$C_{1-6}$alkyl or —$C_{3-6}$cycloalkyl; or in a class thereof $R^4$ is —$C_{1-4}$alkyl or $C_{3-5}$cycloalkyl; or in a further class thereof $R^4$ is cyclopropyl or —$C_{1-4}$alkyl.

In Embodiment 4 of this disclosure are compounds of Formula I, Embodiment 1, Embodiment 2 or Embodiment 3, and each class thereof, or pharmaceutically acceptable salts of the foregoing, wherein $R^5$ is —H, halo, —CN, —$C_{1-6}$alkyl, —$C_{2-6}$alkenyl, —C(O)O—$C_{1-6}$alkyl, —C(O)—$C_{1-6}$alkyl, or —C(O)NR$^8$R$^9$. In a class thereof $R^5$ is —H, F, Cl, Br, —CN, or —$C_{1-3}$alkyl, —C(O)O—$C_{1-3}$alkyl, —C(O)—$C_{1-3}$alkyl, or —C(O)NR$^8$R$^9$; or in a further class thereof $R^5$ is —H, F, Cl, Br or —$CH_3$.

In Embodiment 5 of this disclosure are compounds of Formula I, Embodiment 1, Embodiment 2, Embodiment 3 or Embodiment 4, and each class thereof, or pharmaceutically acceptable salts of the foregoing, wherein $R^6$ is —H, F, Cl or Br; or in a class thereof $R^6$ is —H or F.

In Embodiment 6 of this disclosure are compounds of Formula I, Embodiment 1, Embodiment 2, Embodiment 3, Embodiment 4 or Embodiment 5, and each class thereof, or pharmaceutically acceptable salts of the foregoing, wherein $R^7$ is —H, F, Cl or Br; or in a class thereof $R^7$ is —H or F.

In Embodiment 7 of this disclosure are compounds of Formula I, Embodiment 1, Embodiment 2, Embodiment 3, Embodiment 4, Embodiment 5 or Embodiment 6, and each class thereof, or pharmaceutically acceptable salts of the foregoing, wherein $R^8$ and $R^9$ are each independently selected from (i) —H or —$C_{1-6}$alkyl unsubstituted or substituted with 1 to 6 substituents independently selected at each occurrence from —OH and halo; or (ii) —H and —$C_{1-3}$alkyl unsubstituted or substituted with 1 to 3 substituents independently selected at each occurrence from —OH and halo; or (iii) —H and $CH_3$. In a further class of this Embodiment, halo is F or Cl.

In Embodiment 8 of this disclosure are compounds of Formula I, Embodiment 1, Embodiment 2, Embodiment 3, Embodiment 4, Embodiment 5, Embodiment 6, or Embodiment 7, and each class thereof, or pharmaceutically acceptable salts of the foregoing, wherein $R^1$ is O.

In Embodiment 9 of this disclosure are compounds of Formula I, Embodiment 1, Embodiment 2, Embodiment 3, Embodiment 4, Embodiment 5, Embodiment 6, or Embodiment 7, and each class thereof, or pharmaceutically acceptable salts of the foregoing, wherein Riis S.

In Embodiment 10 of this disclosure are compounds of Formula I, Embodiment 1, Embodiment 2, Embodiment 3, Embodiment 4, Embodiment 5, Embodiment 6, Embodiment 7, Embodiment 8 or Embodiment 9, and each class thereof, or pharmaceutically acceptable salts of the foregoing, wherein:

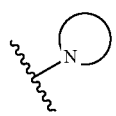

is selected from:

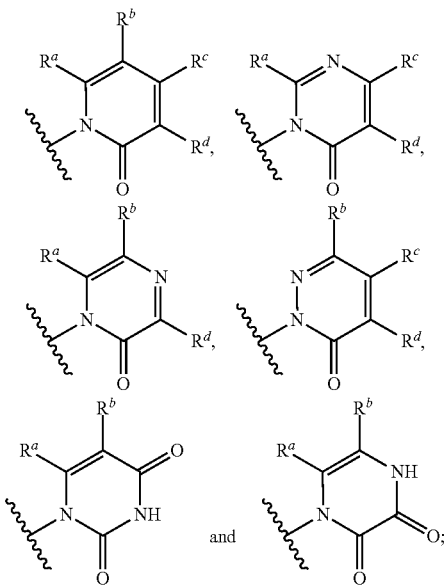

$R^a$ is (i) —H or (ii) —$C_{1-6}$alkyl, e.g., —$C_{1-3}$alkyl or —$CH_3$;
$R^b$ is (i) —H, (ii) halo, e.g., —F or —Cl, (iii) —$C_{1-6}$alkyl, e.g., —$C_{1-3}$alkyl or —$CH_3$; or (iv) —$OC_{1-6}$alkyl, e.g., —$OC_{1-3}$alkyl or —$OCH_3$;
$R^c$ is (i) —H, (ii) halo, e.g., —F or —Cl, (iii) —$NR^8R^9$, e.g., —$NH_2$, (iv) —CN, (v) —$C_{1-6}$alkyl, e.g., —$C_{1-3}$alkyl or —$CH_3$, unsubstituted or substituted with —OH, (vi) —$C_{1-6}$alkyl substituted with 1 to 13 of F, e.g., —$CF_3$, —$CH_2F$, —$CHF_2$, —$CF_2CH_3$, —CH(F)—$CF_3$, or —$CH_2CF_3$, (vii) —$OC_{1-6}$alkyl, e.g. —$OC_{1-3}$alkyl or —$OCH_3$, (viii) —$C_{1-3}$alkyl-O—$C_{1-3}$alkyl, e.g., —$CH_2$—O—$CH_3$, (ix) —$C_{3-6}$cycloalkyl, e.g., cyclopropyl, (x) —C(O)$OR^8$, (xi) —$CONR^8R^9$, or (xii) —$COR^8$; and
$R^d$ is (i) —H, (ii) —CN, (iii) halo, e.g., —F or —Cl, (iv) —$NR^8R^9$, e.g., —$NH_2$, (v) —$C_{1-6}$alkyl, e.g., —$C_{1-3}$alkyl or —$CH_3$, unsubstituted or substituted with —OH, or (vi) —$OC_{1-6}$alkyl, e.g., —$OC_{1-3}$alkyl or —$OCH_3$.

In another Embodiment of this disclosure is a compound of Formula I, or pharmaceutically acceptable salts thereof, having the following Formula II:

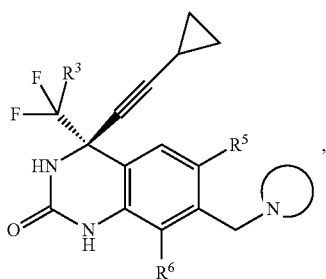

II or a pharmaceutically acceptable salt thereof, wherein $R^3$, $R^5$, $R^6$ and

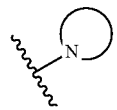

are defined as in Formula I.

In Embodiment 11 of this disclosure are compounds of Formula II, or pharmaceutically acceptable salts thereof, wherein $R^3$ is halo or —$C_{1-6}$alkyl; or in a class thereof $R^3$ is F, Cl, Br or $C_{1-3}$alkyl; or in a further class thereof $R^3$ is —F or —$CH_3$.

In Embodiment 12 of this disclosure are compounds of Formula II or Embodiment 11, and each class thereof, or pharmaceutically acceptable salts of the foregoing, wherein $R^5$ is —H, halo, —CN, —$C_{1-6}$alkyl or —$C_{2-6}$alkenyl; or in a class thereof $R^5$ is —H, F, Cl, Br, —CN, or —$C_{1-3}$alkyl; or in a further class thereof $R^5$ is —H, F, Cl, Br, —CN or —$CH_3$.

In Embodiment 13 of this disclosure are compounds of Formula II, Embodiment 11 or Embodiment 12, and each class thereof, or pharmaceutically acceptable salts of the foregoing, wherein $R^6$ is —H, F, Cl or Br; or in a class thereof $R^6$ is —H or F.

In Embodiment 14 of this disclosure are compounds of Formula II, Embodiment 11, Embodiment 12, Embodiment 13, and each class thereof, or pharmaceutically acceptable salts of the foregoing, wherein:

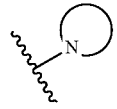

is selected from:

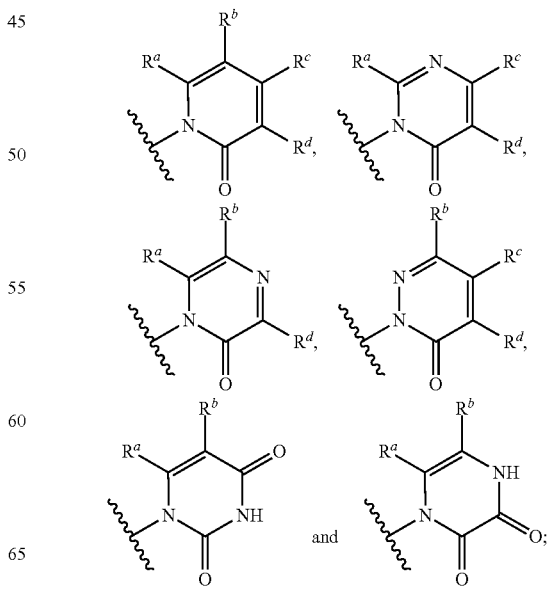

$R^a$ is (i) —H or (ii) —$C_{1-6}$alkyl, e.g., —$C_{1-3}$alkyl or —$CH_3$;

$R^b$ is (i) —H, (ii) halo, e.g., —F or —Cl, (iii) —$C_{1-6}$alkyl, e.g., —$C_{1-3}$alkyl or —$CH_3$, or (iv) —$OC_{1-6}$alkyl, e.g. —$OC_{1-3}$alkyl or —$OCH_3$;

$R^c$ is (i) —H, (ii) halo, e.g., —F or —Cl, (iii) —$NR^8R^9$, e.g., —$NH_2$, (iv) —CN, (v) —$C_{1-6}$alkyl, e.g., —$C_{1-3}$alkyl or —$CH_3$, unsubstituted or substituted with —OH, (vi) —$C_{1-6}$alkyl substituted with 1 to 13 of F, e.g., —$CF_3$, —$CH_2F$, —$CHF_2$, —$CF_2CH_3$, —$CH(F)$—$CF_3$, or —$CH_2CF_3$, (vii) —$OC_{1-6}$alkyl, e.g. —$OC_{1-3}$alkyl or —$OCH_3$, (viii) —$C_{1-3}$alkyl-O—$C_{1-3}$alkyl, e.g., —$CH_2$—O—$CH_3$, (ix) —$C_{3-6}$cycloalkyl, e.g., cyclopropyl, (x) —$C(O)OR^8$, (xi) —$CONR^8R^9$, or (xii) —$COR^8$; and $R^d$ is (i) —H, (ii) —CN, (iii) halo, e.g., —F or —Cl, (iv) —$NR^8R^9$, e.g., —$NH_2$, (v) —$C_{1-6}$alkyl, e.g., —$C_{1-3}$alkyl or —$CH_3$, unsubstituted or substituted with —OH, or (vi) —$OC_{1-6}$alkyl, e.g., —$OC_{1-3}$alkyl or —$OCH_3$.

In Embodiment 15 of this disclosure are compounds of Formula I and each class thereof, or pharmaceutically acceptable salts of the foregoing, wherein: $R^2$ is —H or —$C_{1-3}$ alkyl; $R^3$ is —F or —$CH_3$; $R^4$ is cyclopropyl or —$C_{1-6}$ alkyl; $R^5$ is —H, halo, —CN or —$CH_3$; $R^6$ is —H or halo; and $R^7$ is —H. In Embodiment 15A of this disclosure are compounds of Formula II and each class thereof, or pharmaceutically acceptable salts of the foregoing, wherein: $R^3$ is —F or —$CH_3$; $R^5$ is —H, halo, —CN or —$CH_3$; and $R^6$ is —H or halo.

In Embodiment 16 of this disclosure are compounds of Formula I, Formula II, or each of Embodiments 1, 2, 3, 4, 5, 6, 7, 8, 9, 10, 11, 12, 13, 14 or 15, and each class thereof, or pharmaceutically acceptable salts of the foregoing, wherein:

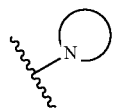

is selected from:

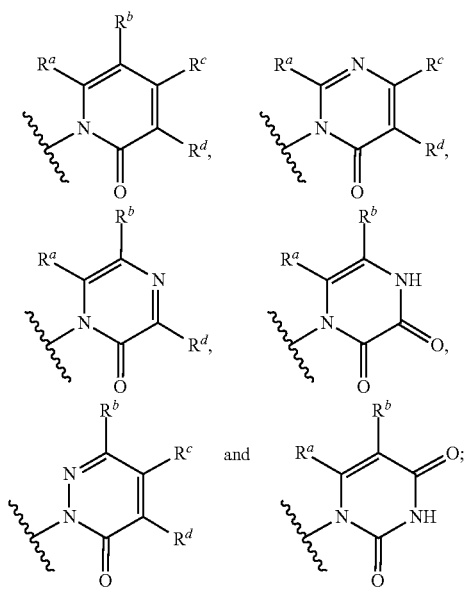

$R^a$ is —H or —$CH_3$;

$R^b$ is —H, —$CH_3$, —$OCH_3$ or halo;

$R^c$ is (i) —H, (ii) halo, (iii) —$NH_2$, (iv) —CN, (v) —$CH_3$ unsubstituted or substituted with —OH, (vi) —$CH_2$—O—$CH_3$, (vii) cyclopropyl, (viii) —$C_{1-3}$alkyl substituted with 1 to 7 of —F, e.g., —$CH_2F$, —$CHF_2$ or —$CF_3$, or (ix) —$OCH_3$; and $R^d$ is (i) —H, (ii) halo, (iii) —$NH_2$, or (iv) —$CH_3$ unsubstituted or substituted with —OH.

The invention is directed to the compounds of Formula I herein and encompasses the compounds of Formula I and II, and all embodiments, examples, classes and sub-classes thereof and includes the compounds of the Examples herein. The invention is further directed to compounds of Formula I which are neutral compounds or salts thereof when such salts are possible, including pharmaceutically acceptable salts.

The term "e.g." means "for example." When the terms "e.g.," or "for example" are used herein, the example(s) recited are intended to be illustrative and are not intended to be an exhaustive list of all relevant examples. The term "i.e." means "that is."

As used herein, "alkyl" refers to both branched- and straight-chain saturated aliphatic hydrocarbon groups having the specified number of carbon atoms in a specified range. For example, "$C_{1-8}$alkyl" refers to each of the alkyl groups having 1, 2, 3, 4, 5, 6, 7, or 8 carbon atoms, including linear or branched isomers thereof. "$C_{1-8}$alkyl" includes the "$C_{1-6}$alkyl" groups and the linear and branched chain alkyls having 7 or 8 carbons in the chain.

The term "$C_{1-6}$alkyl" means each of the linear or branched chain alkyl groups, including all or each of the possible isomers, having 1, 2, 3, 4, 5 or 6 carbon atoms, and includes each of the hexyl and pentyl isomers as well as n-, iso-, sec- and tert-butyl (butyl, i-butyl, s-butyl, t-butyl, collectively "$C_4$alkyl"; Bu=butyl), n- and i-propyl (propyl, i-propyl, collectively "$C_3$alkyl"; Pr=propyl), ethyl (Et) and methyl (Me). "$C_{1-4}$alkyl" has 1, 2, 3 or 4 carbon atoms and includes each of n-, i-, s- and t-butyl, n- and i-propyl, ethyl and methyl. "$C_{1-3}$alkyl" has 1, 2 or 3 carbon atoms and includes each of n-propyl, i-propyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_{2-6}$ alkenyl" refers to all or each of the hexenyl and pentenyl isomers as well as 1-butenyl, 2-butenyl, 3-butenyl, isobutenyl, 1-propenyl, 2-propenyl, and ethenyl (or vinyl). "$C_{2-8}$alkenyl" includes the "$C_{2-6}$ alkenyl" groups plus the linear and branched chain alkenyls having 7 or 8 carbons in the chain.

"Cycloalkyl" refers to a cyclized alkyl ring having the indicated number of carbon atoms in a specified range. Thus, for example, "$C_{3-6}$cycloalkyl" includes each of cyclopropyl, cyclobutyl, cyclopentyl and cyclohexyl, and "$C_{3-4}$cycloalkyl" includes each of cyclopropyl and cyclobutyl.

"Halo" or "halogen" refers to chloro, fluoro, bromo or iodo. Chloro, fluoro and bromo are a class of halogens of interest, and more particularly fluoro and chloro.

"HIV naïve cell(s)" are cells that are not infected with HIV.

"Compatible anti-HIV agent(s)" are anti-HIV agents excluding HIV protease inhibitors.

A "latency reversing agent" (LRA) is a pharmaceutical agent capable of re-activating latent HIV (e.g., HIV-1) in an HIV (e.g., HIV-1) infected cell, particularly in a human.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present disclosure are limited to stable compounds embraced by Formula I and its embodiments. For example, certain moieties as defined in Formula I may be unsubstituted or substituted, and the latter is intended to encompass substitution patterns (i.e., number and kind of substituents) that are chemically possible for the moiety and that result in a stable compound.

This disclosure includes individual diastereomers, particularly epimers, i.e., compounds having the same chemical formula but which differ in the spatial arrangement around a single atom. This disclosure also includes mixtures of diastereomers, particularly mixtures of epimers, in all ratios. This disclosure encompasses compounds of Formula I having either the (R) or (S) stereo-configuration at an asymmetric center and at any additional asymmetric centers that may be present in a compound of Formula I, as well as stereo-isomeric mixtures thereof. Embodiments of this disclosure also include a mixture of enantiomers enriched with 51% or more of one of the enantiomers, including for example 60% or more, 70% or more, 80% or more, or 90% or more of one enantiomer. A single epimer is preferred. An individual or single enantiomer refers to an enantiomer obtained by chiral synthesis and/or using generally known separation and purification techniques, and which may be 100% of one enantiomer or may contain small amounts (e.g., 10% or less) of the opposite enantiomer. Thus, individual enantiomers are a subject of this disclosure in pure form, both as levorotatory and as dextrorotatory antipodes, in the form of racemates and in the form of mixtures of the two enantiomers in all ratios. In the case of a cis/trans isomerism this disclosure includes both the cis form and the trans form as well as mixtures of these forms in all ratios.

The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present disclosure includes all such isomers, as well as salts, solvates (which includes hydrates). and solvated salts of such racemates, enantiomers, diastereomers and tautomers and mixtures thereof.

As would be recognized by one of ordinary skill in the art, certain compounds of the present disclosure may be able to exist as tautomers. All tautomeric forms of such compounds, whether isolated individually or in mixtures, are within the scope of the present disclosure. For example, in instances where an oxo (=O) substituent is permitted on a heterocyclic ring and keto-enol tautomerism is possible, it is understood that the substituent might in fact be present, in whole or in part, in the —OH form. Examples of some tautomers of compounds herein include but are not limited to:

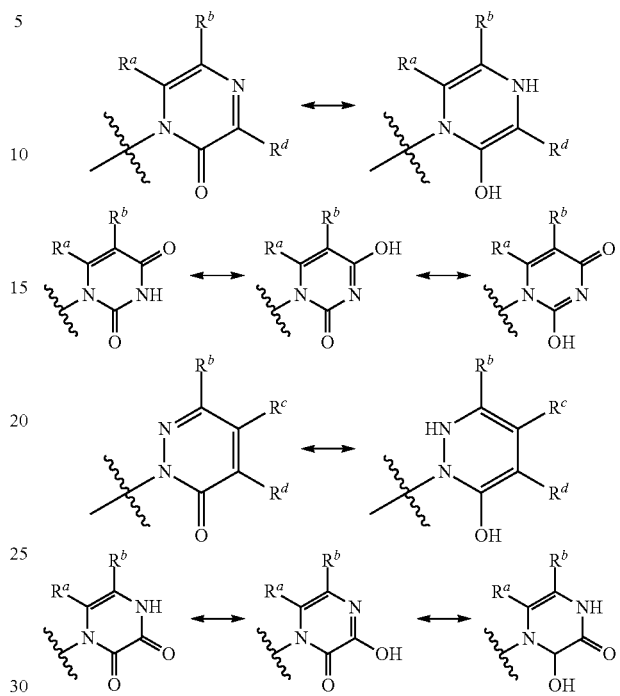

The atoms in a compound of Formula I may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of Formula I; for example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of Formula I can be prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). When the compounds of Formula I contain one or more acidic groups or basic groups, the invention includes the corresponding pharmaceutically acceptable salts.

Thus, the compounds of Formula I that contain acidic groups (e.g., —COOH) can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I, which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

The instant disclosure encompasses any composition comprised of a compound of Formula I or a compound that is a salt thereof, including for example but not limited to, a composition comprised of said compound associated together with one or more additional molecular and/or ionic component(s) which may be referred to as a "co-crystal." The term "co-crystal" as used herein refers to a solid phase (which may or may not be crystalline) wherein two or more different molecular and/or ionic components (generally in a stoichiometric ratio) are held together by non-ionic interactions including but not limited to hydrogen-bonding, dipole-dipole interactions, dipole-quadrupole interactions or dispersion forces (van der Waals). There is no proton transfer between the dissimilar components and the solid phase is neither a simple salt nor a solvate. A discussion of co-crystals can be found, e.g., in S. Aitipamula et al., *Crystal Growth and Design*, 2012, 12 (5), pp. 2147-2152.

Furthermore, compounds of the present disclosure may exist in amorphous form and/or one or more crystalline forms, and as such all amorphous and crystalline forms and mixtures thereof of the compounds of Formula I and salts thereof are intended to be included within the scope of the present disclosure. In addition, some of the compounds of the instant disclosure may form solvates with water (i.e., a hydrate) or common organic solvents. Such solvates and hydrates, particularly the pharmaceutically acceptable solvates and hydrates, of the compounds of this disclosure are likewise encompassed within the scope of the compounds defined by Formula I and the pharmaceutically acceptable salts thereof, along with un-solvated and anhydrous forms of such compounds.

Accordingly, the invention is directed to compounds of Formula I or salts thereof including pharmaceutically acceptable salts thereof, embodiments thereof and specific compounds described and claimed herein, encompass all possible stereoisomers, tautomers, physical forms (e.g., amorphous and crystalline forms), co-crystal forms, solvate and hydrate forms, and any combination of the foregoing forms where such forms are possible.

Another embodiment of the present disclosure is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as, high performance liquid chromatography, and/or mass spectrometry or NMR techniques. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual stereoisomer.

The compounds of Formula I herein, and pharmaceutically acceptable salts thereof, are useful for eliciting GAG-POL dimerization in HIV-infected cells and thereby selectively killing HIV infected GAG-POL expressing cells without concomitant cytotoxicity to HIV naïve cells, referred to herein as TACK (Targeted Activator of Cell Kill) activity, or more specifically HIV TACK activity. HIV TACK or TACK have also been previously referred to as Small Molecule Activated Cell Kill (SMACK). Thus, the compounds of Formula I and pharmaceutically acceptable salts thereof are useful for:

(i) A method for the treatment or prophylaxis of infection by HIV, or for the treatment, prophylaxis, or delay in the onset or progression of AIDS or ARC in a human subject in need thereof which comprises administering to the human subject an effective amount of the compound according to Formula I, or a pharmaceutically acceptable salt thereof; and/or (ii) A method for eliciting GAG-POL dimerization in HIV-infected cells in a human subject in need thereof which comprises administering to the human subject an effective amount of the compound according to Formula I, or a pharmaceutically acceptable salt thereof, and/or (iii) A method for selectively killing HIV infected GAG-POL expressing cells without concomitant cytotoxicity to HIV naïve cells in a human subject which comprises administering to the human subject an effective amount of the compound according to Formula I, or a pharmaceutically acceptable salt thereof; and/or (iv) A method for augmenting the suppression of HIV viremia in a human subject whose viremia is being suppressed by administration of one or more compatible HIV antiviral agents, which comprises additionally administering to the human subject an effective amount of the compound according to Formula I, or a pharmaceutically acceptable salt thereof.

Additionally, the compounds of Formula I and pharmaceutically acceptable salts thereof are useful for any of the methods (i), (ii), (iii) or (iv) above, further comprising administering to the human subject an effective amount of one or more compatible HIV antiviral agents selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents. In the methods of (i), (ii), (iii) or (iv) immediately above, the human subject can be treated with a compound of Formula I or a pharmaceutically acceptable salt thereof in addition to treatment with one or more compatible HIV antiviral agents.

The compounds of Formula I and pharmaceutically acceptable salts thereof are also useful for a method for augmenting the suppression of HIV viremia in a human subject whose viremia is being suppressed by administration of one or more compatible HIV antiviral agents, which comprises additionally administering to the human subject an effective amount of the compound according to Formula I, or a pharmaceutically acceptable salt thereof.

Other embodiments of the present disclosure include the following:

(a) A pharmaceutical composition comprising an effective amount of a compound of Formula I or a pharmaceutically acceptable salt thereof, and a pharmaceutically acceptable carrier.

(b) A pharmaceutical composition which comprises the product prepared by combining (e.g., mixing) an effective amount of a compound of Formula I or a pharmaceutically acceptable salt thereof, and a pharmaceutically acceptable carrier.

(c) The pharmaceutical composition of (a) or (b), further comprising an effective amount of one or more compatible anti-HIV agents selected from the group consisting of HIV antiviral agents, immunomodulators, anti-infective agents and latency reversing agents.

(d) The pharmaceutical composition of (c), wherein the compatible anti-HIV agent is selected from one or more of an antiviral selected from the group consisting of nucleoside or nucleotide HIV reverse transcriptase inhibitors, nucleoside HIV reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

(e) A combination which is (i) a compound of Formula I or a pharmaceutically acceptable salt thereof and (ii) one or more compatible anti-HIV agents selected from the group consisting of HIV antiviral agents, immunomodulators, anti-infective agents and latency reversing agents; wherein the compound and the compatible anti-HIV agent are each employed in an amount that renders the combination effective for the treatment or prophylaxis of infection by HIV, or for the treatment, prophylaxis or delay in the onset or progression of AIDS or ARC.

(f) The combination of (e), wherein the compatible anti-HIV agent is an antiviral selected from the group consisting of nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

(g) A method for eliciting GAG-POL dimerization in HIV-infected cells, a method for selectively killing HIV infected GAG-POL expressing cells without concomitant cytotoxicity to HIV naïve cells, and/or a method for the treatment or prophylaxis of infection by HIV, or for the treatment, prophylaxis, or delay in the onset or progression of AIDS or ARC, comprising administering an effective amount of a compound of Formula I or a pharmaceutically acceptable salt thereof to a subject in need of such treatment.

(h) The method of (g), wherein the compound of Formula I or a pharmaceutically acceptable salt thereof is administered in combination with an effective amount of at least one other compatible HIV antiviral selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

(i) The method of (g) or (h) comprising administering to the subject the pharmaceutical composition of (a), (b), (c) or (d) or the combination of (e) or (f).

(j) Use of a compound of Formula I or a pharmaceutically acceptable salt thereof in the manufacture of a medicament for (1) eliciting GAG-POL dimerization in HIV-infected cells in a subject; (2) selectively killing HIV infected GAG-POL expressing cells without concomitant cytotoxicity to HIV naïve cells in a subject; (3) treatment or prophylaxis of infection by HIV in a subject; (4) treatment, prophylaxis or delay in the onset or progression of AIDS or ARC in a subject; (5) augmenting the suppression of HIV viremia in a subject undergoing treatment with a compatible anti-HIV agent, and/or (6) augmenting the suppression of HIV viremia in a subject whose viremia is being suppressed by administration of one or more compatible HIV antiviral agents.

(k) A compound of Formula I, or a pharmaceutically acceptable salt thereof, for use in (1) eliciting GAG-POL dimerization in HIV-infected cells; (2) selectively killing HIV infected GAG-POL expressing cells without concomitant cytotoxicity to HIV naïve cells; (3) treatment or prophylaxis of infection by HIV; (4) the treatment, prophylaxis or delay in the onset or progression of AIDS or ARC; and/or (5) augmenting the suppression of HIV viremia in a subject undergoing treatment with a compatible anti-HIV agent, and/or (6) augmenting the suppression of HIV viremia in a subject whose viremia is being suppressed by administration of one or more compatible HIV antiviral agents.

Additional embodiments of the present invention include each of the pharmaceutical compositions, methods and uses set forth in the preceding paragraphs, wherein the compound of Formula I or its salt employed therein is substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se.

In another embodiment of the present disclosure are the pharmaceutical compositions, methods, medicaments, uses and combinations set forth herein, wherein the HIV of interest is HIV-1. Thus, for example, in any of the pharmaceutical compositions, methods, medicaments, uses and combinations using the compounds of Formula I or pharmaceutically acceptable salts thereof, the compound or salt thereof is employed in an amount effective against HIV-1; and when used in combination with one or more compatible anti-HIV agent(s), each such additional agent is a compatible HIV-1 antiviral selected from, for example but not limited to, one or more of nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

The term "administration" and variants thereof (e.g., "administering" a compound) in reference to a compound of Formula I means providing the compound to the individual in need of treatment or prophylaxis and includes both self-administration and administration to the patient by another person or any other means. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof.

The term "subject" or "patient" as used herein refers to a human (or "person") who has been the object of treatment, observation or experiment. Examples of patients to be treated with an HIV TACK agent include but are not limited to, patients who have been infected with HIV, and/or HIV infected patients whose HIV viral load has been suppressed and/or is considered to be undetectable at time of HIV TACK treatment. Patients to be treated with an HIV TACK agent also include, but are not limited to, those using an HIV TACK agent for prophylaxis of HIV infection or for post-exposure prophylaxis after being potentially exposed to HIV to prevent becoming infected.

"Prophylaxis" includes each of pre-exposure prophylaxis (PrEP), i.e., using a compound of Formula I or a pharmaceutically acceptable salt thereof to prevent HIV infection in a person who does not have HIV, and post-exposure prophylaxis (PEP), i.e., using a compound of Formula I or a pharmaceutically acceptable salt thereof after being potentially exposed to HIV to prevent becoming infected with HIV.

The term "effective amount" as used herein means an amount of a compound sufficient to elicit GAG-POL dimerization in HIV-infected cells and selectively kill HIV infected GAG-POL expressing cells without concomitant cytotoxicity to HIV naïve cells; and/or exert a therapeutic effect, and/or exert a prophylactic effect after administration. One embodiment of "effective amount" is a "therapeutically effective amount" which is an amount of a compound that is effective for selectively killing HIV infected GAG-POL expressing cells, effective for treating HIV infection, or effective for the treatment, prophylaxis or delay in the onset or progression of AIDS or ARC in a patient infected with HIV. Another embodiment of "effective amount" is a "prophylactically effective amount" which is an amount of the compound that is effective for prophylaxis of HIV infection, or prophylaxis of AIDS or ARC in an HIV-infected patient. It is understood that an effective amount can simultaneously be both a therapeutically effective amount, e.g., for treatment of HIV infection, and a prophylactically effective amount, e.g., for prevention or reduction of risk for developing AIDS or ARC in a subject infected with HIV.

In the combination therapies of the present invention, an effective amount can refer to each individual agent or to the combination as a whole, wherein the amounts of all agents administered in the combination are together effective, but wherein a component agent of the combination may or may not be present individually in an effective amount with reference to what is considered effective for that component agent if it were administered alone.

In the methods of the present invention, (i.e., selectively killing HIV infected GAG-POL expressing cells, the treatment of infection by HIV, prophylaxis of HIV infection or the treatment, prophylaxis or delay in the onset or progression of AIDS or ARC and other methods described herein), the compounds of this invention, or salts thereof, can be administered by means that produce contact of the active agent with the agent's site of action. They can be administered by conventional means available for use in conjunction with pharmaceuticals, either as individual therapeutic agents or in a combination of therapeutic agents. The compound can be administered itself, but typically is administered with a pharmaceutical carrier selected on the basis of the chosen route of administration and standard pharmaceutical practice. The compounds of the invention can, for example, be administered orally (e.g., via tablet or capsule), parenterally (including subcutaneous injections, intravenous, intramuscular or intrasternal injection, or infusion techniques), by inhalation spray, or rectally, in the form of a unit dosage of a pharmaceutical composition containing an effective amount of the compound and conventional non-toxic pharmaceutically acceptable carriers, adjuvants and vehicles. The compound could also be administered via an implantable drug delivery device adapted to provide an effective amount of the compound or a pharmaceutical composition of the compound over an extended period of time.

Formulations

Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Liquid preparations suitable for oral administration (e.g., suspensions, syrups, elixirs and the like) can be prepared according to techniques known in the art and can employ any of the usual media such as water, glycols, oils, alcohols and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Implantable compositions can be prepared according to methods known in the art wherein the carrier comprises the active chemical ingredient with polymers and suitable excipients, or utilizing an implantable device for drug delivery. Further description of methods suitable for use in preparing pharmaceutical compositions for use in the present invention and of ingredients suitable for use in said compositions is provided in Remington—The Science and Practice of Pharmacy, 22nd Edition, published by Pharmaceutical Press and Philadelphia College of Pharmacy at University of the Sciences, 2012, ISBN 978 0 85711-062-6 and prior editions.

Formulations of compounds of Formula I that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are known in the art. For example, solid dispersions can be prepared using excipients and processes as described in reviews (e.g., A. T. M. Serajuddin, J Pharm Sci, 88:10, pp. 1058-1066 (1999)). Nanoparticulate systems based on both attrition and direct synthesis have also been described in reviews such as Wu et al (F. Kesisoglou, S. Panmai, Y. Wu, Advanced Drug Delivery Reviews, 59:7 pp. 631-644 (2007)).

The compounds of Formula I may be administered in a dosage range of, e.g., 1 to 20 mg/kg, or 1 to 10 mg/kg, or about 5 mg/kg of mammal (e.g., human) body weight per day, or at other time intervals as appropriate, in a single dose or in divided doses. The compounds of Formula I may be administered in a dosage range of 0.001 to 2000 mg. per day in a single dose or in divided doses. Examples of dosage ranges are 0.01 to 1500 mg per day, or 0.1 to 1000 mg per day, administered orally or via other routes of administration in a single dose or in divided doses.

For oral (e.g., tablets or capsules) or other routes of administration, the dosage units may contain 100 mg to 1500 mg of the active ingredient, for example but not limited to, 100, 150, 200, 250, 300, 350, 400, 450, 500, 600, 700, 800, 900, 1000, 1100, 1200, 1300, 1400 or 1500 milligrams of the active ingredient for the symptomatic adjustment of the dosage to the patient to be treated. Furthermore, the compound may be formulated in oral formulations for immediate or modified release such as extended or controlled release. When the compound of Formula I is administered as a salt, reference to an amount of the compound in milligrams or grams is based on the free form (i.e., the non-salt form) of the compound.

Daily administration can be via any suitable route of administration but is preferably via oral administration and can be a single dose or more than one dose at staggered times (divided daily doses) within each 24-hour period. Each dose may be administered using one or multiple dosage units as appropriate.

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In some cases, depending on the potency of the compound or the individual response, it may be necessary to deviate upwards or downwards from the given dose. The amount and frequency of administration will be regulated according to the judgment of the attending clinician considering such factors.

An "anti-HIV agent" is any agent which is directly or indirectly effective in the inhibition of HIV, the treatment or prophylaxis of HIV infection, and/or the treatment, prophylaxis or delay in the onset or progression of AIDS or ARC. It is understood that an anti-HIV agent is effective in treating, preventing, or delaying the onset or progression of HIV infection or AIDS and/or diseases or conditions arising therefrom or associated therewith. The present disclosure is additionally directed to use of a compound of Formula I or pharmaceutically acceptable salts thereof, with one or more compatible anti-HIV agents, i.e., anti-HIV agents excluding HIV protease inhibitors (also referred to as "compatible HIV antivirals"). For example, the compounds of Formula I may be administered in combination with effective amounts of one or more compatible anti-HIV agents selected from HIV antiviral agents, immunomodulators, anti-infectives, or vaccines useful for treating HIV infection or AIDS. Suitable compatible HIV antivirals for use in combination with the compounds of the present disclosure include, but are not limited to, those listed in Table A as follows:

TABLE A

Antiviral Agents for Treating HIV infection or AIDS

| Name | Type |
|---|---|
| abacavir, ABC, ZIAGEN ® | NRTI |
| abacavir + lamivudine, EPZICOM ® | NRTI |
| abacavir + lamivudine + zidovudine, TRIZIVIR ® | NRTI |
| AZT, zidovudine, azidothymidine, RETROVIR ® | NRTI |
| bictegravir | InSTI |
| bictegravir + tenofovir alafenamide fumarate + emtricitabine, BIKTARVY ® | InSTI/NRTI/NRTI |
| capravirine | NNRTI |
| cabotegravir | InSTI |
| Cabotegravir + rilpivirine, CABENUVA | InSTI/NNRTI |
| ddC, zalcitabine, dideoxycytidine, HIVID ® | NRTI |
| ddI, didanosine, dideoxyinosine, Videx ® | NRTI |
| ddI (enteric coated), VIDEX EC ® | NRTI |
| delavirdine, DLV, RESCRIPTOR ® | NNRTI |
| Dolutegravir + lamivudine, DOVATO ® | InSTI/NRTI |
| Dolutegravir + rilpivirine, JULUCA ® | InSTI/NNRTI |
| dolutegravir, TIVICAY ® | InSTI |
| dolutegravir + abacavir + lamivudine, TRIUMEQ ® | InSTI/NRTI/NRTI |
| doravirine, PIFELTRO ™ | NNRTI |
| doravirine/lamivudine/tenofovir disoproxil fumarate, DELSTRIGO ™ | NNRTI/NRTI/NRTI |
| efavirenz, EFV, SUSTIVA ®, STOCRIN ® | NNRTI |
| Efavirenz/emtricitabine/tenofovir disoproxil fumarate, ATRIPLA ® | NNRTI/NRTI/NRTI |
| Islatravir, (4'-ethynyl-2-fluoro-2'-deoxyadenosine; EFdA) | NRTTI |
| Elvitegravir, VITEKTA ® | InSTI |
| emtricitabine, FTC, EMTRIVA ® | NRTI |
| emtricitabine + tenofovir alafenamide fumarate, DESCOVY ® | NRTI/NRTI |
| emtricitabine + tenofovir disoproxil fumarate, TRUVADA ® | NRTI/NRTI |
| emivirine, COACTINON ® | NNRTI |
| enfuvirtide, FUZEON ® | FI |
| enteric coated didanosine, VIDEX EC ® | NRTI |
| etravirine, TMC-125 | NNRTI |
| Fostemsavir, RUKOBIA ® | AI |
| Ibalizumab-uiyk (TROGARZO ®) | Post-Attachment Inhibitor or Monoclonal Antibody |
| lamivudine, 3TC, EPIVIR ® | NRTI |
| lamivudine + zidovudine, COMBIVIR ® | NRTI/NRTI |
| lenacapavir | Capsid inhibitor |
| maraviroc, SELZENTRY ® | EI |
| nevirapine, NVP, VIRAMUNE ® | NNRTI |
| raltegravir, ISENTRESS ™ | InSTI |
| rilpivirine, EDURANT ® | NNRTI |
| stavudine, d4T, didehydrodeoxythymidine, ZERIT ® | NRTI |
| tenofovir disoproxil fumarate (TDF), VIREAD ® | NRTI |
| tenofovir alafenamide fumarate (TAF) | NRTI |
| vicriviroc | EI |

AI = attachment inhibitor; EI = entry inhibitor; FI = fusion inhibitor; InSTI = integrase inhibitor; NRTI = nucleoside or nucleotide reverse transcriptase inhibitor; NNRTI = non-nucleoside reverse transcriptase inhibitor; NRTTI = nucleoside reverse transcriptase translocation inhibitor. Some of the drugs listed in Table A are used in a salt form; e.g., abacavir sulfate, delavirdine mesylate.

The TACK effect elicited by an HIV-TACK agent depends on expression of viral Gag-Pol. Therefore additional active agents, such as latency reversing agents ("LRA" or "LRAs"), that enhance Gag-Pol production in infected cells and/or activate viral expression in cells that comprise the latent HIV reservoir, when used together with HIV-TACK therapy, are likely to enhance the TACK effect. The present disclosure is additionally directed to use of a compound of Formula I, or a pharmaceutically acceptable salt thereof, with one or more LRA(s). For example, the compounds of Formula I may be administered in combination with effective amounts of one or more LRA(s) for treatment of HIV infection or AIDS. Examples of LRAs for use in combination with the compounds of the present disclosure include, but are not limited to epigenetic modifiers such as histone deacetylase (HDAC) inhibitors, DNA methyltransferase (DNMT) inhibitors, and histone methyltransferase (HMT) inhibitors; Protein Kinase C (PKC) agonists such as prostratins, bryostatins, or ingenols; inducers of P-TEFb release such as BET inhibitors (e.g., JQ1 or a class of drugs that reversibly bind the bromodomains of Bromodomain and Extra-Terminal motif (BET) proteins BRD2, BRD3, BRD4, and/or BRDT), antagonists of C—C chemokine receptor type 5 (CCR5), inducers of non-canonical NF-κB pathway (e.g., second mitochondria-derived activator of caspases (SMAC) mimetics or inhibitor of apoptosis proteins (IAP) antagonists, proteasome inhibitors, toll-like receptor (TLR) agonists, mitogen-activated protein kinase (MAPK) agonists, Ak strain transforming/protein kinase B (AKT/PKB) pathway activators, cytokines and immunomodulatory agents such as immune checkpoint inhibitors and those described elsewhere such as Bullen et al, Nature Medicine, 20:425-429 (2014); Ait-Ammar et al, Frontiers in Microbiology, 10:3060 (2019); and Fujinaga et al, Viruses. 12:11 (2020).

Examples of HDAC inhibitors that can be used as latency reversing agents include, but are not limited to, vorinostat, panabinostat, romidepsin, and valproic acid. Examples of DNMT inhibitors that can be used as latency reversing agents include, but are not limited to, 5-aza-2'-cytidine and 5-aza-2'-deoxycytidine. Examples of HMT inhibitors that can be used as latency reversing agents include, but are not limited to, chaetocin, 3-deazaneplanocin A, tazemetostat (EPZ-6438), N-[(1,2-dihydro-6-methyl-2-oxo-4-propyl-3-pyridinyl)methyl]-1-(1-methylethyl)-6-[2-(4-methyl-1-piperazinyl)-4-pyridinyl]-1H-indazole-4-carboxamide (GSK-343) and 2-cyclohexyl-6-methoxy-N-[1-(1-methylethyl)-4-piperidinyl]-7-[3-(1-pyrrolidinyl)propoxy]-4-quinazolinamine (UNC-0638). Examples PKC agonists that can be used as latency reversing agents include, but are not limited to, phorbolesters such as prostratin and phorbol myristate acetate (PMA), bryostatin-1, and ingenol. Examples of BET inhibitors that can be used as a latency reversing agents include, but are not limited to, JQ1 ((S)-tert-butyl 2-(4-(4-chlorophenyl)-2,3,9-trimethyl-6H-thieno[3,2-f][1,2,4]triazolo[4,3-a][1,4]diazepin-6-yl)acetate), iBET, and N-cyclohexyl-2-(4-(3,5-dimethylisoxazol-4-yl)-2-methoxyphenyl)imidazo[1,2-a]pyrazin-3-amine (UMB-136). An example of a CCR5 antagonist that can be used as latency reversing agent includes, but is not limited to, maraviroc. Examples of inducers of the non-canonical NF-κB pathway and SMAC mimetics/IAP inhibitors that can be used as latency reversing agents include, but are not limited to, 3,3-[2,4-hexadiyne-1,6-diylbis[oxy[(1,2R)-2,3-dihydro-1H-indene-2,1-diyl]]]bis[N-methyl-L-alanyl-(2S)-2-cyclohexylglycyl-L-prolinamide (AZD5582), Ciapavir, Birinapant, LCL161, and DEBIO1143/AT-406. Examples of proteasome inhibitors that can be used as latency reversing agents include, but are not limited to, bortezomib and ixazomib. Examples of TLR agonists that can be used as latency reversing agents include, but are not limited to, the TLR2 agonist Pam3CSK4, the TLR7 agonist vesatolimod, and the TLR9 agonists Lefitolimod (MGN1703) and CPG 7909.

An example of an MAPK agonist that can be used as a latency reversing agent includes, but is not limited to, procyanidin trimer C1. An example of an AKT pathway activator that can be used as latency reversing agent includes, but is not limited to, disulfiram. Examples of immunomodulatory cytokines that can be used as latency reversing agents include, but are not limited to, IL-2, IL-7, and IL-15, including the IL-15 superagonist N-803. Examples of immune checkpoint inhibitors include, but are not limited to, inhibitors of Programmed cell death protein 1 (PD1), Programmed death-ligand 1 (PD-L1) inhibitors, cytotoxic T-lymphocyte-associated protein 4 (CTLA-4), Lymphocyte-activation gene 3 (LAG3), T cell immunoreceptor with Ig and ITIM domains) (TIGIT) and CD24Fc, a recombinant fusion protein composed of the extracellular domain of the mature human glycoprotein cluster of differentiation 24 (CD24) linked to a human immunoglobulin G1 (IgG1) Fc domain.

Thus, the compounds of Formula I, or pharmaceutically acceptable salts thereof, used together with a latency reversing agent can be useful for:

(i) A method for re-activating latent HIV and eliciting GAG-POL dimerization in HIV-infected cells (e.g., CD4 T cells) in a human subject which comprises administering to the subject an effective amount of a compound according to Formula I, or a pharmaceutically acceptable salt thereof, and a latency reversing agent; and/or (ii) A method for re-activating latent HIV and selectively killing HIV-infected GAG-POL expressing cells (e.g., latently HIV-infected CD4 T cells or central memory CD4 T cells), without concomitant cytotoxicity to HIV naïve cells, in a human subject which comprises administering to the subject an effective amount of a compound according to Formula I, or a pharmaceutically acceptable salt thereof, and a latency reversing agent.

Compounds of this invention can be used in combination with any one or more of antiviral agents, e.g. but not limited to those listed in Table A, and/or any one or more of LRAs, e.g. but not limited to, the LRAs described herein.

It is understood that the scope of combinations of the compounds of this invention with compatible anti-HIV agents is not limited to the HIV antivirals listed in Table A, but includes in principle any combination with any pharmaceutical composition useful for the treatment or prophylaxis of HIV AIDS, or ARC, with the exception of HIV protease inhibitors. The compatible HIV antiviral agents and other active agents will typically be employed in these combinations in their conventional dosage ranges and regimens as reported in the art, including, for example, the dosages described in the current Physicians' Desk Reference, Thomson PDR, 70th edition (2016), Montvale, N.J.: PDR Network, or in prior editions thereof. The dosage ranges for a compound of the disclosure in these combinations can be the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds.

Furthermore, the compounds of this invention are useful in establishing or determining the binding site of other antivirals to the reverse transcriptase region within GAG-POL, e.g., by competitive inhibition.

The following acronyms and abbreviations used herein have the indicated meanings: AcOH=Acetic acid; aq=aqueous; BisPin=bis(pinacolato)diboron; CAN=ceric ammonium nitrate; d=doublet; DAST=(diethylamino)sulfur trifluoride; DCE=1,2-dichloroethane; DCM=dichloromethane; DIPEA=diisopropylethylamine; DMA=dimethylacetamide; DMF=N,N-dimethylformamide; DMAP=4-dimethylaminopyridine; DMP=Dess-Martin periodinane; DMSO=dimethyl sulfoxide; dppf=1,1'-Bis(diphenylphosphino)ferrocene; Et=ethyl; EtOAc=ethyl acetate; EtOH=ethanol; HIV=human immunodeficiency virus; HPLC=high performance liquid chromatography; hr or h=hour; iPrOH=isopropanol; L=liter; Lawesson's reagent=2,4-bis(4-methoxyphenyl)-2,4-dithioxo-1,3,2,4-dithiadiphosphetane; LDA=lithium diisopropylamide; LiHMDS=lithium bis(trimethylsilyl)amide; m=multiplet; Me=methyl; MeCN=acetonitrile; MeOH=methanol; MHz=megahertz; min=minute; mL or ml=milliliters; mmol=millimoles; MPLC=medium pressure liquid chromatography; MS (ESI)=mass spectroscopy (electrospray ionization); MsCl=methanesulfonyl chloride; NBS=N-bromosuccinimide; NCS=N-chlorosuccinimde; NHS=normal human serum; NIS=N-iodosuccinimde; nBu=n-butyl; nM=nanomolar; NMR=nuclear magnetic resonance; PE=petroleum ether; Pin=pinacolato boronate ester; PMB=4-methoxybenzyl; PMBCl=4-methoxybenzyl chloride; prep=preparative; pTsOH=p-toluenesulfonic acid; RNA=ribonucleic acid; s=singlet; sat aq=saturated aqueous; sol=solution; t=triplet; TBAF=tetra-N-butylammonium fluoride; TBSCl=tert-butyldimethylsilyl chloride; t-Bu=tert-butyl; THF=tetrahydrofuran; TFA=trifluoroacetic acid; TFAA=trifluoroacetic anhydride; TLC=thin layer chromatography; TMS=trimethylsilyl; TMSCl=trimethylsilyl chloride; Xphos=2-Dicyclohexylphosphino-2',4',6'-triisopropylbiphenyl; XPhos Pd G2=Chloro(2-dicyclohexylphosphino-2',4',6'-triisopropyl-1,1'-biphenyl)[2-(2'-amino-1,1'-biphenyl)]palladium(II).

Several methods for preparing the compounds of this invention are described in the following Schemes and Examples. Starting materials and intermediates are purchased or are made using known procedures, or as otherwise illustrated in the three Intermediate (A, B, and C) sections that follow. A frequently applied route to the compounds of Formula I are described in the Schemes that follow.

SCHEME 1

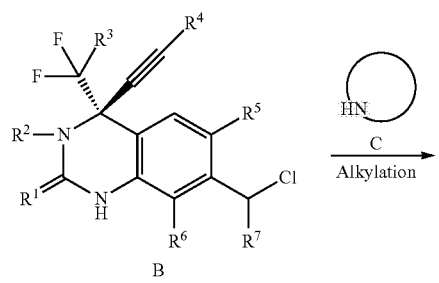

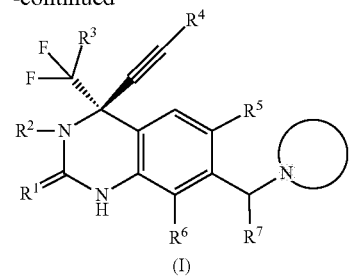

Scheme 1 depicts a method for preparing compounds of Formula I. Intermediate B is prepared with procedures illustrated in the Intermediate B section. Alkylation reaction using an appropriate 6-membered heterocyclic ring (Intermediate C) provides compounds of Formula I. Synthesis of C is illustrated in the Intermediate C section.

Reactions sensitive to moisture or air were performed under nitrogen or argon using anhydrous solvents and reagents. Reactions performed using microwave irradiation were normally carried out using an Emrys Optimizer manufactured by Personal Chemistry, or an Initiator manufactured by Biotage. Concentration of solutions was carried out on a rotary evaporator under reduced pressure.

The progress of reactions was determined by either analytical thin layer chromatography (TLC) usually performed with E. Merck pre-coated TLC plates, silica gel 60F-254, layer thickness 0.25 mm or analytical liquid chromatography-mass spectrometry (LC-MS). Typically, the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50 mm, 5 m or a Waters Acquity UPLC® BEH C18 1.0×50 mm, 1.7 m. The flow rate was 1 mL/min, and the injection volume was 10 μL. UV detection was in the range 210-400 nm. The mobile phase consisted of solvent A (water plus 0.05% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min. LC/MS determinations were carried out on a Waters Classing Aquity system equipped with TUV and MS detectors and a Waters SQD mass spectrometer, a Shimadzu 20 UV 254 and 220 nM with Shimadzu 2010 or 2020 mass spectrometer, or an Agilent 1200 HPLC quipped with DAD/ELSD and G6110 MSD using one of the following conditions: 1) Ascentis Express C18 (3×50 mm) 2.7 m column using mobile phase containing A: 0.05% Trifluoroacetic acid in water and B: 0.05% Trifluoroacetic acid in acetonitrile with a gradient from 90:10 (A:B) to 5:95 (A:B) over 6 min at a flow rate of 1.8 mL/min, UV detection at 210 nm; 2) Aquity BEH C18, (1.0×50 mm) 1.7 m column using mobile phase containing A: 0.05% Trifluoroacetic acid in water and B: 0.05% Trifluoroacetic acid in acetonitrile with a gradient from 90:10 (A:B) to 5:95 (A:B) over 2 min at a flow rate of 0.3 mL/min, UV detection at 215 nm; 3) Agilent YMC J'Sphere H-80 (3×50 mm) 5 m column using mobile phase containing A: 0.1% Trifluoroacetic acid in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer; 4) an Agilent TC-C18 (2.1×50 mm) 5 m column using mobile phase containing A: 0.0375% Trifluoroacetic acid in water and B: 0.01875% Trifluoroacetic acid in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

Preparative HPLC purifications were usually performed using either a mass spectrometry directed system or a non-mass guided system. Usually they were performed on a Waters Chromatography Workstation configured with LC-MS System consisting of: Waters ZQ™ single quad MS system with Electrospray Ionization, Waters 2525 Gradient Pump, Waters 2767 Injecto/Collector, Waters 996 PDA Detector, the MS Conditions of: 150-750 amu, Positive Electrospray, Collection Triggered by MS, and a Waters SUNFIRE® C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. An alternate preparative HPLC system used was a Gilson Workstation consisting of: Gilson GX-281 Injector/Collector, Gilson UV/VIS-155 Detector, Gilson 333 and 334 Pumps, and equipped with a column selected from the following: Phenomenexd Synergi C18 (150 mm×30 mm×4 micron), YMC-Actus Pro C18 (150 mm×30 mm×5 micron), Xtimate C18 (150 mm×25 mm×5 micron), Boston Green ODS (150 mm×30 mm×5 micron), XSELECT C18 (150 mm×30 mm×5 micron), and Waters XSELECT C18 (150 mm×30 mm×5 micron). Conditions included either high pH (0-100% acetonitrile/water eluent comprising 0.1% v/v 10 mM NH$_4$HCO$_3$ or 0.05% NH$_4$OH) or low pH (0-95% acetonitrile/water eluent comprising 0.1% v/v TFA). The injection volume ranged from 1000-8000 μL, and the UV detection range was 210-400 nm. Mobile phase gradients were optimized for the individual compounds.

Flash chromatography was usually performed using either a Biotage® Flash Chromatography apparatus (Dyax Corp.), an ISCO CombiFlash® Rf apparatus, or an ISCO CombiFlash® Companion XL on silica gel (32-63 μm, 60 Å pore size) in pre-packed cartridges of the size noted.

SFC chiral resolution was carried out on a Sepiate Prep SFC 100, Multigram II (MG II), THAR80 prep SFC, or a Waters SFC (80, 200, or 350).

Chiral preparative chromatography was conducted on one of of CHIRALPAK AS, of CHIRALPAK AD, CHIRALCEL® OD, CHIRALCEL® IA, CHIRALCEL® OJ columns (20×250 mm) (Daicel Chemical Industries, Ltd.) or WHELK-O® 1 (Regis Technologies, Inc.) with desired isocratic solvent systems identified on chiral analytical chromatography or by supercritical fluid (SFC) conditions.

Proton or $^1$H NMR was acquired using a Varian Unity-Inova 400 MHz NMR spectrometer equipped with a Varian 400 ATB PFG 5 mm, Nalorac DBG 400-5 or a Nalorac IDG 400-5 probe, a Varian-400 MHz MR spectrometer equipped with an Auto X ID PFG Probe 5 mm, a Varian 400 MHz VNMRS spectrometer equipped with a PFG 4Nuc Probe 5 mm, or a Bruker Avance III 500 MHz spectrometer equipped with a PABBO Probe 5 mm in accordance with standard analytical techniques, unless specified otherwise, and results of spectral analysis are reported. $^1$H NMR spectra were acquired in CDCl$_3$ solutions unless otherwise noted. Chemical shifts were reported in parts per million (ppm). Tetramethylsilane (TMS) was used as internal reference in CD$_3$Cl solutions, residual CH$_3$OH peak or TMS was used as internal reference in CD$_3$OD solutions, and TMS was used as internal reference in DMSO-d6 solutions. Coupling constants (J) were reported in hertz (Hz).

It is understood that a chiral center in a compound may exist in the "S" or "R" stereo-configuration, or as a mixture of both. Within a molecule, each bond drawn as a straight line from a chiral center encompasses each of the (R) and (S) stereoisomers as well as mixtures thereof unless otherwise noted. The compounds in Examples 75, 76, 77, 78 and 79 contain a chiral center. The isomer mixture made in each of Examples 75, 76, 77, 78 and 79 was separated, providing one or both of an isomer A (the faster eluting isomer) and an isomer B (the slower eluting isomer), based on their observed elution order resulting from the separation as performed in the Example. Elution time and/or order of separated isomers may differ if performed under conditions different than those employed herein. Absolute stereochemistry (R or S) of the chiral center in each of the "A" and/or "B" separated stereoisomers in Examples 75, 76, 77, 78 and 79 was not determined, and "A" and "B" only refer to elution order resulting from the purification conditions as performed. An asterisk (*) may be used in the associated chemical structure drawings of the Intermediate and Example compounds to indicate a chiral center.

Compounds containing a bromine have two masses due to the two bromide isotopes, $^{79}$Br and $^{81}$Br in an approximately 1:1 ratio.

Intermediates: Section A

Intermediate A01, Isomer A01-A and Isomer A01-B: (S)-7-bromo-4-(cyclopropylethynyl)-1-(4-methoxybenzyl)-4-(trifluoromethyl)-3,4-dihydroquinazolin-2(1H)-one and (R)-7-bromo-4-(cyclopropylethynyl)-1-(4-methoxybenzyl)-4-(trifluoromethyl)-3,4-dihydroquinazolin-2(1H)-one

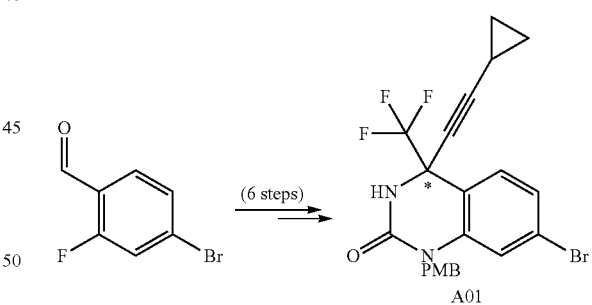

Step 1: 1-(4-bromo-2-fluorophenyl)-2,2,2-trifluoroethanol: To a solution of 4-bromo-2-fluorobenzaldehyde (40 g, 197 mmol) and trimethyl(trifluoromethyl)silane (30.8 g, 217 mmol) in THF (240 mL) was added TBAF (3.94 mL, 3.94 mmol) at 0° C. The mixture was stirred for 3 h at 20° C. Additional TBAF (39.4 mL, 39.4 mmol) was added. The mixture was stirred for 10 min. HCl (1M, 180 mL) was added and the mixture was stirred for 0.5 h. The mixture was diluted with H$_2$O (600 mL) and extracted with EtOAc (2×400 mL) and washed with brine and dried over Na$_2$SO$_4$, filtered and concentrated to give the title compound, which was used without further purification.

Step 2: 1-(4-bromo-2-fluorophenyl)-2,2,2-trifluoroethanone: A mixture of 1-(4-bromo-2-fluorophenyl)-2,2,2-trifluoroethanol (51.7 g, 189 mmol) and DMP (161 g, 379 mmol) and NaHCO$_3$ (47.7 g, 568 mmol) in DCM (510 mL) was stirred for 3 h at 20° C. The mixture was washed with sat aq NaHCO$_3$ sol (2×500 mL), H$_2$O (2×500 mL) and brine (500 mL), and dried over Na$_2$SO$_4$, filtered and concentrated. The crude product was purified by flash chromatography (SiO$_2$, 0-30% EtOAc/PE) to provide the title compound.

Step 3: 1-(4-bromo-2-((4-methoxybenzyl)amino)phenyl)-2,2,2-trifluoroethanone: A mixture of 1-(4-bromo-2-fluorophenyl)-2,2,2-trifluoroethanone (33 g, 122 mmol) and (4-methoxyphenyl)methanamine (33.4 g, 244 mmol) in toluene (330 mL) was stirred at 120° C. for 2 h. The mixture was washed with 10% citric acid aq sol (2×330 mL) and brine (330 mL) and dried over Na$_2$SO$_4$ and filtered and concentrated. The crude product was purified by flash chromatography (SiO$_2$, 0-30% EtOAc/PE) to the title compound.

Step 4: 7-bromo-4-hydroxy-1-(4-methoxybenzyl)-4-(trifluoromethyl)-3,4-dihydroquinazolin-2(1H)-one: To a solution of 1-(4-bromo-2-((4-methoxybenzyl)amino)phenyl)-2,2,2-trifluoroethanone (100 g, 258 mmol) in AcOH (500 mL) and H$_2$O (50 mL) was added sodium cyanate (100 g, 1546 mmol). The mixture was stirred at 60° C. for 4 h. The mixture was diluted with H$_2$O (500 mL) and filtered to give the crude product. The crude product was diluted with sat aq NaHCO$_3$ sol (500 mL) and extracted with EtOAc (3×300 mL), and the combined organic phase was washed with brine (900 mL), dried over Na$_2$SO$_4$, filtered and concentrated to give the title compound, which was used directly without further purification.

Step 5: 7-bromo-1-(4-methoxybenzyl)-4-(trifluoromethyl)quinazolin-2(H)-one: A solution of 7-bromo-4-hydroxy-1-(4-methoxybenzyl)-4-(trifluoromethyl)-3,4-dihydroquinazolin-2(1H)-one (98 g, 227 mmol) in toluene (700 mL) was stirred at 130° C. for 16 h, and was then concentrated to give the title product, which was used directly without further purification.

Step 6: (S)-7-bromo-4-(cyclopropylethynyl)-1-(4-methoxybenzyl)-4-(trifluoromethyl)-3,4-dihydroquinazolin-2(1H)-one AND (R)-7-bromo-4-(cyclopropylethynyl)-1-(4-methoxybenzyl)-4-(trifluoromethyl)-3,4-dihydroquinazolin-2(1H)-one: To a solution of ethynylcyclopropane (5.32 g, 80.46 mmol) in toluene (260 mL), LiHMDS (66.9 ml, 66.9 mmol) was added at −5° C. The mixture was heated to 85° C. for 15 min and then cooled to −15° C. A solution of 7-bromo-1-(4-methoxybenzyl)-4-(trifluoromethyl)quinazolin-2(1H)-one (6 g, 13.4 mmol) in THF (520 ml) was added, and the mixture was stirred for 12 h at 20° C. The reaction mixture was poured into an aq NH$_4$Cl sol (1200 mL), extracted with EtOAc (3×600 mL). The combined organic phase was washed with brine (1800 mL), filtered and concentrated. The crude was purified by flash chromatography (SiO$_2$, 0-30% EtOAc/PE) to give the title compound. The racemic mixture was resolved by prep SFC (IC-H column, 40% MeOH (0.1% NH$_3$H$_2$O)/CO$_2$, 66 mL/min, 100 bar, 40° C.) to provide Isomer A01-A (faster eluting) and Isomer A01-B (slower eluting). MS (ESI) m/z 479, 481 [M+] for both.

The following racemic intermediates were prepared using a procedure analogous to that used for making A01 using 2-methyl-3-butyne or 4-methylpent-1-yne, respectively, in place of ethynylcyclopropane.

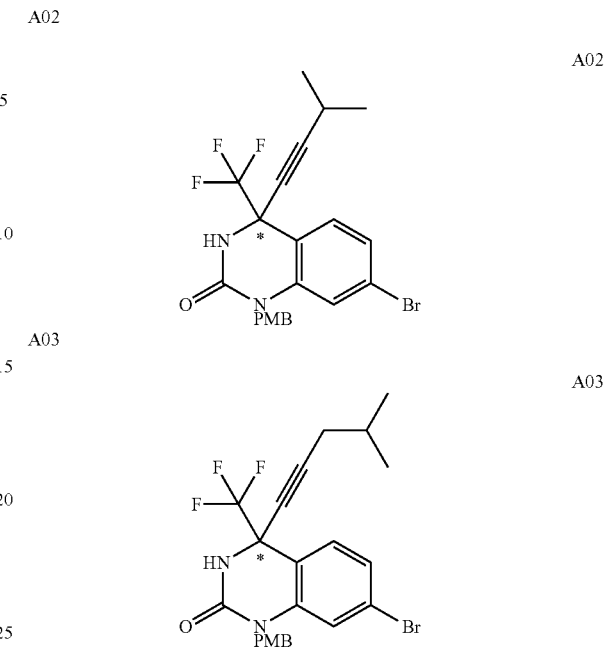

A02

A03

Intermediate A04: 7-chloro-4-(cyclopropylethynyl)-4-(trifluoromethyl)-3,4-dihydropyrido[2,3-d]pyrimidin-2(1H)-one

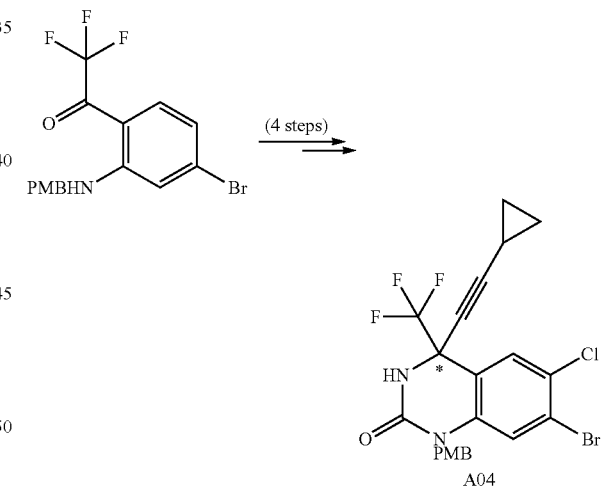

Step 1: 1-(4-bromo-5-chloro-2-((4-methoxybenzyl)amino)phenyl)-2,2,2-trifluoroethanone: To a mixture of 1-(4-bromo-2-((4-methoxybenzyl)amino)phenyl)-2,2,2-trifluoroethanone (44 g, 113 mmol) in DMF (440 mL) was added NCS (15.9 g, 119 mmol) and the mixture was stirred at 50° C. for 1.5 h. The reaction was quenched with H$_2$O (1 L), and the mixture was extracted with EtOAc (3×400 mL). The combined organic layer was washed with brine (1.2 L), dried over anhydrous Na$_2$SO$_4$, filtered and concentrated to give the title product, which was used directly without further purification.

Step 2: 7-bromo-6-chloro-4-hydroxy-1-(4-methoxybenzyl)-4-(trifluoromethyl)-3,4-dihydroquinazolin-2(1H)-one:

To a solution of 1-(4-bromo-5-chloro-2-((4-methoxybenzyl)amino)phenyl)-2,2,2-trifluoroethanone (47 g, 111 mmol) in AcOH (400 mL) and H$_2$O (40 mL) was added sodium cyanate (50.6 g, 778 mmol). The mixture was stirred at 60° C. for 3 h. The reaction was quenched into sat aq NaHCO$_3$ sol (500 mL), and the mixture was extracted with EtOAc (3×300 mL). The combined organic layers were washed with brine (900 mL), dried over anhydrous Na$_2$SO$_4$, filtered and concentrated. The mixture was purified by flash chromatography (SiO$_2$, 0-30% EtOAc/PE) to afford the title compound.

Step 3: 7-bromo-6-chloro-1-(4-methoxybenzyl)-4-(trifluoromethyl)quinazolin-2(H)-one A solution of 7-bromo-6-chloro-4-hydroxy-1-(4-methoxybenzyl)-4-(trifluoromethyl)-3,4-dihydroquinazolin-2(1H)-one (7 g, 15.03 mmol) in toluene (4 mL) was stirred at 120° C. for 16 h. The reaction was concentrated to give the title compound, which was used directly without further purification.

Step 4: 7-chloro-4-(cyclopropylethynyl)-4-(trifluoromethyl)-3,4-dihydropyrido[2,3-d]pyrimidin-2(1H)-one: To a solution of ethynylcyclopropane (6.20 g, 94 mmol) in toluene (350 mL), LiHMDS (78 mL, 78 mmol) was added at −5° C. The mixture was heated at 85° C. for 15 min and then cooled to −15° C. A solution of 7-bromo-6-chloro-1-(4-methoxybenzyl)-4-(trifluoromethyl)quinazolin-2(1H)-one (7 g, 15.64 mmol) in THF (700 mL) was added, and the mixture was stirred for 16 h at 20° C. The reaction mixture was poured into a sat aq NH$_4$Cl sol (1200 mL), extracted with EtOAc (3×600 mL). The combined organic phase was washed with brine (1800 mL), filtered and concentrated. The crude product was purified by HPLC (SiO$_2$, 10-50% EtOAc:PE) to give the title compound.

Intermediate A05: 7-bromo-6-chloro-4-(cyclopropylethynyl)-1-(4-methoxybenzyl)-3-methyl-4-(trifluoromethyl)-3,4-dihydroquinazolin-2(1H)-one

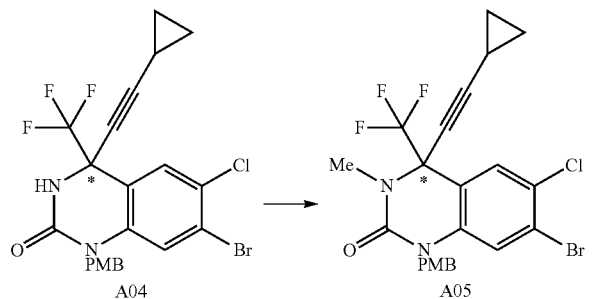

To a solution of intermediate A04 (500 mg, 0.973 mmol) in DMF (5 mL), NaH (97 mg, 2.433 mmol) and MeI (0.183 ml, 2.92 mmol) were sequentially added at 15° C. The resulting mixture was stirred at 50° C. for 2 h. The mixture was then diluted with H$_2$O (50 mL), and then extracted with EtOAc (3×50 mL). The combined organic layer was washed with brine (3×50 mL), dried over Na$_2$SO$_4$, filtered, and concentrated. The resulting residue was purified by flash chromatography (SiO$_2$, 0-20% EtOAc/PE) to afford the title compound. MS (ESI) m/z 527, 529 [M+1].

Intermediate A06: 7-bromo-4-(cyclopropylethynyl)-4-(trifluoromethyl)-3,4-dihydroquinazolin-2(1H)-one

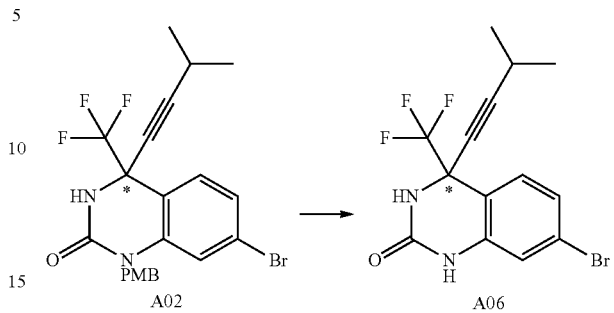

To a solution of intermediate A02 in MeCN (20 mL) and H$_2$O (7 mL) was added CAN (6834 mg, 12.47 mmol). The reaction was stirred at 15° C. for 2 h. The reaction was dissolved in H$_2$O (50 mL) and extracted with EtOAc (3×50 mL). The combined organic layer was washed with brine (50 mL), dried over Na$_2$SO$_4$, filtered and concentrated. The crude product was purified by flash chromatography (SiO$_2$, 0-20% EtOAc/PE) to give the title compound. MS (ESI) m/z 360, 362 [M+1].

The following intermediates were prepared using a procedure analogous to that used for making A06 using the noted starting intermediate in place of A02.

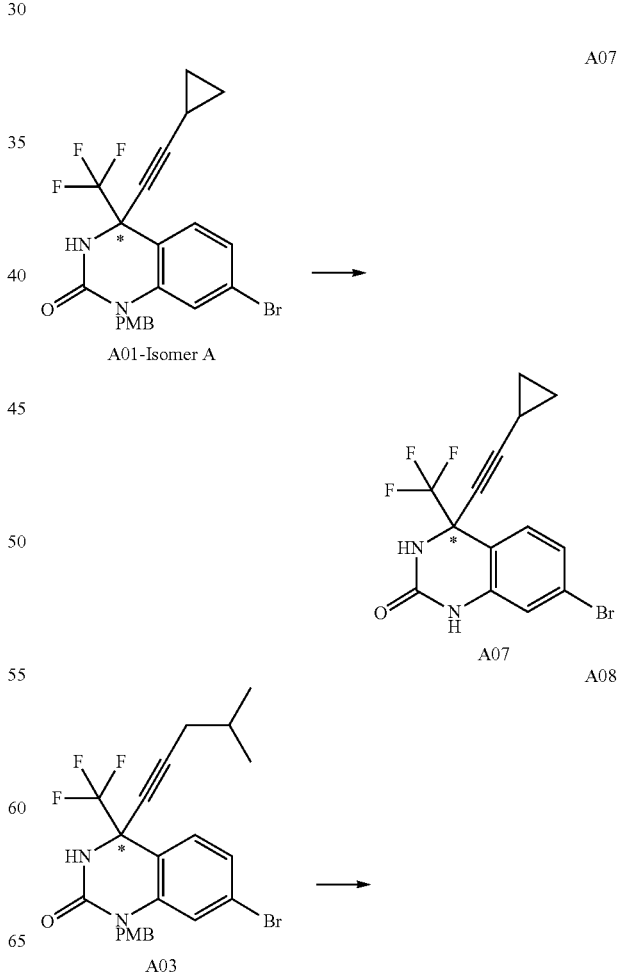

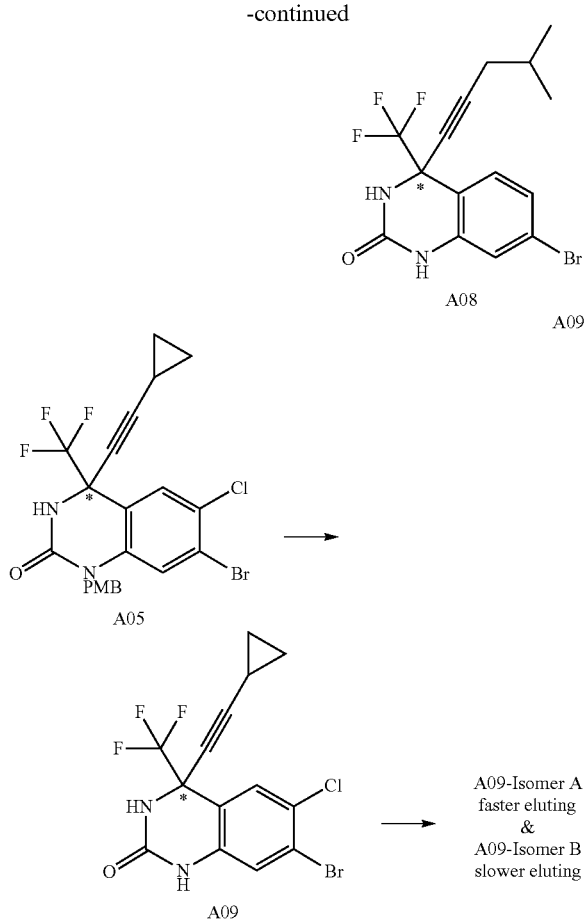

A09 racemic mixture was resolved by prep SFC (Chiralpak AD-H, 15% MeOH/CO₂; 60 mL/min; 40° C.; 100 bar)

Intermediate A10, Isomer A10-A and Isomer A10-B: (S)-7-bromo-4-(cyclopropylethynyl)-6-fluoro-4-(trifluoromethyl)-3,4-dihydroquinazolin-2(1H)-one and (R)-7-bromo-4-(cyclopropylethynyl)-6-fluoro-4-(trifluoromethyl)-3,4-dihydroquinazolin-2(1H)-one

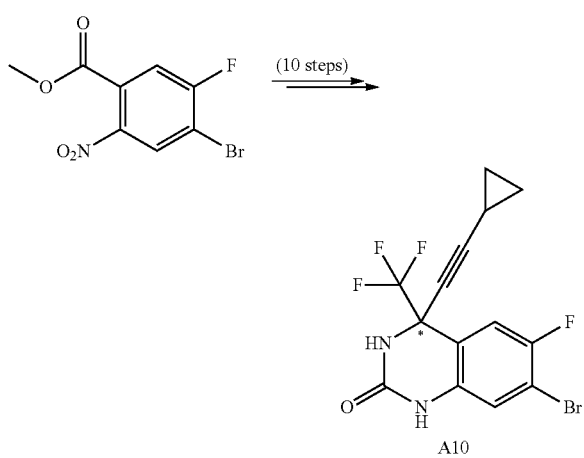

Step 1: methyl 2-amino-4-bromo-5-fluorobenzoate: To a solution of methyl 4-bromo-5-fluoro-2-nitrobenzoate (25 g, 90 mmol) in EtOH (375 mL) was added iron (40.2 g, 719 mmol) and $NH_4Cl$ (4.81 g, 90 mmol) in $H_2O$ (125 mL). The reaction mixture was stirred at 70° C. for 16 h. The reaction mixture was quenched with $H_2O$ (200 mL) and extracted with EtOAc (2×300 mL). The combined organics were washed with brine (100 mL), dried over $Na_2SO_4$, filtered and concentrated to afford the title compound, which was used directly without further purification.

Step 2: methyl 4-bromo-2-((tert-butoxycarbonyl)amino)-5-fluorobenzoate: To a solution of methyl 2-amino-4-bromo-5-fluorobenzoate (20 g, 81 mmol) was added di-tert-butyl dicarbonate (88 g, 403 mmol) and stirred at 120° C. for 16 h. The reaction mixture was concentrated and the resulting residue was diluted with PE and cooled to 0° C. The resulting precipitate was filtered and the solid was washed with 20 mL of cold PE and then, dried under reduced pressure to afford the title compound.

Step 3: tert-butyl (5-bromo-4-fluoro-2-(hydroxymethyl)phenyl)carbamate: To a stirred solution of methyl 4-bromo-2-((tert-butoxycarbonyl)amino)-5-fluorobenzoate (13 g, 37.3 mmol) in THF (130 mL) was added $LiAlH_4$ (1.417 g, 37.3 mmol) at 0° C. and the resulting mixture was stirred at 0° C. for 1 h. The mixture was quenched by adding water (2 mL) and then sat aq $Na_2SO_4$ sol and the resulting mixture was stirred for 10 min. The mixture was filtered and extracted with EtOAc (3×100 mL). The combined organic phase was washed with brine (100 mL), dried over anhydrous $Na_2SO_4$, filtered and concentrated. The residue was purified by prep MPLC ($SiO_2$, 1-20% EtOAc:PE) to give the title product. MS (ESI) m/z 320, 322 [M+1].

Step 4: tert-butyl (5-bromo-4-fluoro-2-formylphenyl)carbamate: To a solution of tert-butyl (5-bromo-4-fluoro-2-(hydroxymethyl)phenyl)carbamate (10 g, 31.2 mmol) in DCM (200 mL) was added DMP (26.5 g, 62.5 mmol) at 15° C. for 1 h. The mixture was diluted with DCM (100 mL), filtered and the organic phase was concentrated. The crude product was diluted with EtOAc (10 mL) and PE (200 mL), filtered and the organic phase was concentrated to give the title product.

Step 5: tert-butyl (5-bromo-4-fluoro-2-(2,2,2-trifluoro-1-hydroxyethyl)phenyl)carbamate: A solution of tert-butyl (5-bromo-4-fluoro-2-formylphenyl)carbamate (10 g, 31.4 mmol) and trimethyl(trifluoromethyl)silane (13.41 g, 94 mmol) in THF (200 mL) was added TBAF (1.644 g, 6.29 mmol) at 0° C. The mixture was stirred for 0.5 h at 20° C. Additional TBAF (8.22 g, 31.4 mmol) was added. The mixture was stirred at 20° C. for 0.5 h. HCl (1M, 20 mL) was added and the mixture was diluted with $H_2O$ (50 mL) and extracted with EtOAc (2×150 mL). The combined organic layer was washed with brine (2×50 mL) and dried over $Na_2SO_4$, filtered and concentrated. The residue was purified on flash chromatography ($SiO_2$, 5% EtOAc/PE) to give the title compound.

Step 6: tert-butyl (5-bromo-4-fluoro-2-(2,2,2-trifluoroacetyl)phenyl)carbamate: To a solution of tert-butyl (5-bromo-4-fluoro-2-(2,2,2-trifluoro-1-hydroxyethyl)phenyl)carbamate (6 g, 15.46 mmol) in DCM (60 mL) was added DMP (13.11 g, 30.9 mmol) at 20° C. for 1 h. The mixture was diluted with DCM, filtered and concentrated. The crude product was treated with EtOAc (5 mL) and PE (50 mL), filtered and concentrated to give the title product.

Step 7: 1-(2-amino-4-bromo-5-fluorophenyl)-2,2,2-trifluoroethanone: To a vial containing tert-butyl (5-bromo-4-fluoro-2-(2,2,2-trifluoroacetyl)phenyl)carbamate (5 g, 12.95 mmol) was added a 4M HCl solution in EtOAc (3 mL) and stirred for 1 h at 20° C. The solvent was removed under reduced pressure to give the crude product, which was purified by flash chromatography (SiO$_2$, 2% EtOAc/PE) to afford the title product.

Step 8: 7-bromo-6-fluoro-4-hydroxy-4-(trifluoromethyl)-3,4-dihydroquinazolin-2(H)-one: To a solution of 1-(2-amino-4-bromo-5-fluorophenyl)-2,2,2-trifluoroethanone (3 g, 10.49 mmol) in THF (30 mL) was added 4-dimethylaminopyridine (1.281 g, 10.49 mmol) and isocyanate trimethylsilane (3.14 g, 27.3 mmol). The mixture was stirred at 20° C. for 2 h. The reaction mixture was quenched with water (20 mL) and extracted with EtOAc (3×25 mL). The combined organic layer was dried over anhydrous Na$_2$SO$_4$, filtered and concentrated. The crude was purified by flash chromatography (SiO$_2$, 3-100% EtOAc:PE) to afford the title product.

Step 9: 7-bromo-6-fluoro-4-(trifluoromethyl)quinazolin-2(1H)-one: A solution of 7-bromo-6-fluoro-4-hydroxy-4-(trifluoromethyl)-3,4-dihydroquinazolin-2(1H)-one (1.8 g, 5.47 mmol) in toluene (20 mL) under N$_2$ was stirred at 120° C. for 23 h. The organic layer was concentrated to give the title product, which was used for the next step without further purification.

Step 10: (S)-7-bromo-4-(cyclopropylethynyl)-6-fluoro-4-(trifluoromethyl)-3,4-dihydroquinazolin-2(1H)-one AND (R)-7-bromo-4-(cyclopropylethynyl)-6-fluoro-4-(trifluoromethyl)-3,4-dihydroquinazolin-2(1H)-one: To a solution of ethynylcyclopropane (2.168 g, 32.8 mmol) in toluene (6 mL), LiHMDS (27.3 ml, 27.3 mmol) was added at -5° C. The mixture was heated at 85° C. for 35 min and then cooled to -5° C. A solution of 7-bromo-6-fluoro-4-(trifluoromethyl)quinazolin-2(1H)-one (1.7 g, 5.47 mmol) in THF (12 mL) was added, and the mixture was stirred for 2 h at 20° C. The reaction was quenched with a 1 M aq citric acid sol (5 mL) and diluted with EtOAc (35 mL). The organic layer was separated and dried over Na$_2$SO$_4$, filtered, and concentrated. The residue was purified by flash chromatography (SiO$_2$, 50% EtOAc/PE) to give the title product, which was resolved by prep SFC (Chiralpak AS-H, 40% MeOH (0.1% NH$_3$H$_2$O)/CO$_2$; 70 g/min; 40° C.; 100 bar) to provide: Isomer A10-A (faster eluting) and Isomer A10-B (slower eluting) MS (ESI) m/z 377, 379 [M+1] for both.

Intermediate A11, Isomer A11-A and Isomer A11-B: (S)-7-bromo-4-(cyclopropylethynyl)-4-(1,1-difluoroethyl)-3,4-dihydroquinazolin-2(H)-one and (R)-7-bromo-4-(cyclopropylethynyl)-4-(1,1-difluoroethyl)-3,4-dihydroquinazolin-2(H)-one

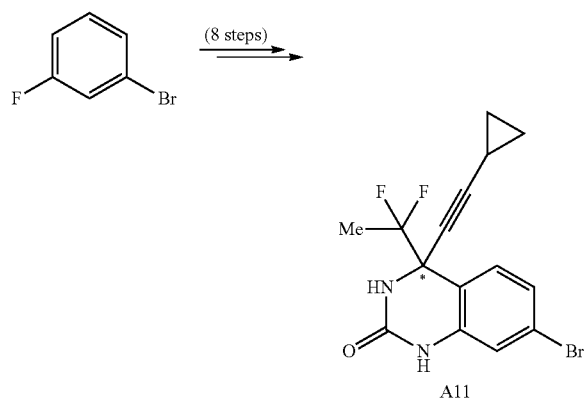

Step 1: (2-bromo-6-fluorophenyl)trimethylsilane: To a solution of 1-bromo-3-fluorobenzene (50 g, 286 mmol) and TMSCl (73.0 mL, 571 mmol) in THF (450 mL) was added LDA (286 mL, 571 mmol) at -70° C. The reaction was stirred at -70° C. for 2 h. The reaction was hydrolyzed with aq 1 M H$_2$SO$_4$ sol. The yellow organic phase was separated, and the water phase was extracted with EtOAc. The combined organic phase was concentrated to give the title compound, which was used without further purification.

Step 2: 1-(4-bromo-2-fluoro-3-(trimethylsilyl)phenyl)-2,2-difluoropropan-1-one: To a solution of 2,2,6,6-tetramethylpiperidine (18.86 g, 134 mmol) in THF (125 mL) was added nBuLi (53.4 mL, 134 mmol) at -20° C. After 30 min of stirring at -20° C., the mixture was cooled to -70° C., and a solution of (2-bromo-6-fluorophenyl)trimethylsilane (30 g, 121 mmol) in THF (35 mL) was added. After 1 h of stirring at -70° C., ethyl 2,2-difluoropropanoate (18.44 g, 134 mmol) was added dropwise. The mixture was then allowed to warm to 20° C. and stirred at 20° C. for another 1 h. Then, sat aq NH$_4$Cl sol (300 mL) was added, and the mixture was extracted with EtOAc (3×300 mL). The combined organic layer was washed with brine (300 mL), dried over Na$_2$SO$_4$, filtered and concentrated to give the title compound, which was used without further purification.

Step 3: 1-(4-bromo-2-fluorophenyl)-2,2-difluoropropan-1-one: To a solution of 1-(4-bromo-2-fluoro-3-(trimethylsilyl)phenyl)-2,2-difluoropropan-1-one (45 g, 133 mmol) in THF (200 mL) was added TBAF (34.7 g, 133 mmol) at 20° C. The reaction was stirred at 20° C. for 0.5 h. The reaction mixture was concentrated and the resulting residue was purified by flash chromatography (SiO$_2$, 0-5% EtOAc/PE) to afford the title compound.

Step 4: 1-(4-bromo-2-((4-methoxybenzyl)amino)phenyl)-2,2-difluoropropan-1-one: To a solution of 1-(4-bromo-2-fluorophenyl)-2,2-difluoropropan-1-one (20 g, 74.9 mmol) in toluene (200 mL) were added (4-methoxyphenyl)methanamine (20.55 g, 150 mmol) and K$_2$CO$_3$ (12.42 g, 90 mmol). The reaction was stirred at 115° C. for 2 h. The reaction was concentrated and the residue was purified by flash chromatography (SiO$_2$, 0-5% EtOAc/PE) to give the title product.

Step 5: 7-bromo-4-(1,1-difluoroethyl)-4-hydroxy-1-(4-methoxybenzyl)-3,4-dihydroquinazolin-2(1H)-one: To a solution of 1-(4-bromo-2-((4-methoxybenzyl)amino)phenyl)-2,2-difluoropropan-1-one (20 g, 52.1 mmol) in AcOH (400 mL) was added sodium cyanate (33.8 g, 521 mmol). The reaction was stirred at 110° C. for 16 h. The reaction pH was adjusted to pH=8 with sat aq NaHCO$_3$ sol and extracted with EtOAc (3×500 mL). The combined organic layer was washed with brine (500 mL), dried over Na$_2$SO$_4$, filtered and concentrated. The crude product was purified by flash chromatography (SiO$_2$, 0-25% EtOAc/PE) to give the title compound.

Step 6: 7-bromo-4-(1,1-difluoroethyl)-1-(4-methoxybenzyl)quinazolin-2(1H)-one: To a solution of 7-bromo-4-(1,1-difluoroethyl)-4-hydroxy-1-(4-methoxybenzyl)-3,4-dihydroquinazolin-2(1H)-one (10 g, 23.41 mmol) in MeCN (200 mL) was added phosphorus pentoxide (3.99 g, 28.1 mmol). The reaction was stirred at 90° C. under N$_2$ for 3 h. The reaction pH was adjusted with sat aq NaHCO$_3$ sol to pH=8 and extracted with EtOAc (3×500 mL). The combined organic layer was washed with brine (500 mL), dried over Na$_2$SO$_4$, filtered and concentrated to give the title product, which was used in the next step without further purification.

Step 7: 7-bromo-4-(cyclopropylethynyl)-4-(1,1-difluoroethyl)-1-(4-methoxybenzyl)-3,4-dihydroquinazolin-2(1H)-one: To a solution of ethynylcyclopropane (4.36 g, 66.0 mmol) in toluene (50 mL) was added LiHMDS (55.0 mL, 55.0 mmol) at 0° C. The reaction was stirred at 85° C. for 15 min. Then, a solution of 7-bromo-4-(1,1-difluoroethyl)-1-(4-methoxybenzyl) quinazolin-2(1H)-one (9 g, 11.00 mmol) in THF (50.0 mL) was added to the reaction at 0° C. The reaction was stirred at 15° C. for 0.5 h. The reaction was quenched with sat aq NH₄Cl sol (100 mL). The residue was extracted with EtOAc (3×100 mL). The combined organic layer was washed with brine (100 mL), dried over Na₂SO₄, filtered and concentrated. The crude product was purified by flash chromatography (SiO₂, 0-25% EtOAc/PE) to afford the title compound.

Step 8: (S)-7-bromo-4-(cyclopropylethynyl)-4-(1,1-difluoroethyl)-3,4-dihydroquinazolin-2(H)-one AND (R)-7-bromo-4-(cyclopropylethynyl)-4-(1,1-difluoroethyl)-3,4-dihydroquinazolin-2(H)-one: To a mixture of 7-bromo-4-(cyclopropylethynyl)-4-(1,1-difluoroethyl)-1-(4-methoxybenzyl)-3,4-dihydroquinazolin-2(1H)-one (3 g, 6.31 mmol) in MeCN (40 mL) and water (15 mL) was added CAN (17.30 g, 31.6 mmol). The reaction was stirred at 15° C. for 2 h. The reaction was extracted with EtOAc (3×50 mL). The combined organic layer was washed with brine (50 mL), dried over Na₂SO₄, filtered and concentrated. The crude product was purified by flash chromatography (SiO₂, 0-25% EtOAc/PE) to give the title product. The racemic mixture was resolved by prep SFC (DAICEL CHIRALPAK AD, 45% MeOH (0.1% NH₃H₂O)/CO₂, 65 mL/min, 40° C., 100 bar) to afford: Isomer A11-A (faster eluting) and Isomer A11-B (slower eluting) MS (ESI) m/z 355, 357 [M+1] for both.

Intermediate A12: 7-bromo-4-(cyclopropylethynyl)-4-(1,1-difluoroethyl)-6-fluoro-3,4-dihydroquinazolin-2(1H)-one

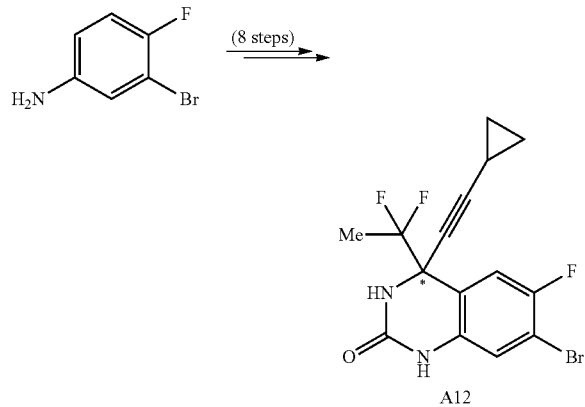

A12

Step 1: 5-bromo-4-fluoro-2-iodoaniline: To a solution of 3-bromo-4-fluoroaniline (100 g, 526 mmol) in AcOH (1 L) was added NIS (101 g, 447 mmol) at 25° C. The mixture was stirred for 16 h at 25° C. The reaction mixture was concentrated and the resulting crude was then dissolved in water (100 mL) and extracted with EtOAc (350 mL×2). The combined organic layer was washed with H₂O (2×150 mL), sat aq NaHCO₃ sol (250 mL) and brine (50 mL), dried over Na₂SO₄, filtered and concentrated. The resulting crude was purified by flash chromphotography (SiO₂, 0-2% EtOAc/PE) to give the title compound.

Step 2: tert-butyl (5-bromo-4-fluoro-2-iodophenyl)carbamate: To a stirred solution of 5-bromo-4-fluoro-2-iodoaniline (60 g, 190 mmol) in DCM (80 mL) was added DMAP (1.160 g, 9.50 mmol). Then, Et₃N (2.65 mL, 18.99 mmol) and di-tert-butyl dicarbonate (62.2 g, 285 mmol) were added. The mixture was stirred at 25° C. for 4 h. The reaction mixture was diluted with DCM (500 mL), washed with water (2×100 mL), brine (50 mL), dried over Na₂SO₄, filtered and concentrated to give the title compound, which was used without further purification.

Step 3: tert-butyl (5-bromo-4-fluoro-2-iodophenyl)carbamate: To a stirred solution of tert-butyl (5-bromo-4-fluoro-2-iodophenyl)carbamate (90 g, 122 mmol) in MeOH (300 mL) was added K₂CO₃ (135 g, 976 mmol). The mixture was stirred at 30° C. for 2 h. The reaction mixture was diluted with water (500 mL), and then, extracted with EtOAc (2×300 mL). The combined organic layer was combined and washed with brine (100 mL), dried over Na₂SO₄, filtered and concentrated. The resulting crude was purified by flash chromatography (SiO₂; 1% EtOAc/PE) to give the title compound.

Step 4: tert-butyl (5-bromo-2-(2,2-difluoropropanoyl)-4-fluorophenyl)carbamate: To a mixture of tert-butyl (5-bromo-4-fluoro-2-iodophenyl)carbamate (20 g, 33.7 mmol) and ethyl 2,2-difluoropropanoate (12.65 mL, 101 mmol) in THF (250 mL) was added dropwise isopropylmagnesium chloride-lithium chloride complex (64.7 mL, 84 mmol) at −70° C. over 30 min. The reaction mixture was stirred at −70° C. for 1 h. The mixture was quenched with sat aq NH₄Cl sol (45 mL) and water (45 mL), and then extracted with EtOAc (2×80 mL). The combined organic layer was washed with brine (30 mL), dried over Na₂SO₄, filtered and concentrated to give the title compound, which was used without further purification.

Step 5: 1-(2-amino-4-bromo-5-fluorophenyl)-2,2-difluoropropan-1-one: A mixture of tert-butyl (5-bromo-2-(2,2-difluoropropanoyl)-4-fluorophenyl)carbamate (45 g, 118 mmol) in a solution of HCl in EtOAc (4 M, 200 mL) at 25° C. was stirred for 1 h. The formed precipitate was treated with EtOAc (400 mL) and concentrated to give the title compound.

Step 6: 7-bromo-4-(1,1-difluoroethyl)-6-fluoro-4-hydroxy-3,4-dihydroquinazolin-2(H)-one: To a solution of 1-(2-amino-4-bromo-5-fluorophenyl)-2,2-difluoropropan-1-one (6.7 g, 23.75 mmol) in THF (67 mL) was added DMAP (2.90 g, 23.75 mmol) and (trimethylsilyl)isocyanate (8.36 mL, 61.8 mmol). The resulting mixture was stirred at 25° C. for 2 h. The reaction mixture was quenched with H₂O (30 mL) and extracted into EtOAc (3×55 mL). The combined organic layer was dried over Na₂SO₄, filtered and concentrated. The crude was dissolved in THF (25 mL) and aq HCl (1M, 25 mL) and stirred at 25° C. for 2 h. The reaction mixture was concentrated and then purified by flash chromatography (SiO₂; 30~80% EtOAc/PE) to give the title compound.

Step 7: 7-bromo-4-(1,1-difluoroethyl)-6-fluoroquinazolin-2(H)-one: A mixture of 7-bromo-4-(1,1-difluoroethyl)-6-fluoro-4-hydroxy-3,4-dihydroquinazolin-2(1H)-one (2 g, 6.15 mmol) in toluene (50 mL) was stirred under nitrogen at 140° C. for 16 h. The reaction mixture was concentrated to give the title product, which was used without further purification.

Step 8: 7-bromo-4-(cyclopropylethynyl)-4-(1,1-difluoroethyl)-6-fluoro-3,4-dihydroquinazolin-2(1H)-one: To a solution of ethynylcyclopropane (3.31 mL, 39.1 mmol) in toluene (10 mL), LiHMDS (25.05 mL, 32.6 mmol) was added at −5° C. The mixture was heated at 85° C. for 35 min and then cooled to −5° C. A solution of 7-bromo-4-(1,1-difluoroethyl)-6-fluoroquinazolin-2(1H)-one (2 g, 6.51 mmol) in THF (20 mL) was added, and the mixture was stirred for 100 min at 25° C. The reaction was quenched by the addition of sat aq NH₄Cl sol (45 mL) and extracted with EtOAc (2×55 mL). The organic layers were combined and dried over Na₂SO₄, filtered, and concentrated to give the title compound, which was used without further purification. MS (ESI) m/z 373.0, 375.0 [M+1].

Intermediates: Section B

Intermediate B01: (S)-4-(cyclopropylethynyl)-7-(4,4,5,5-tetramethyl-1,3,2-dioxaborolan-2-yl)-4-(trifluoromethyl)-3,4-dihydroquinazolin-2(1H)-one

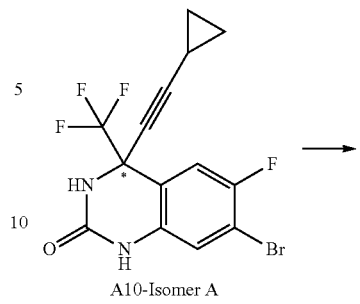

A10-Isomer A

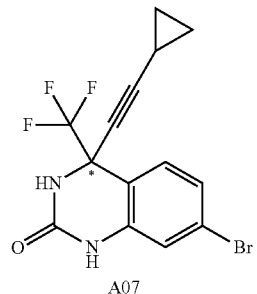

A07

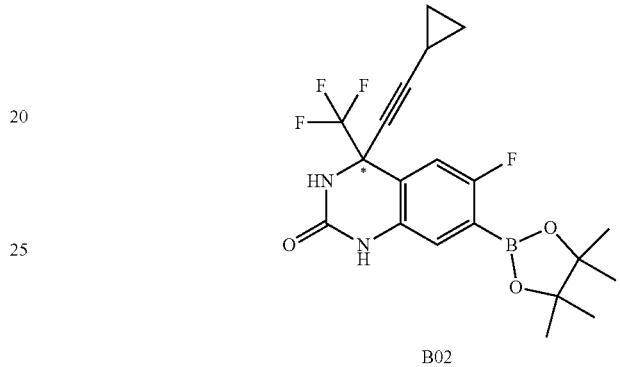

B02

Intermediate B03: (S)-7-(chloromethyl)-4-(cyclopropylethynyl)-4-(trifluoromethyl)-3,4-dihydroquinazolin-2(1H)-one

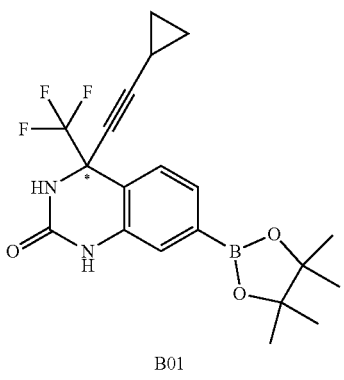

B01

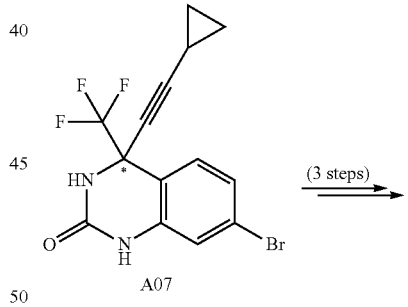

A07

A solution of intermediate A07, BisPin (255 mg, 1.002 mmol) and KOAc (246 mg, 2.506 mmol) in 1,4-dioxane (7 mL) was added Pd(PPh₃)₂Cl₂ (29.3 mg, 0.042 mmol) under nitrogen, the mixture was stirred at 80° C. for 16 h under nitrogen. The mixture was diluted with water (30 mL) and EtOAc (30 mL), filtered and extracted with EtOAc (3×30 mL). The combined organic layers were dried over Na₂SO₄, filtered and concentrated. The residue was purified by flash chromatography (SiO₂, 30% EtOAc/PE) to afford the title compound. MS (ESI) m/z 407 [M+1].

Intermediate B02 was prepared using a procedure analogous to that used for making Intermediate B01 except that Intermediate A07 was replaced by Intermediate A10-Isomer A.

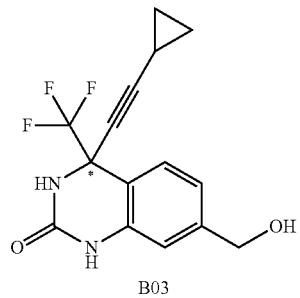

B03

Step 1: (S)-4-(cyclopropylethynyl)-4-(trifluoromethyl)-7-vinyl-3,4-dihydroquinazolin-2(H)-one: A solution of inter mediate A07 (6 g, 16.71 mmol) in 1,4-dioxane (120 mL) and water (12 mL) was added potassium trifluoro(vinyl)borate (3.36 g, 25.06 mmol), K₂CO₃ (6.93 g, 50.1 mmol), PdCl₂(dppf) (1.222 g, 1.671 mmol) under N₂ and the resulting mixture was stirred for 1 h at 100° C. under N₂. The reaction was cool down and then poured into H₂O (500 mL), extracted with EtOAc (3×200 mL). The combined organic layer was dried over Na₂SO₄, filtered, concentrated, and purified by flash chromatography (SiO₂, 0-30% EtOAc/PE) to afford the title compound.

Step 2: (S)-4-(cyclopropylethynyl)-2-oxo-4-(trifluoromethyl)-1,2,3,4-tetrahydroquinazoline-7-carbaldehyde: To a stirred solution of (S)-4-(cyclopropylethynyl)-4-(trifluoromethyl)-7-vinyl-3,4-dihydroquinazolin-2(1H)-one (5.49 g, 17.92 mmol) in 1,4-dioxane (100 mL) and H₂O (50 mL) was added 2,6-lutidine (3.84 g, 35.8 mmol), potassium osmate (VI) dihydrate (1.321 g, 3.58 mmol). The resulting mixture was stirred for 10 min and then, sodium periodate (11.50 g, 53.8 mmol) was added and the resulting mixture was stirred at 25° C. for 1 h. The reaction mixture was quenched with H₂O (500 mL) and extracted with EtOAc (3×300 mL). The combined organics were washed with brine (90 mL), dried over Na₂SO₄, filtered and concentrated, and then, purified by flash chromatography (SiO₂, 0-30% EtOAc/PE) to afford the title compound.

Step 3: (S)-4-(cyclopropylethynyl)-7-(hydroxymethyl)-4-(trifluoromethyl)-3,4-dihydroquinazolin-2(1H)-one: To a solution of (S)-4-(cyclopropylethynyl)-2-oxo-4-(trifluoromethyl)-1,2,3,4-tetrahydroquinazoline-7-carbaldehyde (4.6 g, 14.92 mmol) in MeOH (50 mL) was added NaBH₄ (0.226 g, 5.97 mmol) at 25° C. under N₂ and the mixture was stirred at this temperature for 10 min. Water (250 mL) was added to the mixture and then extracted with EtOAc (3×150 mL). The combined organic phase was washed with brine (450 mL) and dried over Na₂SO₄, filtered and concentrated. The crude product was purified by pre-HPLC (water: MeCN with 0.1% TFA) to give the title compound.

Intermediate B04, B04-Isomer A and B04-Isomer B: (S)-6-chloro-4-(cyclopropylethynyl)-7-(hydroxymethyl)-1-(4-methoxybenzyl)-4-(trifluoromethyl)-3,4-dihydroquinazolin-2(1H)-one and (R)-6-chloro-4-(cyclopropylethynyl)-7-(hydroxymethyl)-1-(4-methoxybenzyl)-4-(trifluoromethyl)-3,4-dihydroquinazolin-2(1H)-one

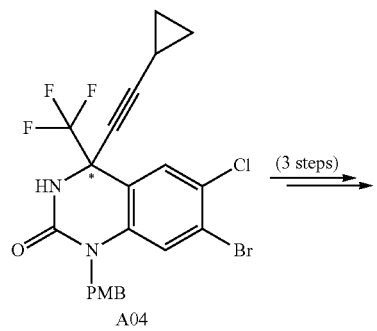

A04

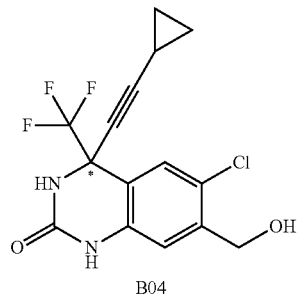

B04

Step 1: 6-chloro-4-(cyclopropylethynyl)-1-(4-methoxybenzyl)-4-(trifluoromethyl)-7-vinyl-3,4-dihydroquinazolin-2(1H)-one: To a solution of Intermediate A04 (14 g, 27.3 mmol) and potassium trifluoro(vinyl)borate (5.48 g, 40.9 mmol) in 1,4-dioxane (140 mL) and water (14 mL) was added K₂CO₃ (11.30 g, 82 mmol) and PdCl₂(dppf) (1.994 g, 2.73 mmol), then the reaction mixture was stirred at 100° C. for 3 h under N₂. The reaction was concentrated and purified by flash chromatography (SiO₂; 0-20% EtOAc/PE) to give the title compound.

Step 2: 6-chloro-4-(cyclopropylethynyl)-7-(hydroxymethyl)-1-(4-methoxybenzyl)-4-(trifluoromethyl)-3,4-dihydroquinazolin-2(1H)-one: A solution of 6-chloro-4-(cyclopropylethynyl)-1-(4-methoxybenzyl)-4-(trifluoromethyl)-7-vinyl-3,4-dihydroquinazolin-2(1H)-one (8.2 g, 17.79 mmol) in MeOH (30 mL) and DCM (150 mL) was bubbled with ozone (0.854 g, 17.79 mmol) for 0.5 h at −60° C. NaBH(OAc)₃ (22.63 g, 107 mmol) was added and the reaction mixture was stirred for 0.5 h at 20° C. The reaction was dissolved in water (100 mL) and extracted with DCM (3×100 mL). The combined organic layer was washed with brine (100 mL), dried over Na₂SO₄, filtered and concentrated to give the title product, which was used directly for the next step without purification.

Step 3: (S)-6-chloro-4-(cyclopropylethynyl)-7-(hydroxymethyl)-4-(trifluoromethyl)-3,4-dihydroquinazolin-2(1H)-one AND (R)-6-chloro-4-(cyclopropylethynyl)-7-(hydroxymethyl)-4-(trifluoromethyl)-3,4-dihydroquinazolin-2(1H)-one: To a solution of 6-chloro-4-(cyclopropylethynyl)-7-(hydroxymethyl)-1-(4-methoxybenzyl)-4-(trifluoromethyl)-3,4-dihydroquinazolin-2(1H)-one (8.5 g, 18.28 mmol) in MeCN (200 mL) and H₂O (70 mL) was added CAN (50.1 g, 91 mmol). The mixture was stirred for 16 h at 20° C. The reaction was dissolved in H₂O (100 mL) and extracted with EtOAc (3×150 mL). The combined organic layer was washed with brine (200 mL), dried over Na₂SO₄, filtered and concentrated. The crude product was purified by prep-HPLC (water/MeCN with 0.1% TFA) to give the title compound, which was resolved by SFC (Chiralpak AD, 30% EtOH/CO₂, 200 g/min, 40° C., 100 bar) to give: Isomer B04-A (faster eluting): ¹H-NMR (400 MHz, MeOH-d₄) δ ppm 7.44 (s, 1H), 7.14 (s, 1H), 4.71-4.60 (m, 2H), 1.53-1.38 (m, 1H), 1.00-0.85 (m, 2H), 0.83-0.70 (m, 2H); and Isomer B04-B (slower eluting): ¹H-NMR (400 MHz, MeOH-d₄) δ ppm 7.44 (s, 1H), 7.14 (s, 1H), 4.71-4.62 (m, 2H), 1.45 (tt, J=8.3, 4.9 Hz, 1H), 0.99-0.85 (m, 2H), 0.82-0.69 (m, 2H).

| Intermediate |
|---|
| B05 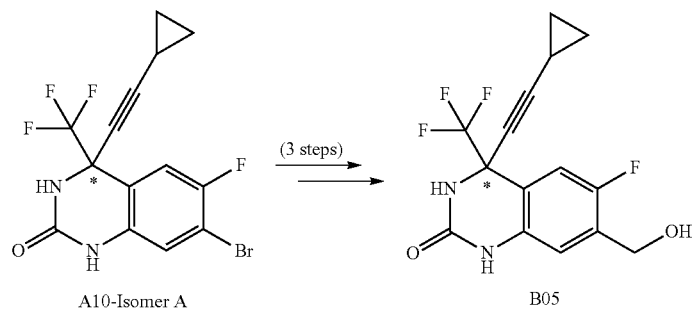 |
| B06 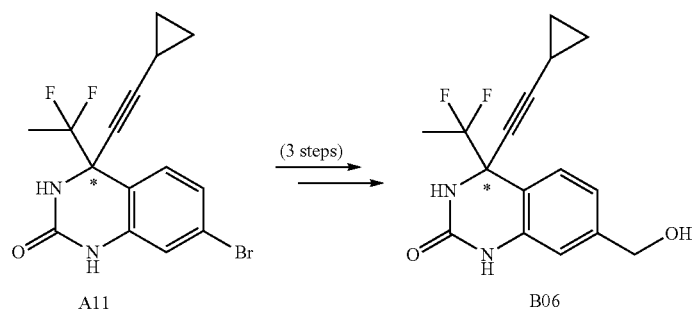 |
| B07 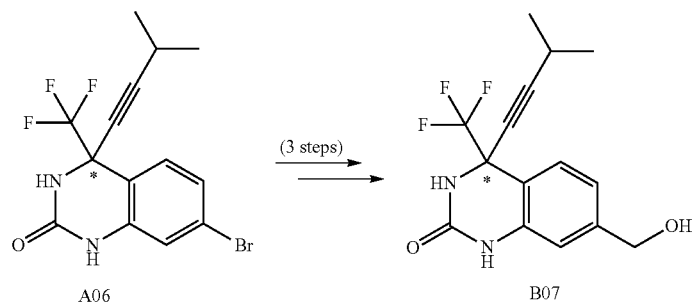 |
| B08 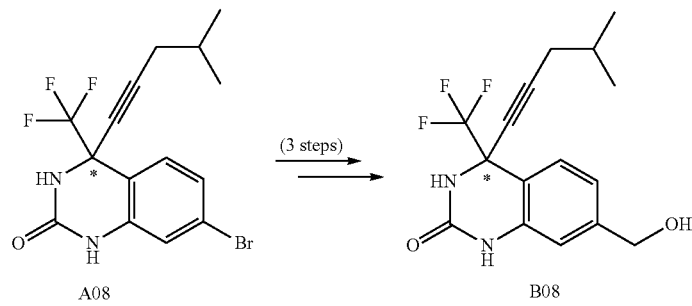 |
| B09 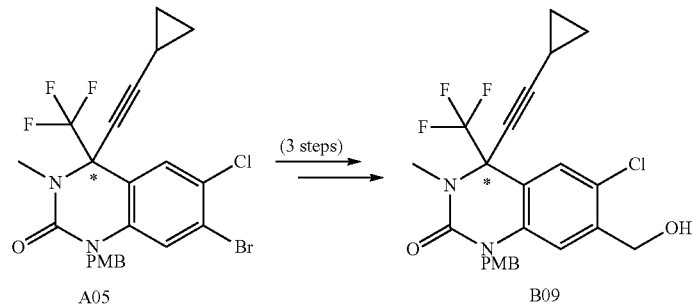 |

The following intermediates were prepared using a procedure analogous to that used for making B03 using the noted starting intermediate in place of A07.

Intermediate B10: 6-chloro-4-(cyclopropylethynyl)-7-(hydroxymethyl)-3-methyl-4-(trifluoromethyl)-3,4-dihydroquinazolin-2(1H)-one

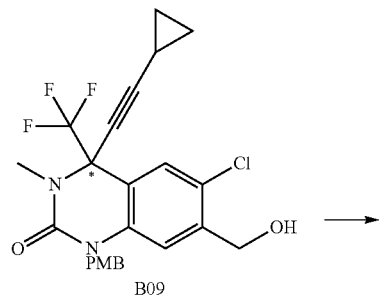

B09

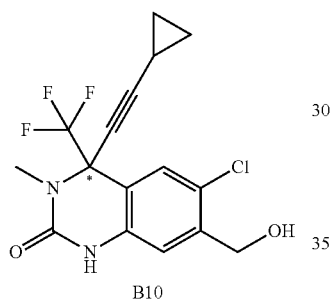

B10

To a solution of intermediate B09 (100 mg, 0.209 mmol) in MeCN (1.5 mL) and water (0.5 mL) was added CAN (572 mg, 1.044 mmol). The reaction was stirred at 20° C. for 20 h. The reaction mixture was diluted with water (5 mL), and then extracted with EtOAc (2×5 mL). The combined organic layer was washed with brine (5 mL), dried over Na₂SO₄, filtered and concentrated. The resulting residue was purified by prep-TLC (SiO₂, 50% EtOAc/PE) to afford the title compound.

Intermediate B11: (S)-7-(chloromethyl)-4-(cyclopropylethynyl)-4-(trifluoromethyl)-3,4-dihydroquinazolin-2(1H)-one

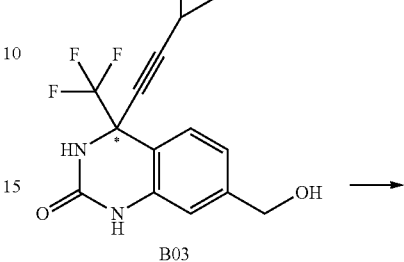

B03

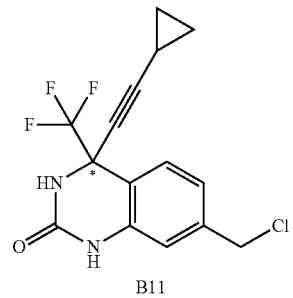

B11

To a solution of intermediate B03 (300 mg, 0.967 mmol) in anhydrous DCM (3 mL) was added DIPEA (1.013 mL, 5.80 mmol) and MsCl (0.151 mL, 1.934 mmol). The reaction was stirred at 20° C. for 16 h. The reaction was diluted with water (20 ml) and extracted with DCM (3×20 ml). The combined organic extracts were dried over Na₂SO₄, filtered and concentrated. The crude product was purified by prep-TLC (SiO₂, 50% EtOAc/PE) to afford the title compound.

The following intermediates were prepared using a procedure analogous to that used for making B11 using the noted starting intermediate in place of B03.

| Intermediate | |
|---|---|
| B12 | 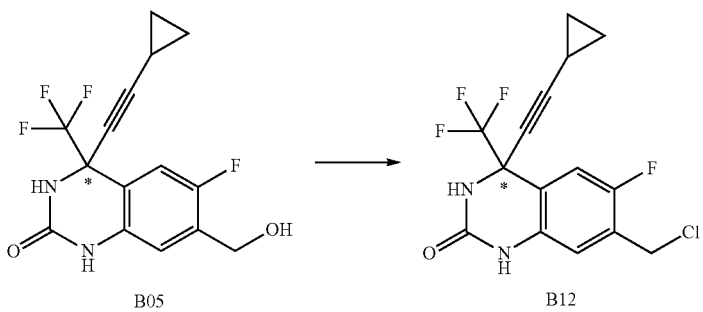 |

-continued
| Intermediate | |
|---|---|
| B13 | 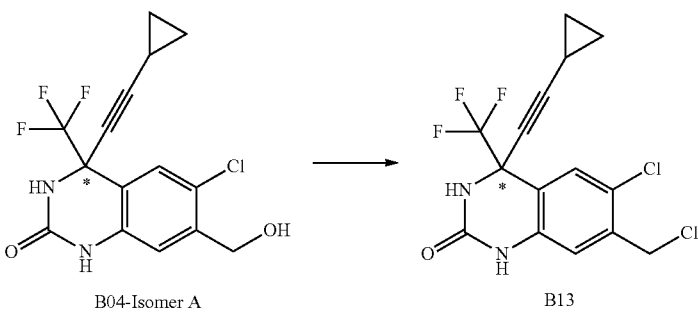 |
| B14 | 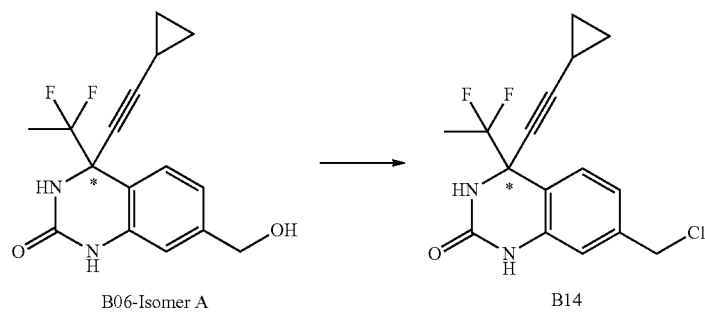 |
| B15 | 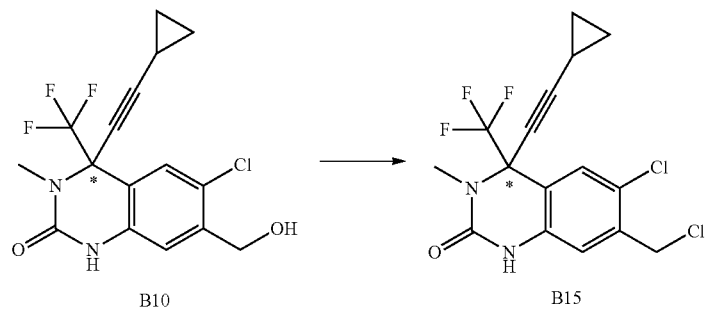 |
| B16 | 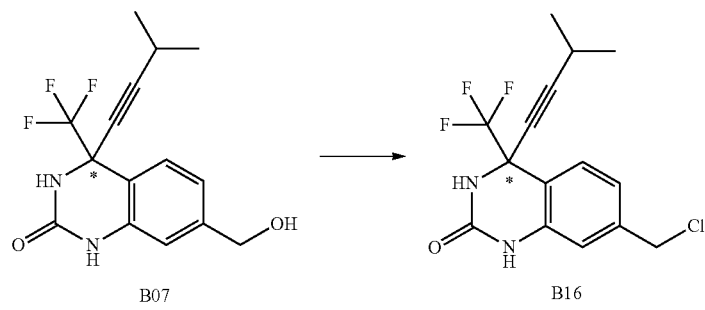 |
| B17 | 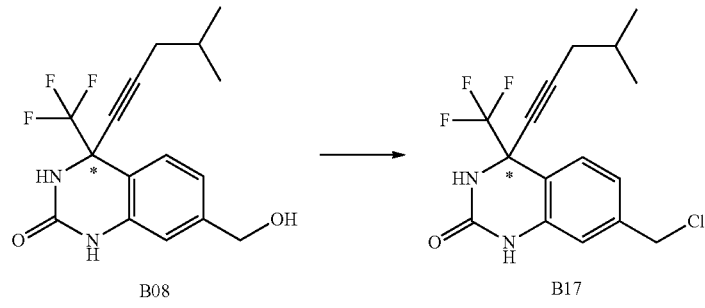 |

Intermediate B18: (S)-6-bromo-7-(chloromethyl)-4-(cyclopropylethynyl)-4-(trifluoromethyl)-3,4-dihydroquinazolin-2(1H)-one

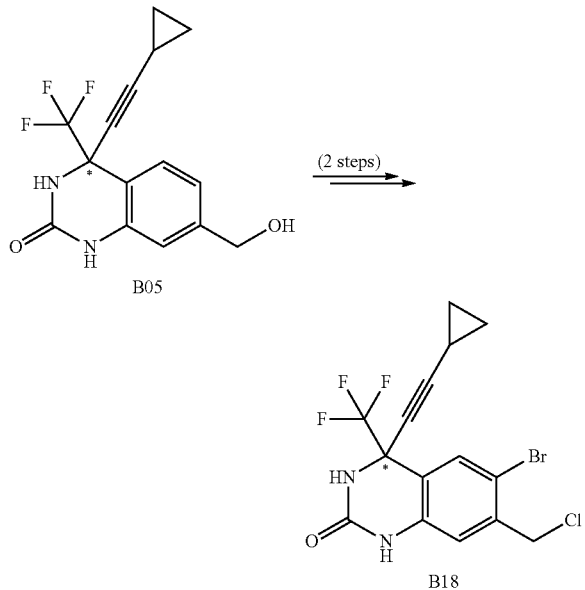

Step 1: (S)-6-bromo-4-(cyclopropylethynyl)-7-(hydroxymethyl)-4-(trifluoromethyl)-3,4-dihydroquinazolin-2(1H)-one: To a stirred solution of intermediate B05 (150 mg, 0.46 mmol) (527 mg, 1.698 mmol) in MeCN (8.5 mL), NBS (333 mg, 1.87 mmol) was added and stirred for 16 h at 25° C. and then stirred at 40° C. for additional 3 h. The reaction mixture was cooled down to room temperature and concentrated. The resulting crude was purified by flash chromatography (SiO₂, 0-100% (1:3 EtOH:EtOAc):hexanes) to give the title compound.

Step 2: (S)-6-bromo-7-(chloromethyl)-4-(cyclopropylethynyl)-4-(trifluoromethyl)-3,4-dihydroquinazolin-2(1H)-one: To a solution of (S)-6-bromo-4-(cyclopropylethynyl)-7-(hydroxymethyl)-4-(trifluoromethyl)-3,4-dihydroquinazolin-2(1H)-one (205.5 mg, 0.528 mmol) in DCE (5.3 mlL) and thionyl chloride (771 µL, 10.56 mmol) was added. The resulting mixture was stirred at 60° C. for 16 h. The reaction mixture was concentrated and azeotroped with Et₂O to give the title compound, which was used without further purification.

Intermediate B19: (S)-6-chloro-7-(chloromethyl)-4-(cyclopropylethynyl)-4-(1,1-difluoroethyl)-3,4-dihydroquinazolin-2(1H)-one

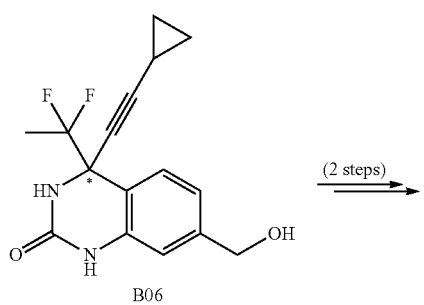

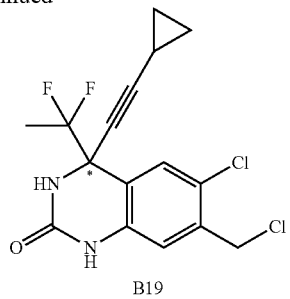

Step 1: (S)-6-chloro-4-(cyclopropylethynyl)-4-(1,1-difluoroethyl)-7-(hydroxymethyl)-3,4-dihydroquinazolin-2(1H)-one: To a solution of intermediate B06 (260 mg, 0.849 mmol) in DMF (5 mL) was added NCS (113 mg, 0.849 mmol). The resulting reaction mixture was stirred at 40° C. for 16 h, and then diluted with EtOAc and washed with H₂O, dried over MgSO₄, filtered and concentrated to give the title compound, which was used without further purification.

Step 2: (S)-6-chloro-7-(chloromethyl)-4-(cyclopropylethynyl)-4-(1,1-difluoroethyl)-3,4-dihydroquinazolin-2(1H)-one: To a solution of (S)-6-chloro-4-(cyclopropylethynyl)-4-(1,1-difluoroethyl)-7-(hydroxymethyl)-3,4-dihydroquinazolin-2(1H)-one (289 mg, 0.848 mmol) in anhydrous DCE (8.5 mL) was added thionyl chloride (1.2 mL, 16.96 mmol). The reaction was stirred at 60° C. for 90 min. The reaction mixture was concentrated and azeotroped with Et₂O to give the title compound, which was used without further purification.

Intermediate B20: (S)-7-(chloromethyl)-4-(cyclopropylethynyl)-6,8-difluoro-4-(trifluoromethyl)-3,4-dihydroquinazolin-2(1H)-one

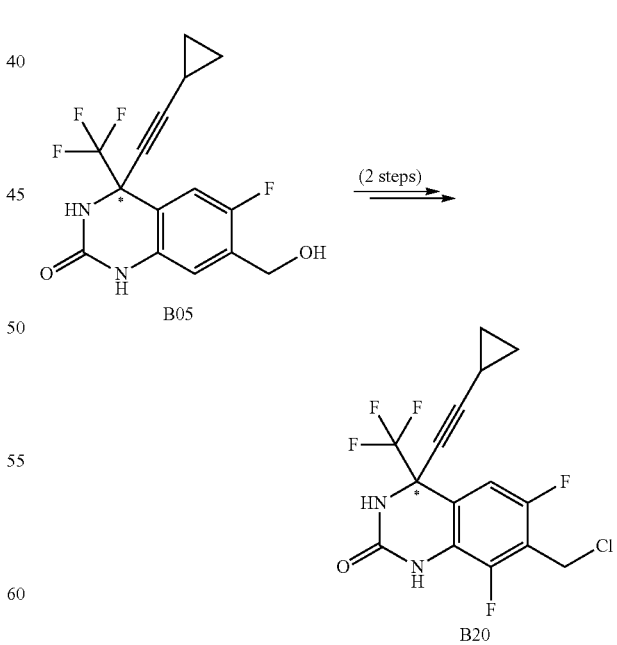

Step 1: (S)-4-(cyclopropylethynyl)-6,8-difluoro-7-(hydroxymethyl)-4-(trifluoromethyl)-3,4-dihydroquinazolin-2(1H)-one: To a solution of intermediate B05 (20 mg, 0.061 mmol) in anhydrous MeCN (0.6 mL) was added 1-fluoro- 4-methyl-1,4-diazabicyclo[2.2.2]octane-1,4-diium tetrafluoroborate (19.49 mg, 0.061 mmol). The resulting mixture was stirred at 50° C. for 16 h. The reaction was then purified by HPLC (water/MeCN with 0.1% TFA) to give the title product.

Step 2: (S)-7-(chloromethyl)-4-(cyclopropylethynyl)-6,8-difluoro-4-(trifluoromethyl)-3,4-dihydroquinazolin-2(1H)-one: To a solution of (S)-4-(cyclopropylethynyl)-6,8-difluoro-7-(hydroxymethyl)-4-(trifluoromethyl)-3,4-dihydroquinazolin-2(1H)-one (10 mg, 0.061 mmol) in anhydrous DCM (0.5 ml) was added thionyl chloride (500 µL, 6.85 mmol). The resulting mixture was stirred at 40° C. for 16 h. The reaction was concentrated to give the title compound, which was used without further purification. MS (ESI) m/z 364 [M+1].

Intermediate B21: (S)-4-(cyclopropylethynyl)-7-(hydroxymethyl)-1-(4-methoxybenzyl)-4-(trifluoromethyl)-3,4-dihydroquinazolin-2(1H)-one

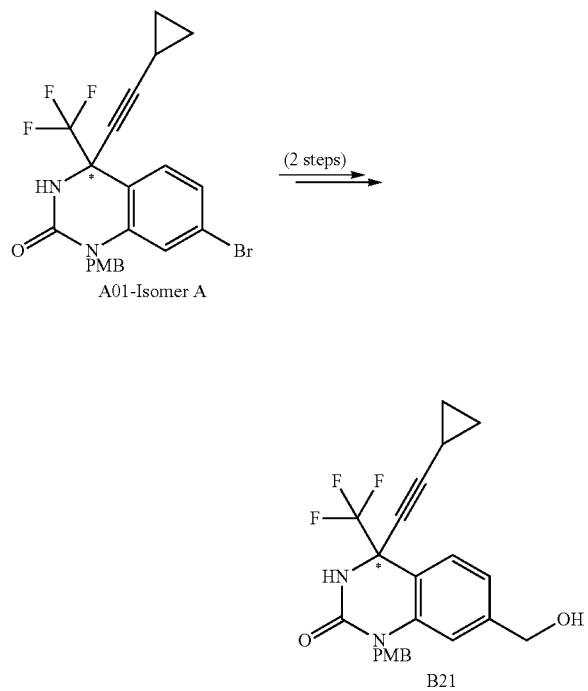

Step 1: (S)-4-(cyclopropylethynyl)-1-(4-methoxybenzyl)-7-(((4-methoxybenzyl)oxy)methyl)-4-(trifluoromethyl)-3,4-dihydroquinazolin-2(1H)-one: A mixture of intermediate A01-Isomer A (1.6 g, 3.34 mmol), potassium (4-methoxy) benzyloxy methyltrifluoroborate (1.809 g, 7.01 mmol) and PdCl₂(dppf) (0.122 g, 0.167 mmol) in 1,4-dioxane (16.7 mL) was flashed with N₂, and then treated with a 2 M Cs₂CO₃ aq sol (6.68 mL, 20.03 mmol). The resulting mixture was irradiated at 130° C. in the microwave oven for 30 min, and then filtered through Celited funnel. The filter cake was rinsed with EtOAc and water. The organic layer was separated and concentrated and the residue was purified by flash chromatography (SiO₂, 0-100% EtOAc/hexane) to afford the title compound.

Step 2: (S)-4-(cyclopropylethynyl)-7-(hydroxymethyl)-1-(4-methoxybenzyl)-4-(trifluoromethyl)-3,4-dihydroquinazolin-2(1H)-one: To a solution of (S)-4-(cyclopropylethynyl)-1-(4-methoxybenzyl)-7-(((4-methoxy benzyl)oxy) methyl)-4-(trifluoromethyl)-3,4-dihydroquinazolin-2(1H)-one (540 mg, 0.981 mmol) in DCM (20 mL) was added TFA (1 mL, 12.98 mmol). The resulting solution was stirred at 25° C. for 1 h. The reaction mixture was diluted with DCM (100 mL), then neutralized with sat aq NaHCO₃ sol. The mixture was extracted with DCM. The organic layer was concentrated and the residue was purified by flash chromatography (SiO₂, 0-100% EtOAc/hexane) to afford the title compound.

Intermediate B22 was prepared using a procedure analogous to that used for making B03 except that Intermediate A07 was replaced by Intermediate A12.

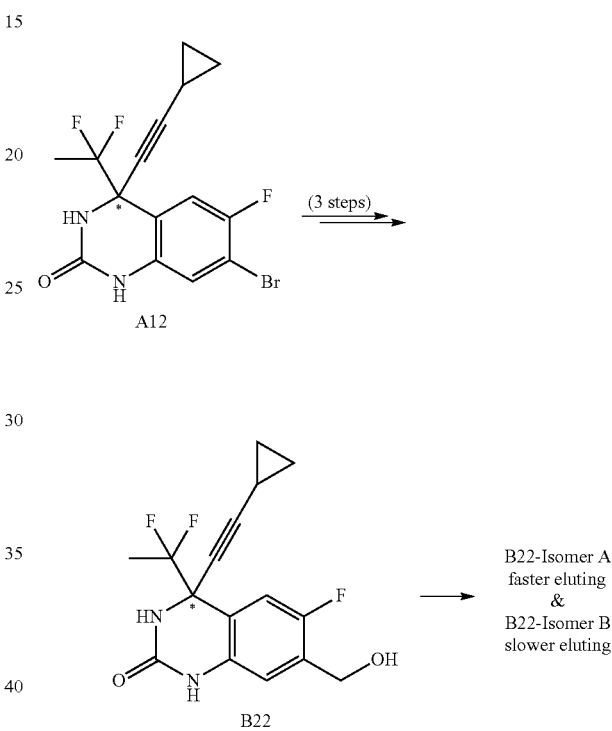

The racemic B22 product was separated by SFC (Chiralpak AD; 42% iPrOH (0.1% NH₃H₂O)/CO₂; 72 mL/min; 40° C.; 100 bar) to give: Isomer A (faster eluting) and Isomer B (slower eluting): MS (ESI) m/z 325.1 [M+1] for both.

Intermediate B23: (S)-7-(chloromethyl)-4-(cyclopropylethynyl)-4-(1,1-difluoroethyl)-6-fluoro-3,4-dihydroquinazolin-2(1H)-one

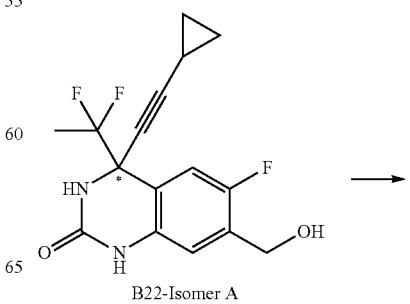

-continued

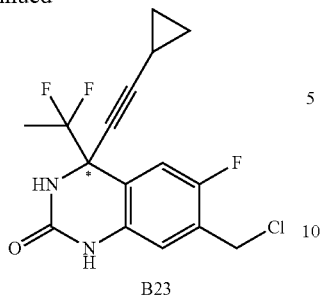

B23

Intermediate B23 was prepared using a procedure analogous to Intermediate B11 except that Intermediate B03 was replaced by Intermediate B22-Isomer A. MS (ESI) m/z 343 [M+1].

Intermediate B24: (S)-4-(cyclopropylethynyl)-7-(hydroxymethyl)-4-(trifluoromethyl)-3,4-dihydroquinazoline-2(1H)-thione

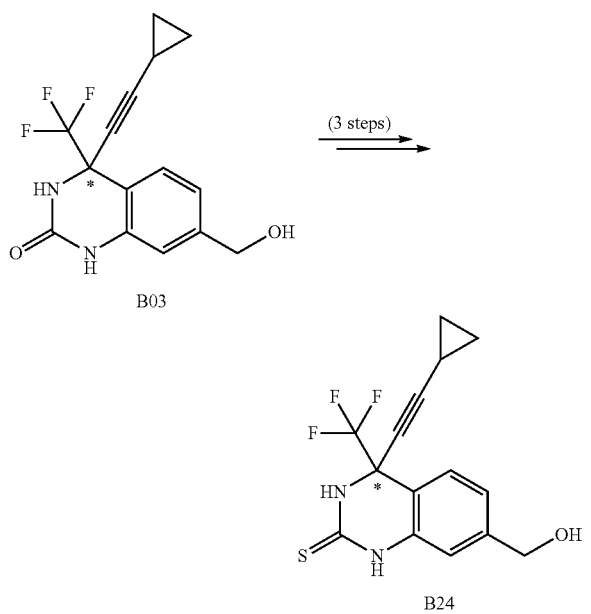

Step 1: (S)-7-(((tert-butyldimethylsilyl)oxy)methyl)-4-(cyclopropylethynyl)-4-(trifluoromethyl)-3,4-dihydroquinazolin-2(1H)-one: To a stirred solution of intermediate B03 (300 mg, 0.967 mmol) in DCM (6 mL) was added TBSCl (364 mg, 2.417 mmol) and imidazole (329 mg, 4.83 mmol). The reaction was stirred at 50° C. for 3 h, and then concentrated, and purified by flash column (SiO₂, 9-25% EtOAc/PE) to give the title compound.

Step 2: (S)-7-(((tert-butyldimethylsilyl)oxy)methyl)-4-(cyclopropylethynyl)-4-(trifluoromethyl)-3,4-dihydroquinazoline-2(1H)-thione: To a solution of (S)-7-(((tert-butyldimethylsilyl)oxy)methyl)-4-(cyclopropylethynyl)-4-(trifluoromethyl)-3,4-dihydroquinazolin-2(1H)-one (200 mg, 0.471 mmol) in toluene (7.5 mL), was added Lawesson's reagent (400 mg, 0.989 mmol). The resulting mixture was stirred at 100° C. for 4 h. The reaction mixture was concentrated and purified by flash column (SiO₂, 20% EtOAc/PE) to give the title compound. MS (ESI) m/z 441.2 [M+1].

Step 3: (S)-4-(cyclopropylethynyl)-7-(hydroxymethyl)-4-(trifluoromethyl)-3,4-dihydroquinazoline-2(1H)-thione: A solution of (S)-7-(((tert-butyldimethylsilyl)oxy)methyl)-4-(cyclopropylethynyl)-4-(trifluoromethyl)-3,4-dihydroquinazoline-2(1H)-thione (200 mg, 0.454 mmol) in DCM (10 mL) and TFA (2 mL) was stirred at 25° C. for 1 h. The mixture was concentrated and purified by prep-TLC (SiO₂, 30% EtOAc/PE) to give the title compound. MS (ESI) m/z 327.1 [M+1].

Intermediate B25: (S)-7-(chloromethyl)-4-(cyclopropylethynyl)-4-(trifluoromethyl)-3,4-dihydroquinazoline-2(1H)-thione

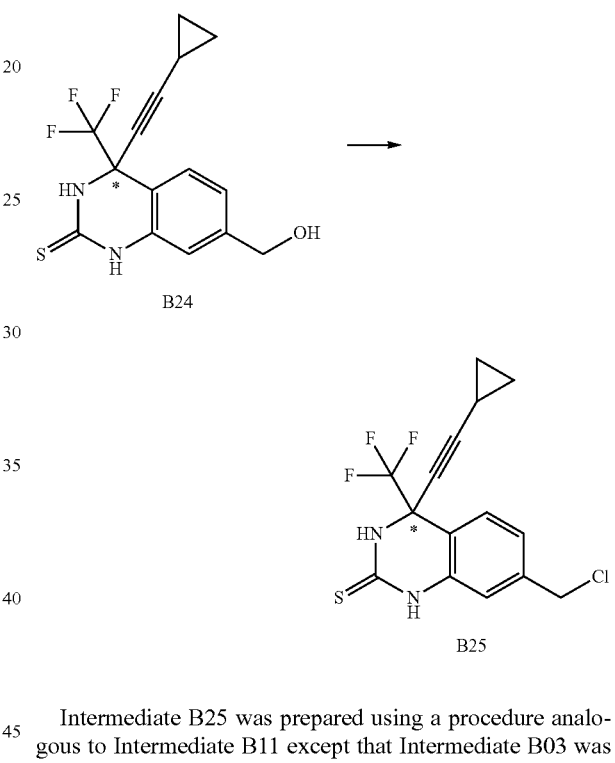

Intermediate B25 was prepared using a procedure analogous to Intermediate B11 except that Intermediate B03 was replaced by Intermediate B24. MS (ESI) m/z 345.1 [M+1].

Intermediate B26: (S)-7-(chloromethyl)-4-(cyclopropylethynyl)-3-methyl-4-(trifluoromethyl)-3,4-dihydroquinazolin-2(1H)-one

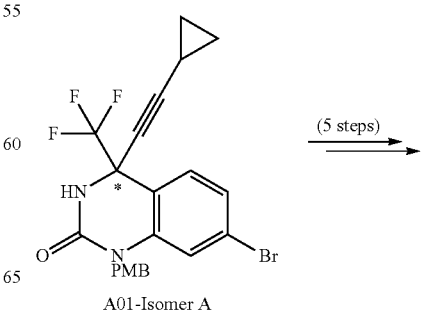

A01-Isomer A

51

-continued

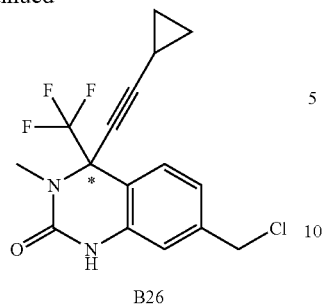

B26

Step 1: (S)-7-bromo-4-(cyclopropylethynyl)-1-(4-methoxybenzyl)-3-methyl-4-(trifluoromethyl)-3,4-dihydroquinazolin-2(1H)-one: A solution of intermediate A01-Isomer A (1.05 g, 2.191 mmol) in anhydrous 1,4-dioxane (21.91 mL), was treated with NaH (0.175 g, 4.38 mmol). Then, $CH_3I$ (0.411 mL, 6.57 mmol) was added and stirred at 25° C. The mixture was quenched with sat aq $NH_4Cl$ sol, extracted with EtOAc (3×). The combined organic layer was dried over $Na_2SO_4$, filtered and concentrated. The resulting residue was purified by flash chromatography ($SiO_2$, 0-100% EtOAc:hexanes) to provide the title compound.

Step 2: (S)-4-(cyclopropylethynyl)-1-(4-methoxybenzyl)-7-(((4-methoxybenzyl)oxy)methyl)-3-methyl-4-(trifluoromethyl)-3,4-dihydroquinazolin-2(H)-one: A mixture of (S)-7-bromo-4-(cyclopropylethynyl)-1-(4-methoxybenzyl)-3-methyl-4-(trifluoromethyl)-3,4-dihydroquinazolin-2(1H)-one (500 mg, 1.014 mmol), potassium (4-methoxy)benzyloxymethyl trifluoroborate (575 mg, 2.230 mmol) and $PdCl_2$(dppf) (83 mg, 0.101 mmol) in anhydrous 1,4-dioxane (10 mL), was treated with a 3 M $Cs_2CO_3$ aq sol (2027 µL, 6.08 mmol). The resulting mixture was irradiated at 150° C. in the microwave oven for 30 min. The mixture was quenched with sat aq $NH_4Cl$ sol, extracted with EtOAc (3×). The combined organic layers were dried over $Na_2SO_4$, filtered and concentrated. The residue was purified with flash chromatography ($SiO_2$, 0-100% EtOAc/hexanes) to give the title compound.

Step 3: (S)-4-(cyclopropylethynyl)-7-(hydroxymethyl)-1-(4-methoxybenzyl)-3-methyl-4-(trifluoromethyl)-3,4-dihydroquinazolin-2(1H)-one: A solution of (S)-4-(cyclopropylethynyl)-1-(4-methoxybenzyl)-7-(((4-methoxybenzyl)oxy)methyl)-3-methyl-4-(trifluoromethyl)-3,4-dihydroquinazolin-2(1H)-one_(250 mg, 0.443 mmol) in DCM (8.8 mL) was treated with TFA (341 µL, 4.43 mmol), and stirred at 25° C. for 30 min. The mixture was carefully quenched with sat aq $NaHCO_3$ sol, extracted with DCM. The organic layer was concentrated, and the residue was purified with flash chromatography ($SiO_2$, 0-100%, EtOAc/hexanes) to give the title compound. MS (ESI) m/z 445 [M+1].

Step 4: (S)-4-(cyclopropylethynyl)-7-(hydroxymethyl)-3-methyl-4-(trifluoromethyl)-3,4-dihydroquinazolin-2(1H)-one: To a solution of (S)-4-(cyclopropylethynyl)-7-(hydroxymethyl)-1-(4-methoxybenzyl)-3-methyl-4-(trifluoromethyl)-3,4-dihydroquinazolin-2(1H)-one (208 mg, 0.468 mmol) in MeCN (4 mL)/water (1 mL) was added CAN (1.03 g, 1.87 mmol). The reaction mixture was stirred at 25° C. for 3 h. The mixture was diluted with EtOAc and washed with water. The organic layer was dried, concentrated, and purified by flash column ($SiO_2$, 0-10% DCM/MeOH) to give the title compound.

52

Step 5: (S)-7-(chloromethyl)-4-(cyclopropylethynyl)-3-methyl-4-(trifluoromethyl)-3,4-dihydroquinazolin-2(1H)-one: A mixture of (S)-4-(cyclopropylethynyl)-7-(hydroxymethyl)-3-methyl-4-(trifluoromethyl)-3,4-dihydroquinazolin-2(1H)-one (83 mg, 0.256 mmol) and thionyl chloride (0.187 mL, 2.56 mmol) in DCM (1 mL) was stirred at 50° C. for 2 h. The reaction mixture was concentrated to provide the title compound.

Intermediates: Section C

Intermediate C01:
5-Amino-6-hydroxypyrimidine-4-carbonitrile

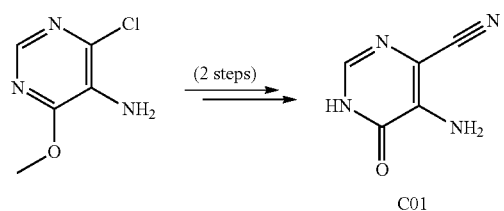

Step 1: 5-amino-6-methoxypyrimidine-4-carbonitrile: A mixture of $Pd(PPh_3)_4$ (434 mg, 0.38 mmol), 4-chloro-6-methoxypyrimidin-5-amine (300 mg, 1.9 mmol) and dicyanozinc (331 mg, 2.82 mmol) in DMA (6 mL) was stirred at 140° C. for 15 h. The reaction mixture was directly purified by prep-HPLC (water:MeCN with 0.1% TFA) to afford the title compound.

Step 2: 5-amino-6-hydroxypyrimidine-4-carbonitrile: To a solution of 5-amino-6-methoxypyrimidine-4-carbonitrile (20 mg, 0.133 mmol) in DMF (0.6 ml) was added pyridine hydrochloride (123 mg, 1.066 mmol). The reaction was stirred for 2 h at 120° C. The mixture was concentrated to afford the title compound which was used directly in the next step.

Intermediate C02:
5-amino-6-chloropyrimidin-4(3H)-one

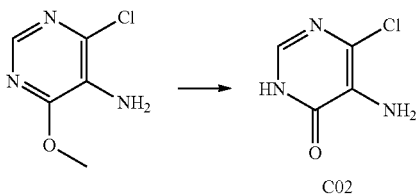

To a solution of 4-chloro-6-methoxypyrimidin-5-amine (100 mg, 0.627 mmol) in DMF (1 mL) was added pyridine hydrochloride (724 mg, 6.27 mmol). The reaction was stirred at 120° C. for 2 h and concentrated to afford the title compound, which was used directly without purification.

Intermediate C03:
6-(methoxymethyl)pyrimidin-4(3H)-one

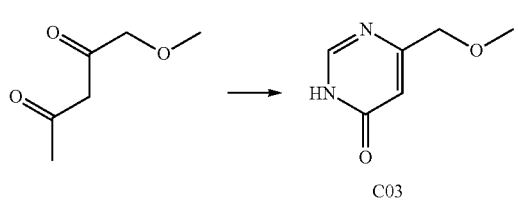

To a solution of methyl 4-methoxy-3-oxobutanoate (3.81 g, 26.1 mmol) in MeOH (25.2 mL) was added formimidamide hydrochloride (2 g, 24.84 mmol) and sodium methoxide (1.409 g, 26.1 mmol) at 25° C. and stirred at 25° C. for 16 h. The reaction was concentrated, and the resulting residue was treated with water (50 mL), and the mixture was extracted with hot CHCl$_3$ (3×30 mL). The combined organic layer was concentrated and purified by prep-HPLC (water:MeCN with 0.1% TFA) to afford the title compound. MS (ESI) m/z 141 [M+1].

Intermediate C04:
3-amino-5-methylpyrazin-2(1H)-one

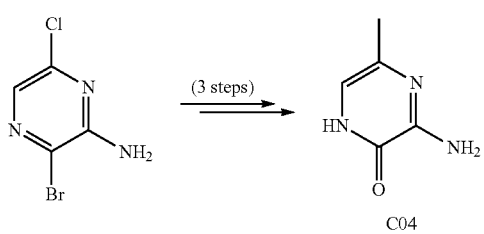

Step 1: 6-chloro-3-methoxypyrazin-2-amine: To a solution of 3-bromo-6-chloropyrazin-2-amine (3000 mg, 14.39 mmol) in MeOH (30 mL), was added sodium methoxide (1555 mg, 28.8 mmol). The mixture was stirred at 80° C. for 36 h. The mixture was concentrated, and the residue was dissolved in H$_2$O (50 mL) and extracted with EtOAc (3×60 mL). The combined organic layer was washed with brine (80 mL), dried over Na$_2$SO$_4$, filtered and concentrated. The crude was purified by prep-HPLC (water:MeCN with 0.1% TFA) to afford the title compound.

Step 2: 3-methoxy-6-methylpyrazin-2-amine: To a solution of 6-chloro-3-methoxypyrazin-2-amine (200 mg, 1.253 mmol) in 1,4-dioxane (4 mL) and water (0.8 ml) were added trimethylboroxine (787 mg, 6.27 mmol), K$_2$CO$_3$ (520 mg, 3.76 mmol), Pd(OAc)$_2$ (28.1 mg, 0.125 mmol), Xphos (119 mg, 0.251 mmol). The reaction mixture was stirred at 100° C. for 2 h under N$_2$. The mixture was filtered and purified by prep-HPLC (water:MeCN with 0.1% TFA) to afford the title compound. MS (ESI) m/z 140 [M+1].

Step 3: 3-amino-5-methylpyrazin-2(1H)-one: To a solution of 3-methoxy-6-methylpyrazin-2-amine (110 mg, 0.790 mmol) in MeCN (6 ml) was added TMSCl (0.152 ml, 1.186 mmol) and KI (328 mg, 1.976 mmol). The reaction was stirred for 2 h at 90° C. The mixture was filtered and the solid was dried to afford the title compound, which was used directly in the next step.

Intermediate C05:
6-(hydroxymethyl)pyrimidin-4(3H)-one

A solution of ethyl 6-oxo-1,6-dihydropyrimidine-4-carboxylate (80 mg, 0.476 mmol) in THF (1.6 ml) was added LiBH$_4$ (20.73 mg, 0.952 mmol) at 0° C. Then, the reaction was stirred at 25° C. for 2 h. The reaction was quenched with EtOH (0.2 mL). The resulting mixture was concentrated to dryness to give the title compound, which was used without further purification.

Intermediate C06:
5-(hydroxymethyl)pyrimidin-4(3H)-one

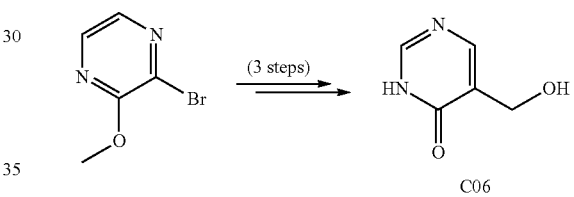

Step 1: 4-methoxy-5-vinylpyrimidine: To a stirred solution of 5-bromo-4-methoxypyrimidine (500 mg, 2.65 mmol) and K$_2$CO$_3$ (1097 mg, 7.94 mmol) and potassium vinyltrifluoroborate (532 mg, 3.97 mmol) in 1,4-dioxane (8 mL) and water (0.8 mL) was added PdCl$_2$(dppf) (194 mg, 0.265 mmol) under N$_2$. Then, the resulting mixture was stirred at 100° C. for 2 h. The mixture was concentrated, and the residue was diluted with water (30 mL) and extracted with EtOAc (3×40 mL). The combined organic layer was dried over Na$_2$SO$_4$, filtered and concentrated. The crude was purified by flash column (SiO$_2$, 10-50% EtOAc/PE) to provide the title compound.

Step 2: 5-(hydroxymethyl)pyrimidin-4-ol: A stream of ozone (38.8 mg, 0.808 mmol) was bubbled through a solution of 4-methoxy-5-vinylpyrimidine (110 mg, 0.808 mmol) in DCM (20 mL) and MeOH (2 mL) at −70° C. and stirred for 10 min. O2 was bubbled through the solution to remove the excess ozone. Then, NaBH$_4$ (92 mg, 2.424 mmol) was added at −70° C. and stirred for 20 min, and then the reaction was allowed to warm to 15° C. and stirred for additional 30 min. The reaction was quenched with water (30 mL) and extracted with EtOAc (3×40 mL). The combined organic layer was washed with brine (50 mL) and dried over Na$_2$SO$_4$, filtered and concentrated to give the title compound, which was used without further purification.

Step 3: 5-(hydroxymethyl)pyrimidin-4(3H)-one: To a solution of (4-methoxypyrimidin-5-yl)methanol (30 mg, 0.21 mmol) in MeCN (1 mL) was added KI (178 mg, 1.07 mmol). TMSCl (0.14 ml, 1.07 mmol) was added and the resulting mixture was stirred at 80° C. for 3 h. The reaction was concentrated to give the title compound, which was used without purification.

Intermediate C07:
3-amino-5-chloropyrazin-2(1H)-one

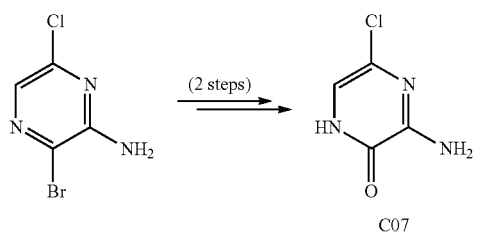 [SMILES: Nc1nc(Cl)cnc1Br ; Nc1nc(Cl)c[nH]c1=O ; "C07"]

Step 1: 6-chloro-3-methoxypyrazin-2-amine: To a solution of 3-bromo-6-chloropyrazin-2-amine (3 g, 14.39 mmol) in MeOH (30 mL) was added NaOMe (1.5 g, 28.8 mmol). The mixture was stirred at 80° C. for 36 h. The mixture was concentrated and diluted with water (50 mL) and extracted with EtOAc (3×60 mL). The combined organic layer was washed with brine (80 mL) and dried over $Na_2SO_4$, filtered and concentrated to give the title compound, which was used without further purification.

Step 2: 3-amino-5-chloropyrazin-2(1H)-one: To a solution of 6-chloro-3-methoxypyrazin-2-amine (500 mg, 3.13 mmol) in DCE (0.5 mL), $BBr_3$ (0.148 ml, 1.567 mmol) was added dropwise at 20° C. The reaction was stirred at 60° C. for 16 h. The mixture was quenched with MeOH (10 mL) at 0° C. The mixture was allowed to warm to 25° C. and stirred for 1 h. The solid was collected by filtration and washed with DCM (5×10 mL) and dried to afford the title compound.

Intermediate C08: 6-methoxypyridazin-3(2H)-one

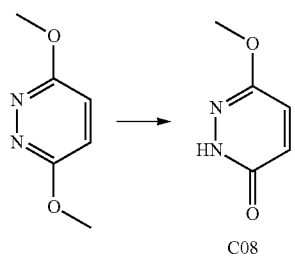

To a mixture of 3,6-dimethoxypyridazine (200 mg, 1.427 mmol) in 37% HCl sol (1 ml) was heated under reflux for 1 h at 110° C. The reaction mixture was concentrated and the residue was diluted with water (10 ml) and treated with sat $K_2CO_3$ sol to adjust the pH to 7 to form a precipitate. The solid was collected and dried to provide the title compound.

Intermediate C09: Tert-butyl
(6-methyl-3-oxo-3,4-dihydropyrazin-2-yl)carbamate

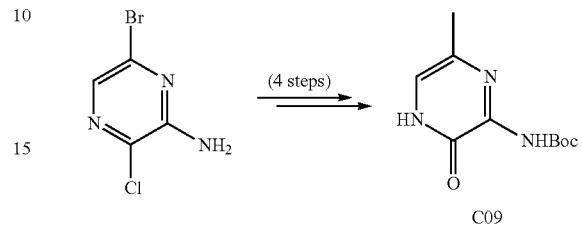

Step 1: 6-bromo-3-methoxypyrazin-2-amine: To a solution of 6-bromo-3-chloropyrazin-2-amine (600 mg, 2.88 mmol) in MeOH (6 ml), was added sodium methoxide (311 mg, 5.76 mmol). The mixture was stirred at 80° C. for 36 h. The reaction mixture was concentrated and diluted with water (50 mL) and extracted with EtOAc (60 mL×3). The combined organic layer was washed with brine (80 mL), dried over $Na_2SO_4$, and concentrated. The resulting crude was purified by prep-HPLC (water:MeCN with 0.1% TFA) to give the title product.

Step 2: 3-methoxy-6-methylpyrazin-2-amine: To a solution of 6-chloro-3-methoxypyrazin-2-amine (200 mg, 1.253 mmol) in 1,4-dioxane (4 ml) and water (0.8 ml) were added trimethylboroxine (787 mg, 6.27 mmol), $K_2CO_3$ (520 mg, 3.76 mmol), $Pd(OAc)_2$ (28.1 mg, 0.125 mmol) and X-Phos (120 mg, 0.251 mmol). The reaction mixture was stirred at 100° C. for 2 h under $N_2$. The mixture was diluted with $H_2O$ (20 mL) and extracted with EtOAc (40 mL×3). The combined organic layer was washed with brine (60 mL), dried over $Na_2SO_4$, filtered and concentrated. The crude was purified by pre-TLC ($SiO_2$, PE:EtOAc=1:1) to give the title compound.

Step 3: 3-amino-5-methylpyrazin-2-ol: To a solution of 3-methoxy-6-methylpyrazin-2-amine (30 mg, 0.216 mmol) in ACN (0.8 ml) was added TMS-Cl (0.055 ml, 0.431 mmol) and KI (107 mg, 0.647 mmol). The reaction was stirred for 15 h under $N_2$ at 90° C. The mixture was concentrated to dryness to give the title compound, which used directly for the next step.

Step 4: tert-butyl (6-methyl-3-oxo-3,4-dihydropyrazin-2-yl)carbamate: To a solution of 3-amino-5-methylpyrazin-2(1H)-one (100 mg, 0.799 mmol) in DCM (1 mL) were added di-tert-butyl dicarbonate (0.367 mL, 1.598 mmol) and DMAP (9.76 mg, 0.080 mmol). The reaction was stirred at 25° C. for 2 h. The mixture was concentrated and purified by prep-TLC ($SiO_2$, PE:EA=1:1) to give the title compound.

Intermediates used to prepare each of Examples 1-85 that were not commercially available were prepared as described above and are noted in the INT column of Table 1.

Example 1: (S)-4-(cyclopropylethynyl)-6-fluoro-7-((6-oxopyrimidin-1(6H)-yl)methyl)-4-(trifluoromethyl)-3,4-dihydroquinazolin-2(1H)-one

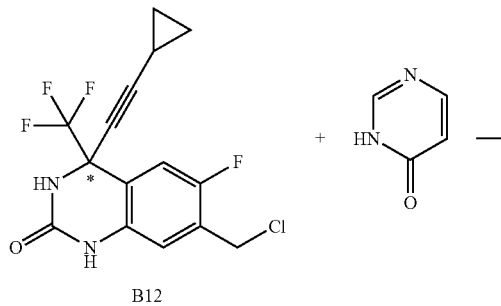

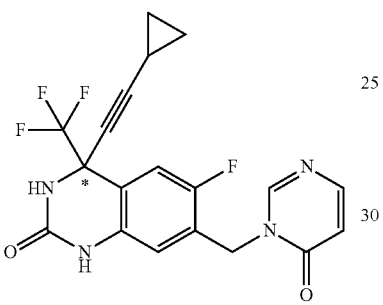

To a solution of intermediate B12 (95 mg, 0.27 mmol) and pyrimidin-4(3H)-one (66 mg, 0.68 mmol) in DMA (1.8 mL) was added K$_2$CO$_3$ (76 mg, 0.55 mmol). The reaction was stirred at 80° C. for 2 h. The solution was purified by prep-HPLC (water:MeCN with 0.1% TFA) to afford the title compound. $^1$H NMR (500 MHz, DMSO-d$_6$) δ 9.66 (s, 1H), 8.60 (s, 1H), 8.43 (s, 1H), 7.98 (d, J=6.6 Hz, 1H), 7.22 (d, J=10.0 Hz, 1H), 6.68 (d, J=6.5 Hz, 1H), 6.46 (d, J=6.6 Hz, 1H), 5.16-5.05 (m, 2H), 1.48 (m, 1H), 0.87 (m, 2H), 0.74 (m, 2H) ppm. MS (ESI) m/z 407 [M+1].

Example 2: (S)-7-((3-amino-2-oxopyrazin-1(2H)-yl)methyl)-4-(cyclopropylethynyl)-6-fluoro-4-(trifluoromethyl)-3,4-dihydroquinazolin-2(1H)-one

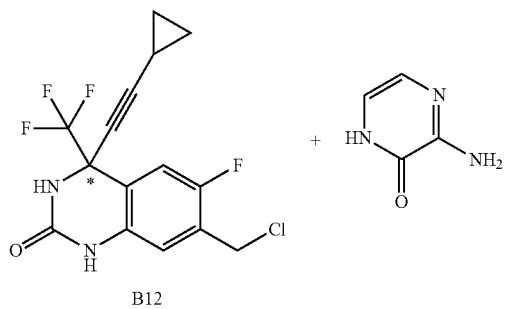

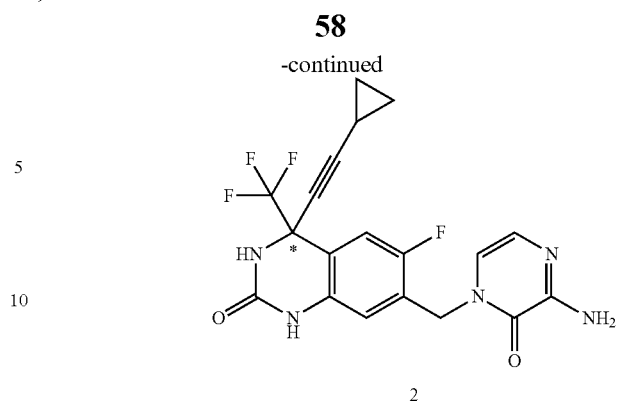

To a solution of intermediate B12 (700 mg, 2.02 mmol) in DMA (20.2 mL) was added K$_2$CO$_3$ (558 mg, 4.04 mmol) and 3-aminopyrazin-2(1H)-one (561 mg, 5.05 mmol). The reaction was stirred at 80° C. for 1 h. The solution was filtered and purified by prep-HPLC (water: MeCN with 0.1% TFA) to afford the title compound. $^1$H NMR (500 MHz, DMSO-d$_6$) δ 9.68 (s, 1H), 8.42 (s, 1H), 7.22 (d, J=9.8 Hz, 1H), 6.83 (d, J=4.6 Hz, 1H), 6.71 (d, J=4.6 Hz, 1H), 6.70 (br s, 2H), 6.66 (d, J=6.4 Hz, 1H), 5.10-4.96 (m, 2H), 1.52-1.42 (m, 1H), 0.88 (dd, J=8.2, 2.9 Hz, 2H), 0.75-0.71 (m, 2H) ppm. MS (ESI) m/z 422 [M+1].

Example 3: (S)-6-chloro-4-(cyclopropylethynyl)-7-((4-methyl-6-oxopyrimidin-1(6H)-yl)methyl)-4-(trifluoromethyl)-3,4-dihydroquinazolin-2(1H)-one

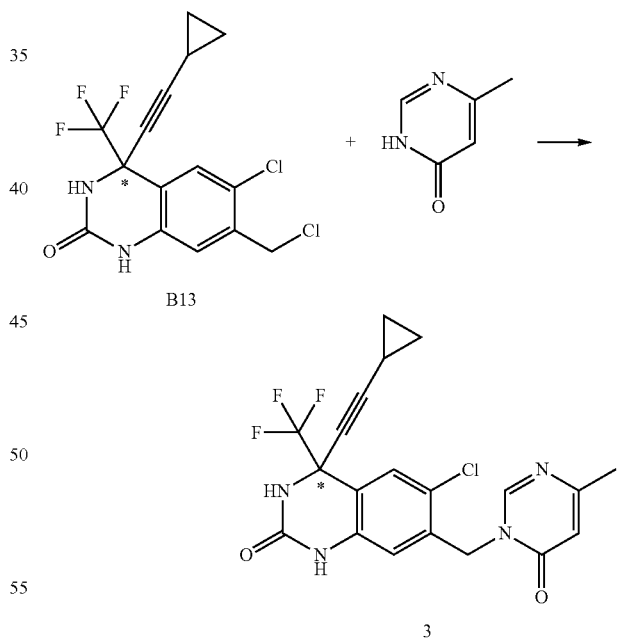

To a solution of intermediate B13 (350 mg, 0.96 mmol) and 6-methylpyrimidin-4(3H)-one (212 mg, 1.93 mmol) in DMF (11 mL) were added K$_2$CO$_3$ (400 mg, 2.89 mmol) and LiBr (126 mg, 1.45 mmol). The mixture was stirred at 50° C. for 2 h. Water (20 mL) was added and the mixture was extracted with EtOAc (3×25 mL). The combined organic layer was washed with brine (25 mL), dried over Na$_2$SO$_4$, filtered, concentrated and purified by prep HPLC (water: MeCN with 0.05% NH$_4$OH) to afford the title compound.

$^1$H NMR (400 MHz, MeOH-d$_4$) δ ppm 0.75-0.80 (m, 2H), 0.88-0.95 (m, 2H), 1.35-1.50 (m, 1H), 2.33 (s, 3H), 5.23 (s, 2H), 6.41 (s, 1H), 6.65 (s, 1H), 7.53 (s, 1H), 8.51 (s, 1H). MS (ESI) m/z 437.2 [M+1].

Example 4: (S)-4-(cyclopropylethynyl)-4-(1,1-difluoroethyl)-6-fluoro-7-((6-oxopyrimidin-1(6H)-yl)methyl)-3,4-dihydroquinazolin-2(1H)-one

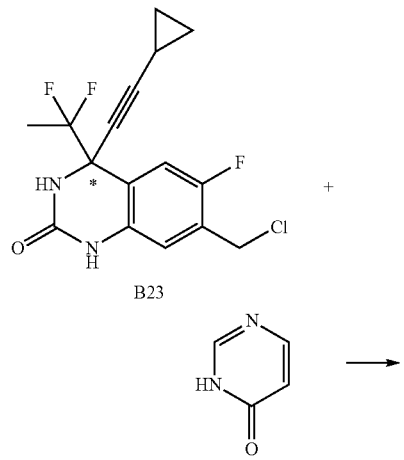

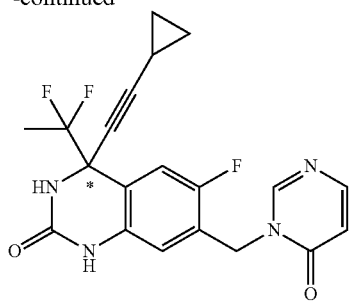

To a solution of (intermediate B23 (423 mg, 1.23 mmol) and pyrimidin-4(3H)-one (237 mg, 2.47 mmol) in DMF (5 mL) was added K$_2$CO$_3$ (512 mg, 3.70 mmol), and the resulting mixture was stirred at 50° C. for 1 h. Water (20 mL) was added to the reaction and the mixture was extracted with EtOAc (3×15 mL). The combined organic layer was washed with brine (35 mL), dried over Na$_2$SO$_4$, filtered, concentrated and purified by prep-HPLC (water:MeCN with 0.05% NH$_4$OH) to give product the title compound. $^1$H NMR 400 MHz, MeOH-d$_4$) δ=8.57 (s, 1H), 7.98 (d, J 6.6 Hz, 1H), 7.24 (d, J=10.4 Hz, 1H), 6.81 (d, J=6.4 Hz, 1H), 6.51 (d, J=6.6 Hz, 1H), 5.24-5.13 (m, 2H), 1.68 (t, J=18.5 Hz, 3H), 1.40 (tt, J=5.0, 8.3 Hz, 1H), 0.91-0.84 (m, 2H), 0.77-0.71 (in, 2H). MS (ESI) m/z 403.1 [M+1].

The compounds in Table 1 were prepared in an analogous fashion to that described for Example 1.

TABLE 1

| Ex. | Structure | IUPAC Name | MS [M + 1] | INT. |
|---|---|---|---|---|
| 5 | 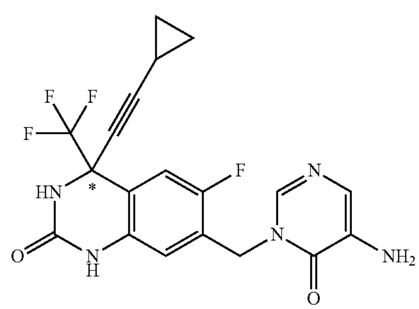 [SMILES: Nc1cncn(Cc2cc3c(cc2F)C(C#CC2CC2)(C(F)(F)F)NC(=O)N3)c1=O] | (S)-7-((5-amino-6-oxopyrimidin-1(6H)-yl)methyl)-4-(cyclopropylethynyl)-6-fluoro-4-(trifluoromethyl)-3,4-dihydroquinazolin-2(1H)-one | 422 | B12 |
| 6 | 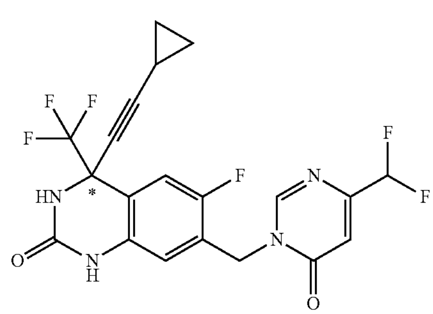 [SMILES: O=C1Nc2cc(Cn3cnc(C(F)F)cc3=O)c(F)cc2C(C#CC2CC2)(C(F)(F)F)N1] | (S)-4-(cyclopropylethynyl)-7-((4-(difluoromethyl)-6-oxopyrimidin-1(6H)-yl)methyl)-6-fluoro-4-(trifluoromethyl)-3,4-dihydroquinazolin-2(1H)-one | 457 | B12 |

TABLE 1-continued

| Ex. | Structure | IUPAC Name | MS [M + 1] | INT. |
|---|---|---|---|---|
| 7 | 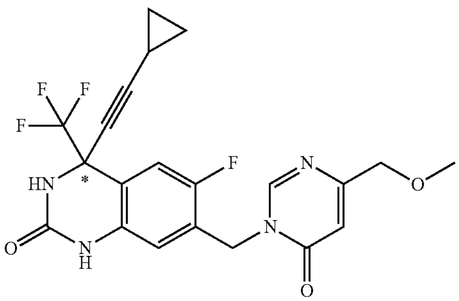 [SMILES: COCc1cc(=O)n(Cc2cc3c(cc2F)C(C#CC2CC2)(C(F)(F)F)NC(=O)N3)cn1] | (S)-4-(cyclopropylethynyl)-6-fluoro-7-((4-(methoxymethyl)-6-oxopyrimidin-1(6H)-yl)methyl)-4-(trifluoromethyl)-3,4-dihydroquinazolin-2(1H)-one | 451 | B12 |
| 8 | 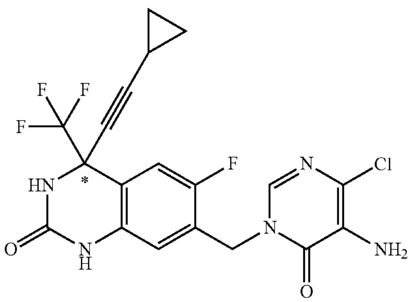 [SMILES: Nc1c(Cl)ncn(Cc2cc3c(cc2F)C(C#CC2CC2)(C(F)(F)F)NC(=O)N3)c1=O] | (S)-7-((5-amino-4-chloro-6-oxopyrimidin-1(6H)-yl)methyl)-4-(cyclopropylethynyl)-6-fluoro-4-(trifluoromethyl)-3,4-dihydroquinazolin-2(1H)-one | 456 | B12 |
| 9 | 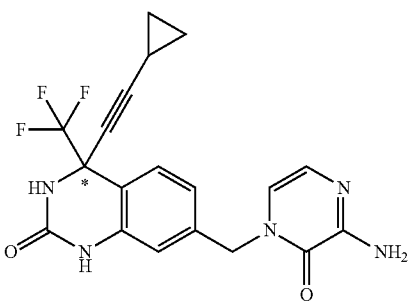 [SMILES: Nc1nccn(Cc2ccc3c(c2)NC(=O)NC3(C#CC2CC2)C(F)(F)F)c1=O] | (S)-7-((3-amino-2-oxopyrazin-1(2H)-yl)methyl)-4-(cyclopropylethynyl)-4-(trifluoromethyl)-3,4-dihydroquinazolin-2(1H)-one | 404 | B11 |
| 10 | 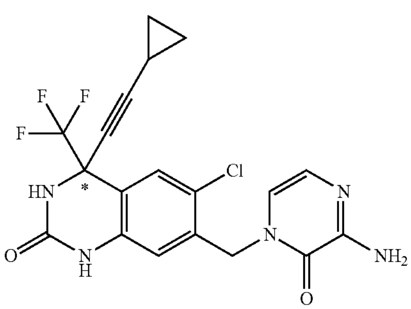 [SMILES: Nc1nccn(Cc2cc3c(cc2Cl)C(C#CC2CC2)(C(F)(F)F)NC(=O)N3)c1=O] | (S)-7-((5-amino-6-oxopyrimidin-1(6H)-yl)methyl)-6-chloro-4-(cyclopropylethynyl)-4-(trifluoromethyl)-3,4-dihydroquinazolin-2(1H)-one | 438 | B13 |
| 11 | 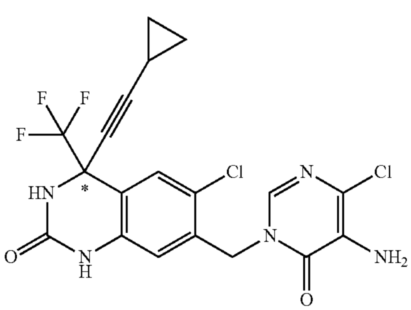 [SMILES: Nc1c(Cl)ncn(Cc2cc3c(cc2Cl)C(C#CC2CC2)(C(F)(F)F)NC(=O)N3)c1=O] | (S)-7-((5-amino-4-chloro-6-oxopyrimidin-1(6H)-yl)methyl)-6-chloro-4-(cyclopropylethynyl)-4-(trifluoromethyl)-3,4-dihydroquinazolin-2(1H)-one | 472 | B13, C02 |

TABLE 1-continued

| Ex. | Structure | IUPAC Name | MS [M + 1] | INT. |
|---|---|---|---|---|
| 12 | 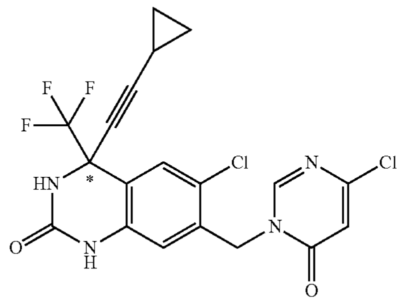 [SMILES: O=C1Nc2cc(Cn3cnc(Cl)cc3=O)c(Cl)cc2C(C#CC2CC2)(C(F)(F)F)N1] | (S)-6-chloro-7-((4-chloro-6-oxopyrimidin-1(6H)-yl)methyl)-4-(cyclopropylethynyl)-4-(trifluoromethyl)-3,4-dihydroquinazolin-2(1H)-one | 457 | B13 |
| 13 | 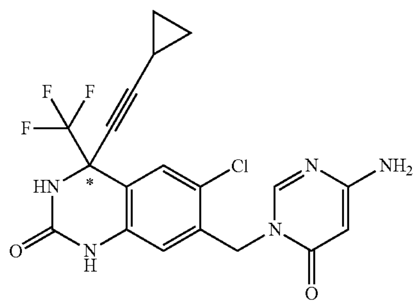 [SMILES: Nc1cc(=O)n(Cc2cc3c(cc2Cl)C(C#CC2CC2)(C(F)(F)F)NC(=O)N3)cn1] | (S)-7-((4-amino-6-oxopyrimidin-1(6H)-yl)methyl)-6-chloro-4-(cyclopropylethynyl)-4-(trifluoromethyl)-3,4-dihydroquinazolin-2(1H)-one | 438 | B13 |
| 14 | 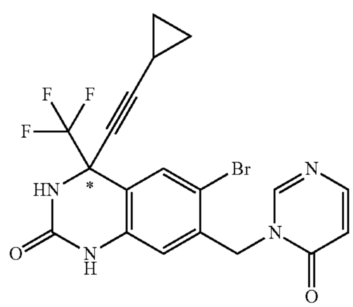 | (S)-6-bromo-4-(cyclopropylethynyl)-7-((6-oxopyrimidin-1(6H)-yl)methyl)-4-(trifluoromethyl)-3,4-dihydroquinazolin-2(1H)-one | 467, 469 | B18 |
| 15 | 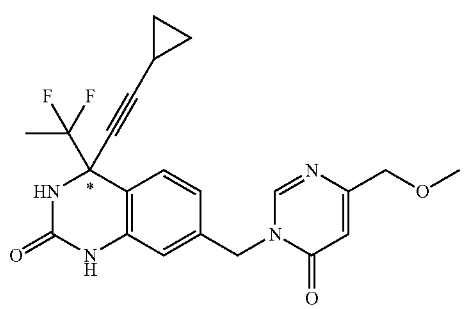 [SMILES: COCc1cc(=O)n(Cc2ccc3c(c2)NC(=O)NC3(C#CC2CC2)C(C)(F)F)cn1] | (S)-4-(cyclopropylethynyl)-4-(1,1-difluoroethyl)-7-((4-(methoxymethyl)-6-oxopyrimidin-1(6H)-yl)methyl)-3,4-dihydroquinazolin-2(1H)-one | 429 | B14, C03 |
| 16 | 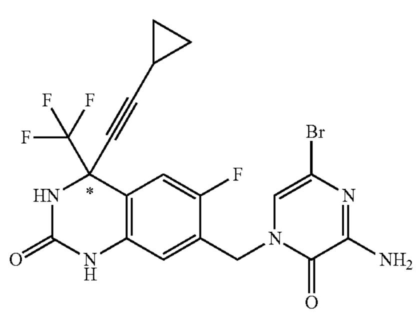 [SMILES: Nc1nc(Br)cn(Cc2cc3c(cc2F)C(C#CC2CC2)(C(F)(F)F)NC(=O)N3)c1=O] | (S)-7-((3-amino-5-bromo-2-oxopyrazin-1(2H)-yl)methyl)-4-(cyclopropylethynyl)-6-fluoro-4-(trifluoromethyl)-3,4-dihydroquinazolin-2(1H)-one | 500, 502 | B12 |

TABLE 1-continued

| Ex. | Structure | IUPAC Name | MS [M + 1] | INT. |
|---|---|---|---|---|
| 17 | 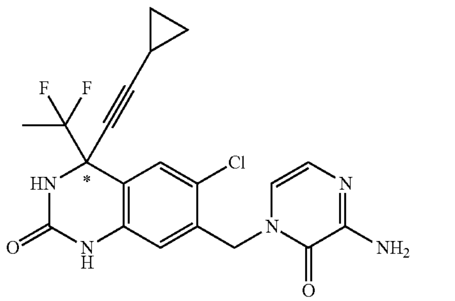 [SMILES: CC(F)(F)C1(C#CC2CC2)NC(=O)Nc2cc(Cn3ccnc(N)c3=O)c(Cl)cc21] | (S)-7-((3-amino-2-oxopyrazin-1(2H)-yl)methyl)-6-chloro-4-(cyclopropylethynyl)-4-(1,1-difluoroethyl)-3,4-dihydroquinazolin-2(1H)-one | 434 | B19 |
| 18 | 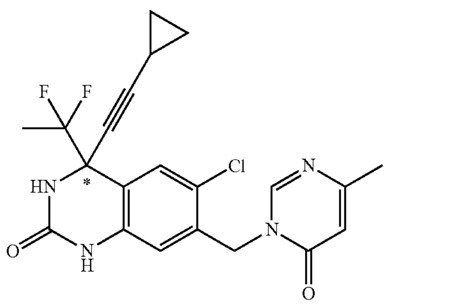 [SMILES: Cc1cc(=O)n(Cc2cc3c(cc2Cl)C(C#CC2CC2)(C(C)(F)F)NC(=O)N3)cn1] | (S)-6-chloro-4-(cyclopropylethynyl)-4-(1,1-difluoroethyl)-7-((4-methyl-6-oxopyrimidin-1(6H)-yl)methyl)-3,4-dihydroquinazolin-2(1H)-one | 433 | B19 |
| 19 | 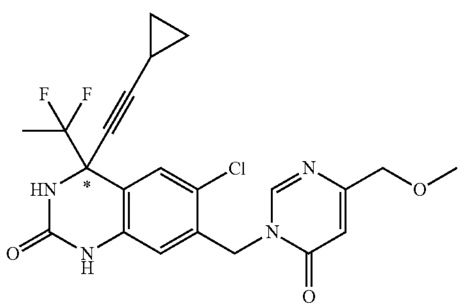 [SMILES: COCc1cc(=O)n(Cc2cc3c(cc2Cl)C(C#CC2CC2)(C(C)(F)F)NC(=O)N3)cn1] | (S)-6-chloro-4-(cyclopropylethynyl)-4-(1,1-difluoroethyl)-7-((4-(methoxymethyl)-6-oxopyrimidin-1(6H)-yl)methyl)-3,4-dihydroquinazolin-2(1H)-one | 463 | B19 |
| 20 | 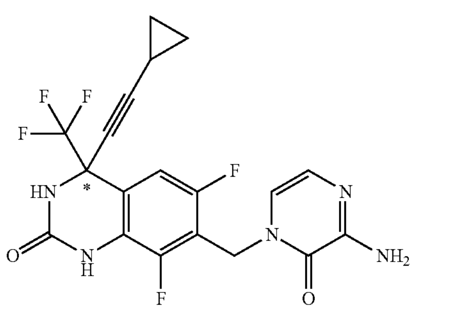 [SMILES: Nc1nccn(Cc2c(F)cc3c(c2F)NC(=O)NC3(C#CC2CC2)C(F)(F)F)c1=O] | (S)-7-((3-amino-2-oxopyrazin-1(2H)-yl)methyl)-4-(cyclopropylethynyl)-6,8-difluoro-4-(trifluoromethyl)-3,4-dihydroquinazolin-2(1H)-one | 440 | B20 |
| 21 | 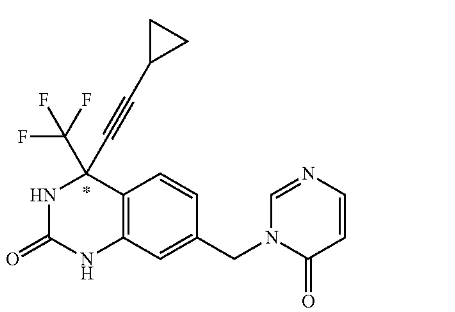 [SMILES: O=C1Nc2cc(Cn3cnccc3=O)ccc2C(C#CC2CC2)(C(F)(F)F)N1] | (S)-4-(cyclopropylethynyl)-7-((6-oxopyrimidin-1(6H)-yl)methyl)-4-(trifluoromethyl)-3,4-dihydroquinazolin-2(1H)-one | 389 | B11 |

TABLE 1-continued

| Ex. | Structure | IUPAC Name | MS [M + 1] | INT. |
|---|---|---|---|---|
| 22 | 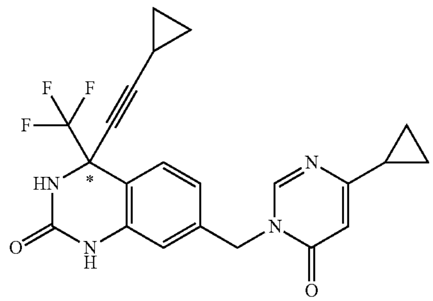 [SMILES: O=C1Nc2cc(Cn3cnc(C4CC4)cc3=O)ccc2C(C#CC2CC2)(C(F)(F)F)N1] | (S)-7-((4-cyclopropyl-6-oxopyrimidin-1(6H)-yl)methyl)-4-(cyclopropylethynyl)-4-(trifluoromethyl)-3,4-dihydroquinazolin-2(1H)-one | 429 | B11 |
| 23 | 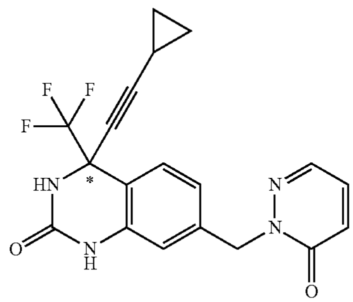 [SMILES: O=C1Nc2cc(Cn3ncccc3=O)ccc2C(C#CC2CC2)(C(F)(F)F)N1] | (S)-4-(cyclopropylethynyl)-7-((6-oxopyridazin-1(6H)-yl)methyl)-4-(trifluoromethyl)-3,4-dihydroquinazolin-2(1H)-one | 389 | B11 |
| 24 | 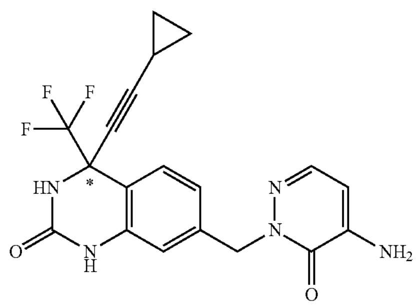 [SMILES: Nc1ccnn(Cc2ccc3c(c2)NC(=O)NC3(C#CC2CC2)C(F)(F)F)c1=O] | (S)-7-((5-amino-6-oxopyridazin-1(6H)-yl)methyl)-4-(cyclopropylethynyl)-4-(trifluoromethyl)-3,4-dihydroquinazolin-2(1H)-one | 404 | B11 |
| 25 | 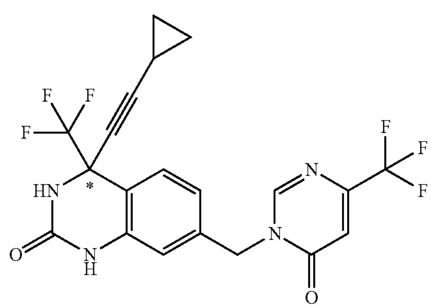 [SMILES: O=C1Nc2cc(Cn3cnc(C(F)(F)F)cc3=O)ccc2C(C#CC2CC2)(C(F)(F)F)N1] | (S)-4-(cyclopropylethynyl)-7-((6-oxo-4-(trifluoromethyl)pyrimidin-1(6H)-yl)methyl)-4-(trifluoromethyl)-3,4-dihydroquinazolin-2(1H)-one | 457 | B11 |
| 26 | 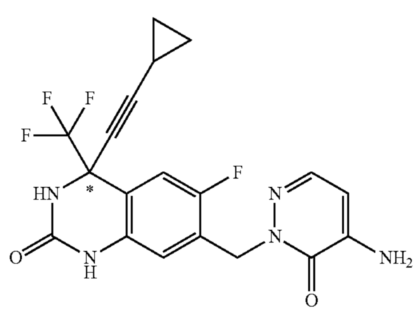 [SMILES: Nc1ccnn(Cc2cc3c(cc2F)C(C#CC2CC2)(C(F)(F)F)NC(=O)N3)c1=O] | (S)-7-((5-amino-6-oxopyridazin-1(6H)-yl)methyl)-4-(cyclopropylethynyl)-6-fluoro-4-(trifluoromethyl)-3,4-dihydroquinazolin-2(1H)-one | 422 | B12 |

TABLE 1-continued

| Ex. | Structure | IUPAC Name | MS [M + 1] | INT. |
|---|---|---|---|---|
| 27 | 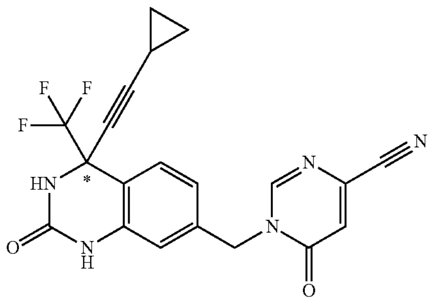 [SMILES: N#Cc1cc(=O)n(Cc2ccc3c(c2)NC(=O)NC3(C#CC2CC2)C(F)(F)F)cn1] | (S)-1-((4-(cyclopropylethynyl)-2-oxo-4-(trifluoromethyl)-1,2,3,4-tetrahydroquinazolin-7-yl)methyl)-6-oxo-1,6-dihydropyrimidine-4-carbonitrile | 414 | B11 |
| 28 | 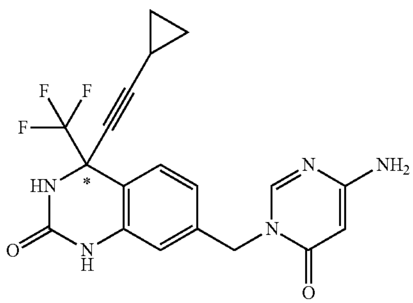 [SMILES: Nc1cc(=O)n(Cc2ccc3c(c2)NC(=O)NC3(C#CC2CC2)C(F)(F)F)cn1] | (S)-7-((4-amino-6-oxopyrimidin-1(6H)-yl)methyl)-4-(cyclopropylethynyl)-4-(trifluoromethyl)-3,4-dihydroquinazolin-2(1H)-one | 404 | B11 |
| 29 | 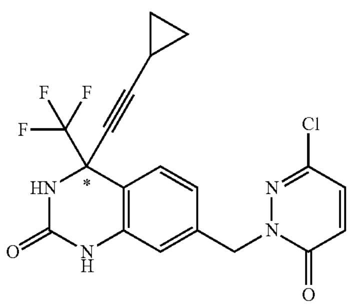 [SMILES: O=C1Nc2cc(Cn3nc(Cl)ccc3=O)ccc2C(C#CC2CC2)(C(F)(F)F)N1] | (S)-7-((3-chloro-6-oxopyridazin-1(6H)-yl)methyl)-4-(cyclopropylethynyl)-4-(trifluoromethyl)-3,4-dihydroquinazolin-2(1H)-one | 433 | B11 |
| 30 | 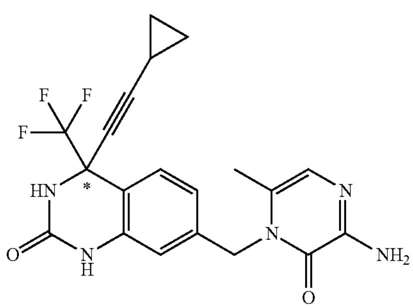 [SMILES: Cc1cnc(N)c(=O)n1Cc1ccc2c(c1)NC(=O)NC2(C#CC1CC1)C(F)(F)F] | (S)-7-((3-amino-6-methyl-2-oxopyrazin-1(2H)-yl)methyl)-4-(cyclopropylethynyl)-4-(trifluoromethyl)-3,4-dihydroquinazolin-2(1H)-one | 418 | B11 |
| 31 | 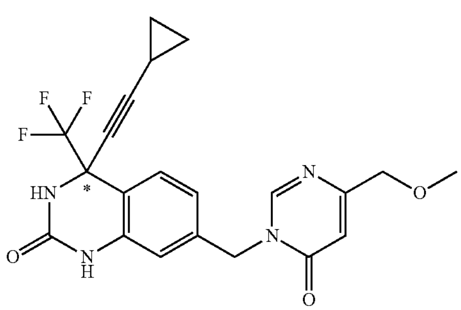 [SMILES: COCc1cc(=O)n(Cc2ccc3c(c2)NC(=O)NC3(C#CC2CC2)C(F)(F)F)cn1] | (S)-4-(cyclopropylethynyl)-7-((4-(methoxymethyl)-6-oxopyrimidin-1(6H)-yl)methyl)-4-(trifluoromethyl)-3,4-dihydroquinazolin-2(1H)-one | 433 | B11, CO3 |

TABLE 1-continued

| Ex. | Structure | IUPAC Name | MS [M + 1] | INT. |
|---|---|---|---|---|
| 32 | 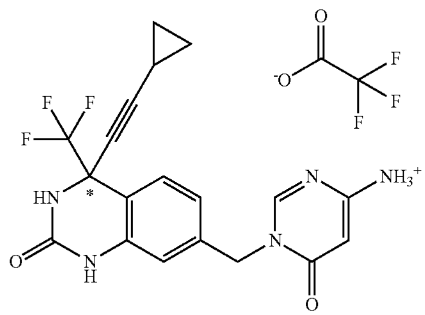 | (S)-1-((4-(cyclopropylethynyl)-2-oxo-4-(trifluoromethyl)-1,2,3,4-tetrahydroquinazolin-7-yl)methyl)-6-oxo-1,6-dihydropyrimidin-4-aminium 2,2,2-trifluoroacetate | 404 | B11 |
| 33 | 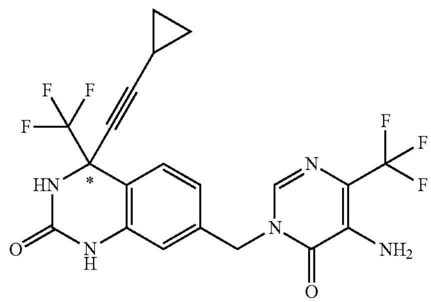 [SMILES: Nc1c(C(F)(F)F)ncn(Cc2ccc3c(c2)NC(=O)NC3(C#CC2CC2)C(F)(F)F)c1=O] | (S)-7-((5-amino-6-oxo-4-(trifluoromethyl)pyrimidin-1(6H)-yl)methyl)-4-(cyclopropylethynyl)-4-(trifluoromethyl)-3,4-dihydroquinazolin-2(1H)-one | 472 | B11 |
| 34 | 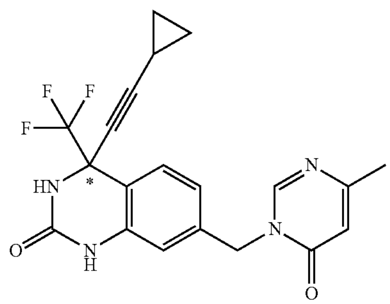 [SMILES: Cc1cc(=O)n(Cc2ccc3c(c2)NC(=O)NC3(C#CC2CC2)C(F)(F)F)cn1] | (S)-4-(cyclopropylethynyl)-7-((4-methyl-6-oxopyrimidin-1(6H)-yl)methyl)-4-(trifluoromethyl)-3,4-dihydroquinazolin-2(1H)-one | 419 | B11 |
| 35 | 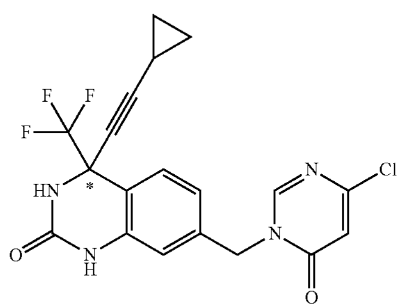 [SMILES: O=C1Nc2cc(Cn3cnc(Cl)cc3=O)ccc2C(C#CC2CC2)(C(F)(F)F)N1] | (S)-7-((4-chloro-6-oxopyrimidin-1(6H)-yl)methyl)-4-(cyclopropylethynyl)-4-(trifluoromethyl)-3,4-dihydroquinazolin-2(1H)-one | 423 | B11 |
| 36 | 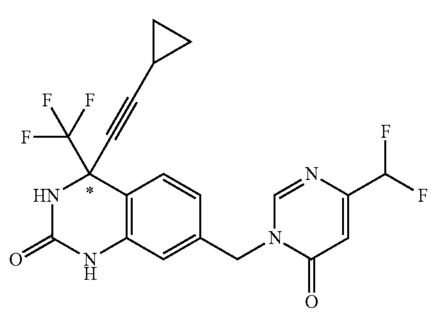 [SMILES: O=C1Nc2cc(Cn3cnc(C(F)F)cc3=O)ccc2C(C#CC2CC2)(C(F)(F)F)N1] | (S)-4-(cyclopropylethynyl)-7-((4-(difluoromethyl)-6-oxopyrimidin-1(6H)-yl)methyl)-4-(trifluoromethyl)-3,4-dihydroquinazolin-2(1H)-one | 439 | B11 |

TABLE 1-continued

| Ex. | Structure | IUPAC Name | MS [M + 1] | INT. |
|---|---|---|---|---|
| 37 | 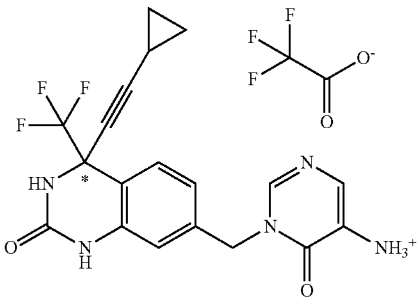 [SMILES: [NH3+]c1cncn(Cc2ccc3c(c2)NC(=O)NC3(C#CC2CC2)C(F)(F)F)c1=O ; O=C([O-])C(F)(F)F] | (S)-1-((4-(cyclopropylethynyl)-2-oxo-4-(trifluoromethyl)-1,2,3,4-tetrahydroquinazolin-7-yl)methyl)-6-oxo-1,6-dihydropyrimidin-5-aminium 2,2,2-trifluoroacetate | 404 | B11 |
| 38 | 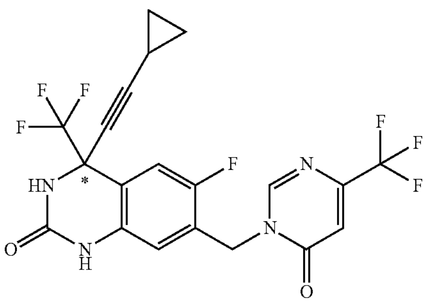 [SMILES: O=C1Nc2cc(Cn3cnc(C(F)(F)F)cc3=O)c(F)cc2C(C#CC2CC2)(C(F)(F)F)N1] | (S)-4-(cyclopropylethynyl)-6-fluoro-7-((6-oxo-4-(trifluoromethyl)pyrimidin-1(6H)-yl)methyl)-4-(trifluoromethyl)-3,4-dihydroquinazolin-2(1H)-one | 475 | B11 |
| 39 | 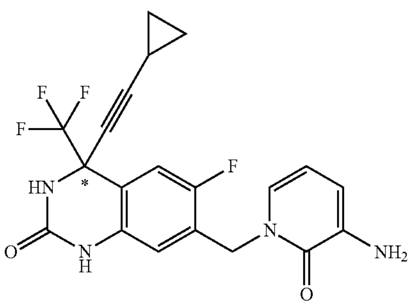 [SMILES: Nc1cccn(Cc2cc3c(cc2F)C(C#CC2CC2)(C(F)(F)F)NC(=O)N3)c1=O] | (S)-1-((3-amino-2-oxopyridin-1(2H)-yl)methyl)-4-(cyclopropylethynyl)-6-fluoro-4-(trifluoromethyl)-3,4-dihydroquinazolin-2(1H)-one | 421 | B11 |
| 40 | 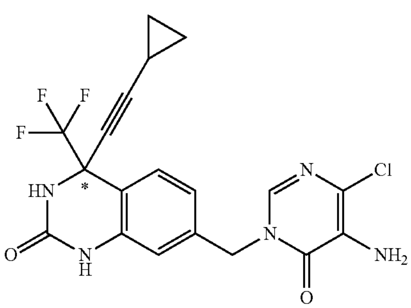 [SMILES: Nc1c(Cl)ncn(Cc2ccc3c(c2)NC(=O)NC3(C#CC2CC2)C(F)(F)F)c1=O] | (S)-7-((5-amino-4-chloro-6-oxopyrimidin-1(6H)-yl)methyl)-4-(cyclopropylethynyl)-4-(trifluoromethyl)-3,4-dihydroquinazolin-2(1H)-one | 438 | B11, CO2 |
| 41 | 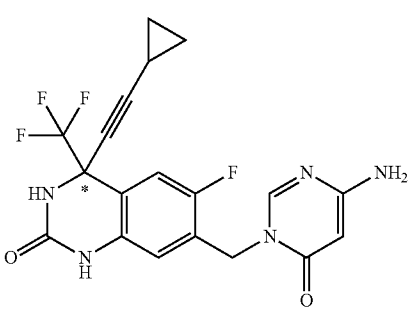 [SMILES: Nc1cc(=O)n(Cc2cc3c(cc2F)C(C#CC2CC2)(C(F)(F)F)NC(=O)N3)cn1] | (S)-7-((4-amino-6-oxopyrimidin-1(6H)-yl)methyl)-4-(cyclopropylethynyl)-6-fluoro-4-(trifluoromethyl)-3,4-dihydroquinazolin-2(1H)-one | 422 | B12 |

TABLE 1-continued

| Ex. | Structure | IUPAC Name | MS [M + 1] | INT. |
|---|---|---|---|---|
| 42 | 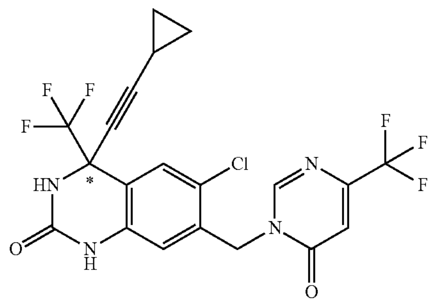 [SMILES: O=C1Nc2cc(Cn3cnc(C(F)(F)F)cc3=O)c(Cl)cc2C(C#CC2CC2)(C(F)(F)F)N1] | (S)-6-chloro-4-(cyclopropylethynyl)-7-((6-oxo-4-(trifluoromethyl)pyrimidin-1(6H)-yl)methyl)-4-(trifluoromethyl)-3,4-dihydroquinazolin-2(1H)-one | 491 | B13 |
| 43 | 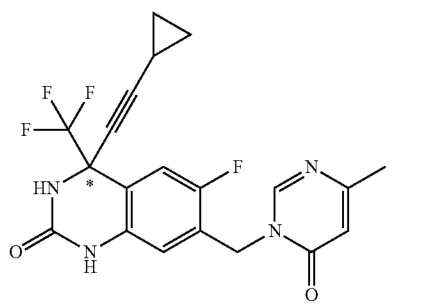 [SMILES: Cc1cc(=O)n(Cc2cc3c(cc2F)C(C#CC2CC2)(C(F)(F)F)NC(=O)N3)cn1] | (S)-4-(cyclopropylethynyl)-6-fluoro-7-((4-methyl-6-oxopyrimidin-1(6H)-yl)methyl)-4-(trifluoromethyl)-3,4-dihydroquinazolin-2(1H)-one | 421 | B12 |
| 44 | 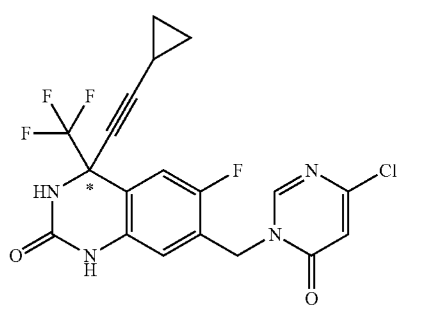 [SMILES: O=C1Nc2cc(Cn3cnc(Cl)cc3=O)c(F)cc2C(C#CC2CC2)(C(F)(F)F)N1] | (S)-7-((4-chloro-6-oxopyrimidin-1(6H)-yl)methyl)-4-(cyclopropylethynyl)-6-fluoro-4-(trifluoromethyl)-3,4-dihydroquinazolin-2(1H)-one | 441 | B11 |
| 45 | 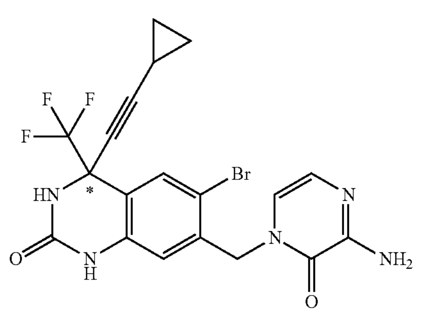 [SMILES: Nc1nccn(Cc2cc3c(cc2Br)C(C#CC2CC2)(C(F)(F)F)NC(=O)N3)c1=O] | (S)-7-((3-amino-2-oxopyrazin-1(2H)-yl)methyl)-6-bromo-4-(cyclopropylethynyl)-4-(trifluoromethyl)-3,4-dihydroquinazolin-2(1H)-one | 482, 484 | B18 |
| 46 | 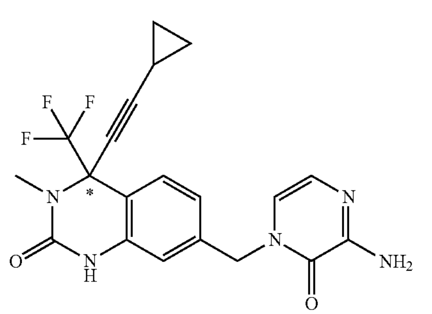 [SMILES: CN1C(=O)Nc2cc(Cn3ccnc(N)c3=O)ccc2C1(C#CC1CC1)C(F)(F)F] | (S)-7-((3-amino-2-oxopyrazin-1(2H)-yl)methyl)-4-(cyclopropylethynyl)-3-methyl-4-(trifluoromethyl)-3,4-dihydroquinazolin-2(1H)-one | 418 | B26 |

TABLE 1-continued

| Ex. | Structure | IUPAC Name | MS [M + 1] | INT. |
|---|---|---|---|---|
| 47 | 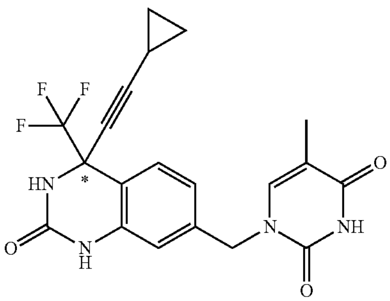 [SMILES: Cc1cn(Cc2ccc3c(c2)NC(=O)NC3(C#CC2CC2)C(F)(F)F)c(=O)[nH]c1=O] | (S)-1-((4-(cyclopropylethynyl)-2-oxo-4-(trifluoromethyl)-1,2,3,4-tetrahydroquinazolin-7-yl)methyl)-5-methylpyrimidine-2,4(1H,3H)-dione | 419 | B11 |
| 48 | 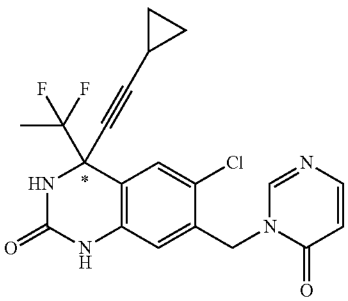 [SMILES: CC(F)(F)C1(C#CC2CC2)NC(=O)Nc2cc(Cn3cnccc3=O)c(Cl)cc21] | (S)-6-chloro-4-(cyclopropylethynyl)-4-(1,1-difluoroethyl)-7-((6-oxopyrimidin-1(6H)-yl)methyl)-3,4-dihydroquinazolin-2(1H)-one | 419 | B19 |
| 49 | 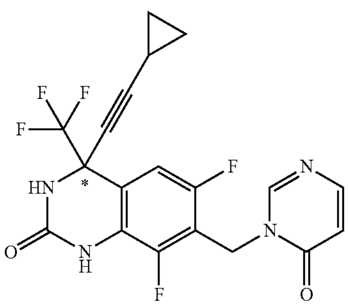 [SMILES: O=C1Nc2c(cc(F)c(Cn3cnccc3=O)c2F)C(C#CC2CC2)(C(F)(F)F)N1] | (S)-4-(cyclopropylethynyl)-6,8-difluoro-7-((6-oxopyrimidin-1(6H)-yl)methyl)-4-(trifluoromethyl)-3,4-dihydroquinazolin-2(1H)-one | 425 | B20 |
| 50 | 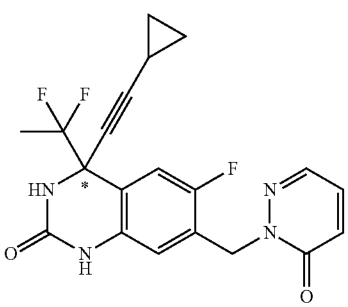 [SMILES: CC(F)(F)C1(C#CC2CC2)NC(=O)Nc2cc(Cn3ncccc3=O)c(F)cc21] | (S)-4-(cyclopropylethynyl)-4-(1,1-difluoroethyl)-6-fluoro-7-((6-oxopyridazin-1(6H)-yl)methyl)-3,4-dihydroquinazolin-2(1H)-one | 403 | B25 |
| 51 | 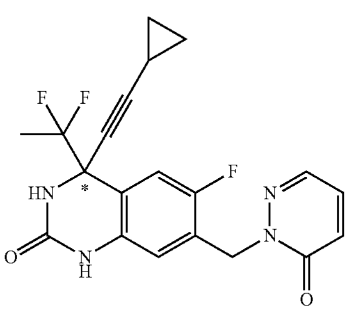 [SMILES: CC(F)(F)C1(C#CC2CC2)NC(=O)Nc2cc(Cn3ncccc3=O)c(F)cc21] | (S)-4-(cyclopropylethynyl)-4-(1,1-difluoroethyl)-6-fluoro-7-((3-methyl-6-oxopyridazin-1(6H)-yl)methyl)-3,4-dihydroquinazolin-2(1H)-one | 417 | B25 |

TABLE 1-continued

| Ex. | Structure | IUPAC Name | MS [M + 1] | INT. |
|---|---|---|---|---|
| 52 | 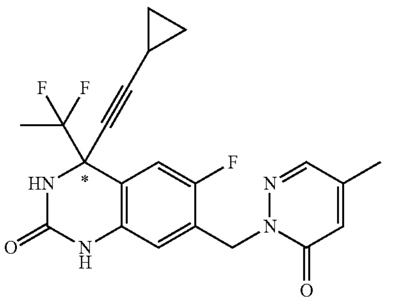 [SMILES: Cc1cnn(Cc2cc3c(cc2F)C(C#CC2CC2)(C(C)(F)F)NC(=O)N3)c(=O)c1] | (S)-4-(cyclopropylethynyl)-4-(1,1-difluoroethyl)-6-fluoro-7-((3-methyl-6-oxopyridazin-1(6H)-yl)methyl)-3,4-dihydroquinazolin-2(1H)-one | 417 | B25 |
| 53 | 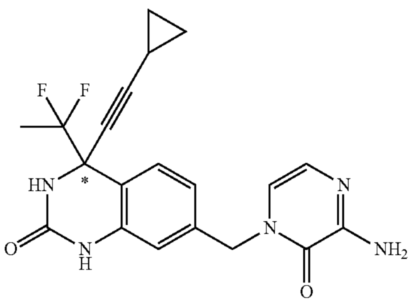 [SMILES: CC(F)(F)C1(C#CC2CC2)NC(=O)Nc2cc(Cn3ccnc(N)c3=O)ccc21] | (S)-7-((3-amino-2-oxopyrazin-1(2H)-yl)methyl)-4-(cyclopropylethynyl)-4-(1,1-difluoroethyl)-3,4-dihydroquinazolin-2(1H)-one | 400 | B14 |
| 54 | 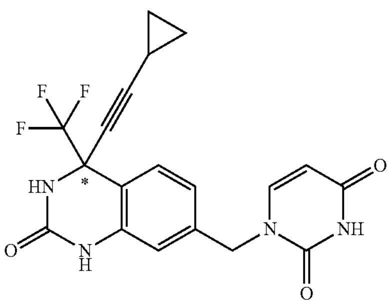 [SMILES: O=C1Nc2cc(Cn3ccc(=O)[nH]c3=O)ccc2C(C#CC2CC2)(C(F)(F)F)N1] | (S)-1-((4-(cyclopropylethynyl)-2-oxo-4-(trifluoromethyl)-1,2,3,4-tetrahydroquinazolin-7-yl)methyl)pyrimidine-2,4(1H,3H)-dione | 405 | B11 |
| 55 | 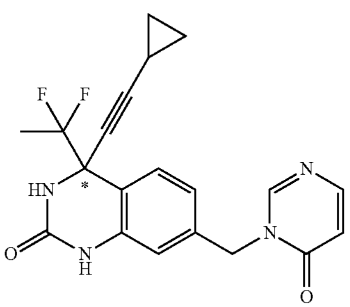 [SMILES: CC(F)(F)C1(C#CC2CC2)NC(=O)Nc2cc(Cn3cnccc3=O)ccc21] | (S)-4-(cyclopropylethynyl)-4-(1,1-difluoroethyl)-7-((6-oxopyrimidin-1(6H)-yl)methyl)-3,4-dihydroquinazolin-2(1H)-one | 385 | B14 |
| 56 | 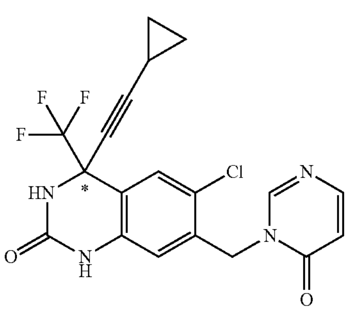 [SMILES: O=C1Nc2cc(Cn3cnccc3=O)c(Cl)cc2C(C#CC2CC2)(C(F)(F)F)N1] | (S)-6-chloro-4-(cyclopropylethynyl)-7-((6-oxopyrimidin-1(6H)-yl)methyl)-4-(trifluoromethyl)-3,4-dihydroquinazolin-2(1H)-one | 559 | B13 |

TABLE 1-continued

| Ex. | Structure | IUPAC Name | MS [M + 1] | INT. |
|---|---|---|---|---|
| 57 | 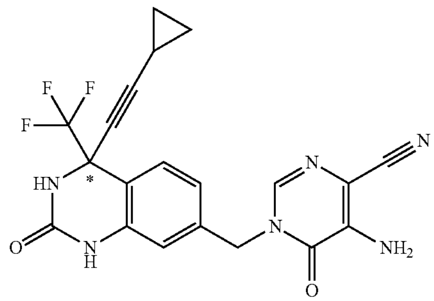 [SMILES: N#Cc1ncn(Cc2ccc3c(c2)NC(=O)NC3(C#CC2CC2)C(F)(F)F)c(=O)c1N] | (S)-5-amino-1-((4-(cyclopropylethynyl)-2-oxo-4-(trifluoromethyl)-1,2,3,4-tetrahydroquinazolin-7-yl)methyl)-6-oxo-1,6-dihydropyrimidine-4-carbonitrile | 429 | B11 |
| 58 | 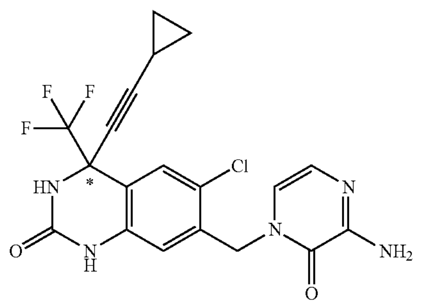 | (S)-7-((3-amino-2-oxopyrazin-1(2H)-yl)methyl)-6-chloro-4-(cyclopropylethynyl)-4-(trifluoromethyl)-3,4-dihydroquinazolin-2(1H)-one | 438 | B13 |
| 59 | 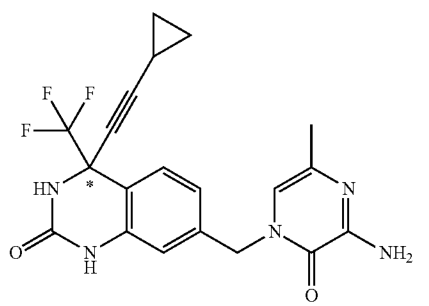 [SMILES: Cc1cn(Cc2ccc3c(c2)NC(=O)NC3(C#CC2CC2)C(F)(F)F)c(=O)c(N)n1] | (S)-7-((3-amino-5-methyl-2-oxopyrazin-1(2H)-yl)methyl)-4-(cyclopropylethynyl)-4-(trifluoromethyl)-3,4-dihydroquinazolin-2(1H)-one | 418 | B11, C04 |
| 60 | 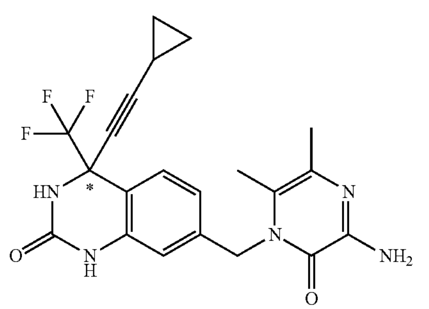 [SMILES: Cc1nc(N)c(=O)n(Cc2ccc3c(c2)NC(=O)NC3(C#CC2CC2)C(F)(F)F)c1C] | (S)-7-((3-amino-5,6-dimethyl-2-oxopyrazin-1(2H)-yl)methyl)-4-(cyclopropylethynyl)-4-(trifluoromethyl)-3,4-dihydroquinazolin-2(1H)-one | 432 | B11 |
| 61 | 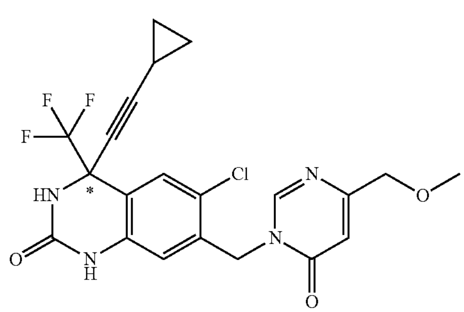 [SMILES: COCc1cc(=O)n(Cc2cc3c(cc2Cl)C(C#CC2CC2)(C(F)(F)F)NC(=O)N3)cn1] | (S)-6-chloro-4-(cyclopropylethynyl)-7-((4-(methoxymethyl)-6-oxopyrimidin-1(6H)-yl)methyl)-4-(trifluoromethyl)-3,4-dihydroquinazolin-2(1H)-one | 467 | B13 |

TABLE 1-continued

| Ex. | Structure | IUPAC Name | MS [M + 1] | INT. |
|---|---|---|---|---|
| 62 | 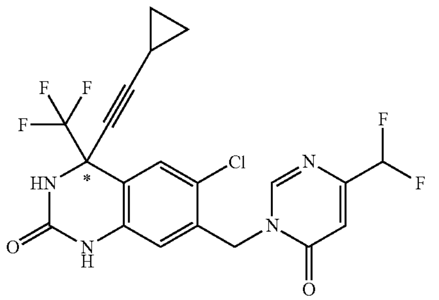 [SMILES: O=C1Nc2cc(Cn3cnc(C(F)F)cc3=O)c(Cl)cc2C(C#CC2CC2)(C(F)(F)F)N1] | (S)-6-chloro-4-(cyclopropylethynyl)-7-((4-(difluoromethyl)-6-oxopyrimidin-1(6H)-yl)methyl)-4-(trifluoromethyl)-3,4-dihydroquinazolin-2(1H)-one | 473 | B13 |
| 63 | 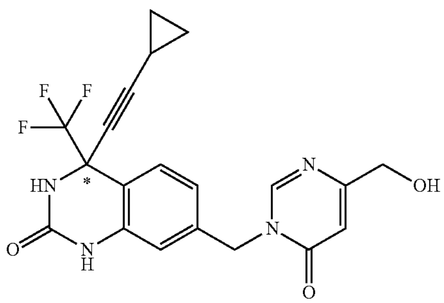 [SMILES: O=C1Nc2cc(Cn3cnc(CO)cc3=O)ccc2C(C#CC2CC2)(C(F)(F)F)N1] | (S)-4-(cyclopropylethynyl)-7-((4-(hydroxymethyl)-6-oxopyrimidin-1(6H)-yl)methyl)-4-(trifluoromethyl)-3,4-dihydroquinazolin-2(1H)-one | 419 | B11 |
| 64 | 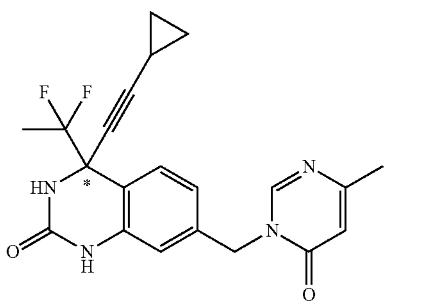 [SMILES: Cc1cc(=O)n(Cc2ccc3c(c2)NC(=O)NC3(C#CC2CC2)C(C)(F)F)cn1] | (S)-4-(cyclopropylethynyl)-4-(1,1-difluoroethyl)-7-((4-methyl-6-oxopyrimidin-1(6H)-yl)methyl)-3,4-dihydroquinazolin-2(1H)-one | 399 | B14 |
| 65 | 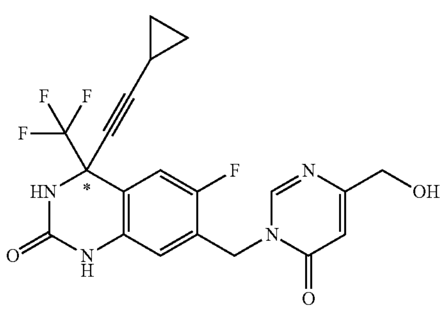 [SMILES: O=C1Nc2cc(Cn3cnc(CO)cc3=O)c(F)cc2C(C#CC2CC2)(C(F)(F)F)N1] | (S)-4-(cyclopropylethynyl)-6-fluoro-7-((4-(hydroxymethyl)-6-oxopyrimidin-1(6H)-yl)methyl)-4-(trifluoromethyl)-3,4-dihydroquinazolin-2(1H)-one | 437 | B12, C05 |
| 66 | 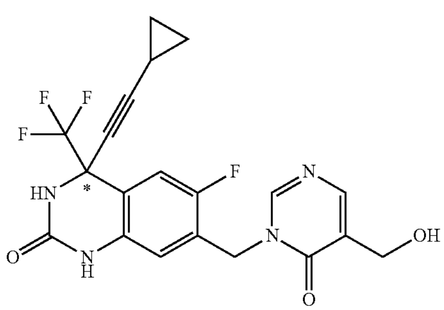 [SMILES: O=C1Nc2cc(Cn3cncc(CO)c3=O)c(F)cc2C(C#CC2CC2)(C(F)(F)F)N1] | (S)-4-(cyclopropylethynyl)-6-fluoro-7-((5-(hydroxymethyl)-6-oxopyrimidin-1(6H)-yl)methyl)-4-(trifluoromethyl)-3,4-dihydroquinazolin-2(1H)-one | 437 | B12, C06 |

TABLE 1-continued

| Ex. | Structure | IUPAC Name | MS [M + 1] | INT. |
|---|---|---|---|---|
| 67 | 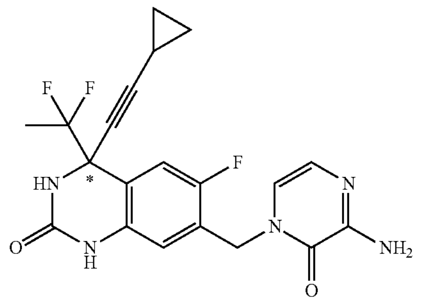 [SMILES: CC(F)(F)C1(C#CC2CC2)NC(=O)Nc2cc(Cn3ccnc(N)c3=O)c(F)cc21] | (S)-7-((3-amino-2-oxopyrazin-1(2H)-yl)methyl)-4-(cyclopropylethynyl)-4-(1,1-difluoroethyl)-6-fluoro-3,4-dihydroquinazolin-2(1H)-one | 418 | B25 |
| 68 | 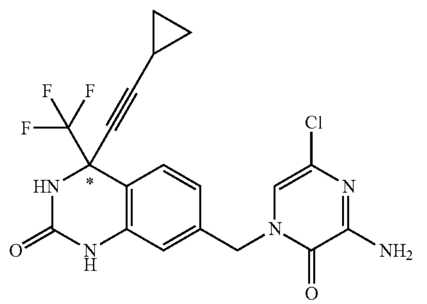 | (S)-7-((3-amino-5-chloro-2-oxopyrazin-1(2H)-yl)methyl)-4-(cyclopropylethynyl)-4-(trifluoromethyl)-3,4-dihydroquinazolin-2(1H)-one | 438 | B11, C07 |
| 69 | 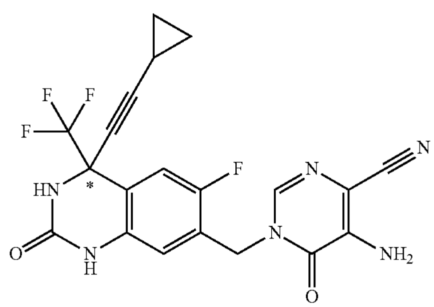 [SMILES: N#Cc1ncn(Cc2cc3c(cc2F)C(C#CC2CC2)(C(F)(F)F)NC(=O)N3)c(=O)c1N] | (S)-5-amino-1-((4-(cyclopropylethynyl)-6-fluoro-2-oxo-4-(trifluoromethyl)-1,2,3,4-tetrahydroquinazolin-7-yl)methyl)-6-oxo-1,6-dihydropyrimidine-4-carbonitrile | 447 | B12, C01 |
| 70 | 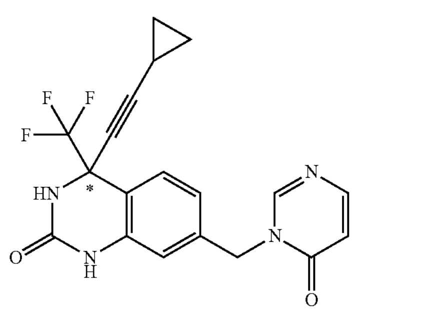 [SMILES: O=C1Nc2cc(Cn3cnccc3=O)ccc2C(C#CC2CC2)(C(F)(F)F)N1] | (S)-3-((4-(cyclopropylethynyl)-2-thioxo-4-(trifluoromethyl)-1,2,3,4-tetrahydroquinazolin-7-yl)methyl)pyrimidin-4(3H)-one | 405 | B25 |
| 71 | 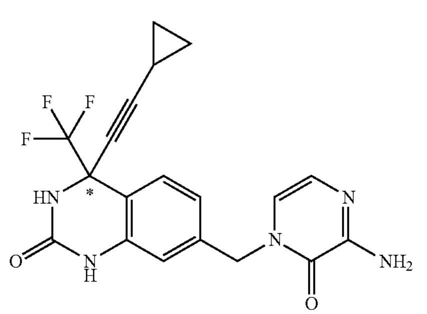 | (S)-3-amino-1-((4-(cyclopropylethynyl)-2-thioxo-4-(trifluoromethyl)-1,2,3,4-tetrahydroquinazolin-7-yl)methyl)pyrazin-2(1H)-one | 420 | B25 |

Example 72: (S)-7-((3-amino-2-oxo-4-(trifluoromethyl)pyridin-1(2H)-yl)methyl)-4-(cyclopropylethynyl)-4-(trifluoromethyl)-3,4-dihydroquinazolin-2(1H)-one

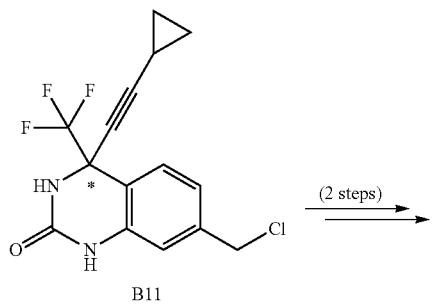

B11

(2 steps) →

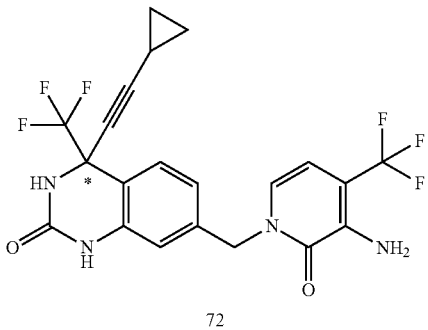

72

Step 1: (S)-4-(cyclopropylethynyl)-7-((3-fluoro-2-oxo-4-(trifluoromethyl)pyridin-1(2H)-yl)methyl)-4-(trifluoromethyl)-3,4-dihydroquinazolin-2(1H)-one: Intermediate B11 (150 mg, 0.46 mmol) was dissolved in DMF (2.2 mL) and 3-fluoro-4-(trifluoromethyl)pyridin-2(1H)-one (99 mg, 0.55 mmol) was added followed by $K_2CO_3$ (252 mg, 1.82 mmol). The resulting mixture was stirred at 25° C. for 16 h. The reaction mixture was diluted with EtOAc (20 mL) and washed with water (2×5 mL). The organic layer was dried over $MgSO_4$, filtered and concentrated. The resulting residue was purified by flash chromatography ($SiO_2$, (3:1 EtOAc:EtOH):hexanes) to provide the title compound. MS (ESI) m/z 474 [M+1].

Step 2: (S)-7-((3-amino-2-oxo-4-(trifluoromethyl)pyridin-1(2H)-yl)methyl)-4-(cyclopropylethynyl)-4-(trifluoromethyl)-3,4-dihydroquinazolin-2(H)-one: (S)-4-(cyclopropylethynyl)-7-((3-fluoro-2-oxo-4-(trifluoromethyl)pyridin-1(2H)-yl)methyl)-4-(trifluoromethyl)-3,4-dihydroquinazolin-2(1H)-one (55 mg, 0.12 mmol) was dissolved in THF (1.2 mL) and $NH_3$ in MeOH (3 mL, 21.0 mmol) was added. The resulting mixture was heated to 50° C. for 16 h. The reaction was concentrated and the crude was purified by prep-HPLC (MeCN:water with 0.1% TFA) to provide the title compound. $^1H$ NMR (500 MHz, DMSO-$d_6$) δ 9.69 (s, 1H), 8.34 (s, 1H), 7.40 (d, J=8.0 Hz, 1H), 7.07 (d, J=7.3 Hz, 1H), 6.90 (d, J=8.2 Hz, 1H), 6.72 (s, 1H), 6.25 (d, J=7.4 Hz, 1H), 6.01 (s, 2H), 5.10 (s, 2H), 1.53-1.38 (m, 1H), 0.86 (dd, J=8.2, 2.7 Hz, 2H), 0.71 (dd, J=7.7, 4.9 Hz, 2H) ppm. MS (ESI) m/z 471 [M+1].

Example 73: (S)-4-(cyclopropylethynyl)-3-methyl-7-((6-oxopyrimidin-1(6H)-yl)methyl)-4-(trifluoromethyl)-3,4-dihydroquinazolin-2(1H)-one

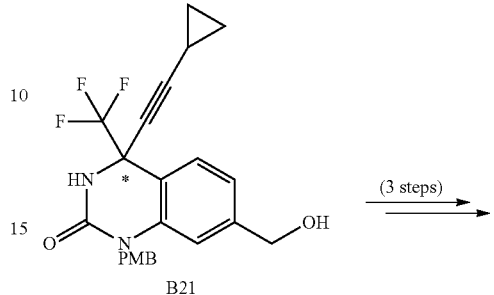

B21

(3 steps) →

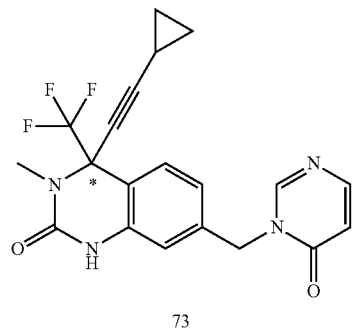

73

Step 1: (S)-4-(cyclopropylethynyl)-1-(4-methoxybenzyl)-7-((6-oxopyrimidin-1(6H)-yl)methyl)-4-(trifluoromethyl)-3,4-dihydroquinazolin-2(1H)-one: To a mixture of intermediate B21 (216 mg, 0.502 mmol), pyrimidin-4(3H)-one (62.7 mg, 0.652 mmol), and $PPh_3$ (171 mg, 0.652 mmol) in DCM (5.0 mL), was added di-tert-butyl azodicarboxylate (150 mg, 0.652 mmol) in DCM (5.0 mL) dropwise. The resulting mixture was stirred at 25° C. for 1 h. The mixture was concentrated, and the residue was purified with flash chromatography ($SiO_2$, 0-100% EtOAc/hexanes) to afford the title compound. MS (ESI) m/z 509.4 [M+1].

Step 2: (S)-4-(cyclopropylethynyl)-1-(4-methoxybenzyl)-3-methyl-7-((6-oxopyrimidin-1(6H)-yl)methyl)-4-(trifluoromethyl)-3,4-dihydroquinazolin-2(1H)-one: A solution of (S)-4-(cyclopropylethynyl)-1-(4-methoxybenzyl)-7-((6-oxopyrimidin-1(6H)-yl)methyl)-4-(trifluoromethyl)-3,4-dihydroquinazolin-2(1H)-one (29 mg, 0.057 mmol) in anhydrous 1,4-dioxane (500 μL, was treated with 60% NaH dispersion in mineral oil (6.84 mg, 0.171 mmol). After bubbling stopped, MeI (17.83 μL, 0.285 mmol) was added dropwise. The resulting mixture was stirred at 25° C. for 16 h. The reaction was quenched with water, then extracted with EtOAc (3×). The combined organic layer was dried over $Na_2SO_4$, filtered and concentrated to afford the title compound. MS (ESI) m/z 523.4 [M+1].

Step 3: (S)-4-(cyclopropylethynyl)-3-methyl-7-((6-oxopyrimidin-1(6H)-yl)methyl)-4-(trifluoromethyl)-3,4-dihydroquinazolin-2(1H)-one: To a mixture of (S)-4-(cyclopropylethynyl)-1-(4-methoxybenzyl)-3-methyl-7-((6-oxopyrimidin-1(6H)-yl)methyl)-4-(trifluoromethyl)-3,4-dihydroquinazolin-2(1H)-one (31.4 mg, 0.06 mmol) in MeCN (0.5 mL) and water (0.1 mL), was added CAN (164 mg, 0.3 mmol). The resulting mixture was stirred at 25° C. for 3 h. The crude mixture was purified by prep-HPLC (water:MeCN with 0.1% TFA) to afford the title compound. $^1H$ NMR (600 MHz, $CDCl_3$) δ 8.23 (d, J=17.7 Hz, 2H), 7.90

(d, J=6.6 Hz, 1H), 7.56 (d, J=8.0 Hz, 1H), 6.99 (d, J=8.1 Hz, 1H), 6.75 (s, 1H), 6.53 (d, J=6.6 Hz, 1H), 5.08 (s, 2H), 3.27 (s, 3H), 1.39 (ddd, J=5.0, 8.3, 13.3 Hz, 1H), 0.95-0.86 (m, 2H), 0.85-0.78 (m, 2H) ppm. MS (ESI) m/z 403.3 [M+1].

Example 74: (S)-4-(cyclopropylethynyl)-3-ethyl-7-((6-oxopyrimidin-1(6H)-yl)methyl)-4-(trifluoromethyl)-3,4-dihydroquinazolin-2(1H)-one

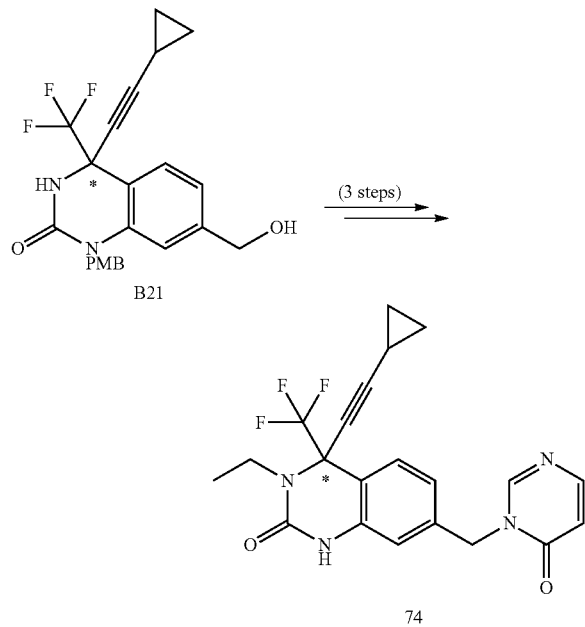

Example 74 was prepared using a procedure analogous to Example 73 except that methyl iodide was replaced by ethyl iodide. ¹H NMR (600 MHz, CDCl₃) δ 8.20 (s, 1H), 7.89 (d, J=6.7 Hz, 1H), 7.75 (s, 1H), 7.57 (d, J=8.1 Hz, 1H), 6.98 (d, J=8.0 Hz, 1H), 6.71 (s, 1H), 6.51 (d, J=6.6 Hz, 1H), 5.07 (s, 2H), 4.00 (dq, J=6.9, 13.9 Hz, 1H), 3.62 (dt, J=6.9, 14.1 Hz, 1H), 1.40 (ddd, J=5.1, 8.3, 13.3 Hz, 1H), 1.22 (t, J=7.0 Hz, 3H), 0.91 (ddd, J=2.0, 3.9, 8.2 Hz, 2H), 0.80 (dq, J=3.0, 4.1, 6.0 Hz, 2H). MS (ESI) m/z 417.3 [M+1].

Example 75: (S)-4-(cyclopropylethynyl)-2-oxo-7-((6-oxopyrimidin-1(6H)-yl)methyl)-4-(trifluoromethyl)-1,2,3,4-tetrahydroquinazoline-6-carbonitrile and (R)-4-(cyclopropylethynyl)-2-oxo-7-((6-oxopyrimidin-1(6H)-yl)methyl)-4-(trifluoromethyl)-1,2,3,4-tetrahydroquinazoline-6-carbonitrile

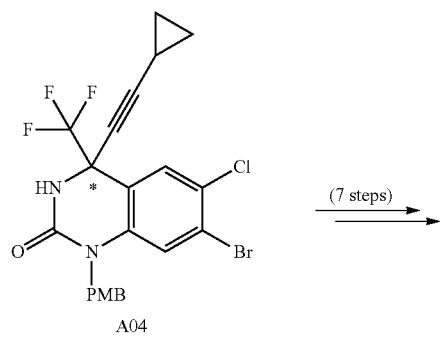

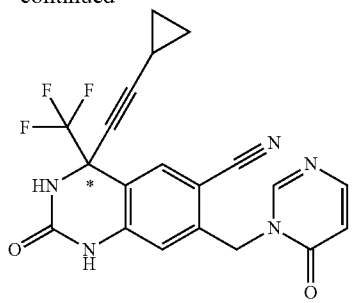

75-Isomer A and
75-Isomer B

Step 1: 6-chloro-4-(cyclopropylethynyl)-1-(4-methoxybenzyl)-4-(trifluoromethyl)-7-vinyl-3,4-dihydroquinazolin-2(1H)-one: To a solution of intermediate A04 (6.0 g, 11.7 mmol) and potassium trifluoro(vinyl)borate (2.35 g, 17.5 mmol) in 1,4-dioxane (60 mL) and water (6 mL) was added K₂CO₃ (4.84 g, 35.0 mmol) and PdCl₂(dppf) (0.85 g, 1.17 mmol), then the reaction mixture was stirred at 100° C. for 3 h. The reaction mixture was poured into H₂O (300 mL) and extracted with EtOAc (3×180 mL). The combined organic phase was washed with brine (500 mL), filtered and concentrated. The crude was purified by flash chromatography (SiO₂, 0-30% EtOAc/PE) to provide the title compound. MS (ESI) m/z 461.1 [M+1].

Step 2: 6-chloro-4-(cyclopropylethynyl)-1-(4-methoxybenzyl)-2-oxo-4-(trifluoromethyl)-1,2,3,4-tetrahydroquinazoline-7-carbaldehyde: To a stirred solution of 6-chloro-4-(cyclopropylethynyl)-1-(4-methoxybenzyl)-4-(trifluoromethyl)-7-vinyl-3,4-dihydroquinazolin-2(1H)-one (4.5 g, 9.76 mmol) in 1,4-dioxane (104 mL) and water (34 mL) were added 2,6-lutidine (3.14 g, 29.3 mmol) and potassium osmate(VI) dihydrate (0.720 g, 1.953 mmol). The mixture was stirred at 20° C. for 10 min and then, NaIO₄ (8.35 g, 39.1 mmol) was added and the resulting mixture was stirred at 20° C. for 16 h. The reaction was quenched with water (180 mL) and extracted with EtOAc (3×50 mL). The combined organic layer was washed with brine, dried over Na₂SO₄, filtered, concentrated and purified by flash chromatography (SiO₂, 0-30% EtOAc/PE) to afford the title compound. MS (ESI) m/z 463.2 [M+1].

Step 3: 6-chloro-4-(cyclopropylethynyl)-7-(hydroxymethyl)-1-(4-methoxybenzyl)-4-(trifluoromethyl)-3,4-dihydroquinazolin-2(1H)-one: To a solution of 6-chloro-4-(cyclopropylethynyl)-1-(4-methoxybenzyl)-2-oxo-4-(trifluoromethyl)-1,2,3,4-tetrahydroquinazoline-7-carbaldehyde (0.9 g, 1.944 mmol) in MeOH (10 mL) was added NaBH(OAc)₃ (2.473 g, 11.67 mmol) at 25° C. Then, the reaction was stirred at 25° C. for 4 h. The reaction was washed with H₂O (50 mL) and extracted with EtOAc (3×15 mL). The combined organic layer was concentrated to give the title compound, which was used directly without further purification. MS (ESI) m/z 465.2 [M+1].

Step 4: 6-chloro-7-(chloromethyl)-4-(cyclopropylethynyl)-1-(4-methoxybenzyl)-4-(trifluoromethyl)-3,4-dihydroquinazolin-2(1H)-one: A mixture of 6-chloro-4-(cyclopropylethynyl)-7-(hydroxymethyl)-1-(4-methoxybenzyl)-4-(trifluoromethyl)-3,4-dihydroquinazolin-2(1H)-one (450 mg, 0.968 mmol) and DIPEA (0.845 mL, 4.84 mmol) in DCM (5 mL) was added MsCl (0.226 mL, 2.90 mmol). The mixture was stirred at 20° C. for 15 h. The mixture was purified by prep-TLC (25% EtOAc:PE) to give the title compound.

Step 5: 6-chloro-4-(cyclopropylethynyl)-1-(4-methoxybenzyl)-7-((6-oxopyrimidin-1(6H)-yl)methyl)-4-(trifluoromethyl)-3,4-dihydroquinazolin-2(1H)-one: A mixture of 6-chloro-7-(chloromethyl)-4-(cyclopropylethynyl)-1-(4-methoxybenzyl)-4-(trifluoromethyl)-3,4-dihydroquinazolin-2(1H)-one (492 mg, 1.018 mmol), pyrimidin-4(3H)-one (98 mg, 1.018 mmol), K$_2$CO$_3$ (422 mg, 3.05 mmol) and LiBr (177 mg, 2.036 mmol) in DMF (4 mL) was stirred at 20° C. for 16 h. The mixture was diluted with water (20 mL) and extracted with EtOAc (15 mL×2). The combined organic layer was washed with brine (3×45 mL), dried with Na$_2$SO$_4$ and concentrated. The crude was purified by prep-TLC (EtOAc) give the title compound. MS (ESI) m/z 543.2 [M+1].

Step 6: 4-(cyclopropylethynyl)-1-(4-methoxybenzyl)-2-oxo-7-((6-oxopyrimidin-1(6H)-yl)methyl)-4-(trifluoromethyl)-1,2,3,4-tetrahydroquinazoline-6-carbonitrile: To a solution of 6-chloro-4-(cyclopropylethynyl)-1-(4-methoxybenzyl)-7-((6-oxopyrimidin-1(6H)-yl)methyl)-4-(trifluoromethyl)-3,4-dihydroquinazolin-2(1H)-one (300 mg, 0.553 mmol) in water (0.4 mL) and 1,4-dioxane (4 mL) was added K$_2$CO$_3$ (153 mg, 1.105 mmol), Pd(OAc)$_2$ (31.0 mg, 0.138 mmol) and X-Phos (132 mg, 0.276 mmol). The reaction was stirred at 120° C. for 10 h. Then, the reaction mixture was directly purified by prep-TLC (EtOAc) to give the title compound.

Step 7: (S)-4-(cyclopropylethynyl)-2-oxo-7-((6-oxopyrimidin-1(6H)-yl)methyl)-4-(trifluoromethyl)-1,2,3,4-tetrahydroquinazoline-6-carbonitrile AND (R)-4-(cyclopropylethynyl)-2-oxo-7-((6-oxopyrimidin-1(6H)-yl)methyl)-4-(trifluoromethyl)-1,2,3,4-tetrahydroquinazoline-6-carbonitrile: To a stirred solution of 4-(cyclopropylethynyl)-1-(4-methoxybenzyl)-2-oxo-7-((6-oxopyrimidin-1(6H)-yl)methyl)-4-(trifluoromethyl)-1,2,3,4-tetrahydroquinazoline-6-carbonitrile (117 mg, 0.219 mmol) in MeCN (1 mL) and water (0.33 mL) was added CAN (313 mg, 0.570 mmol) and the resulting mixture was stirred at 40° C. for 1 h. The reaction was dissolved in H$_2$O (10 mL). The residue was extracted with EtOAc (3×10 mL). The combined organic layer was washed with brine (30 mL), dried over (Na$_2$SO$_4$), filtered and concentrated. The crude product was purified by prep-HPLC (MeCN:water with 0.1% TFA) and the racemic mixture was separated by SFC (Chiralcel OJ; 45% MeOH (0.1% NH$_3$H$_2$O)/CO$_2$; 70 g/min; 40° C.; 100 bar) to give: Isomer A (faster eluting): $^1$H NMR (400 MHz, MeOH-d$_4$): δ ppm 8.60 (s, 1H), 8.03 (d, J=6.8 Hz, 1H), 7.86 (s, 1H), 6.78 (s, 1H), 6.54 (d, J=6.6 Hz, 1H), 5.34 (s, 2H), 1.46 (br t, J=4.8 Hz, 1H), 0.92 (dd, J=7.8, 2.5 Hz, 2H), 0.80 (br s, 2H). MS (ESI) m/z 414.1 [M+1]; and Isomer B (slower eluting): $^1$H NMR (400 MHz, MeOH-d$_4$): δ ppm 8.60 (s, 1H), 8.03 (d, J=6.6 Hz, 1H), 7.87 (s, 1H), 6.78 (s, 1H), 6.54 (d, J=6.6 Hz, 1H), 5.34 (s, 2H), 1.15 (d, J=6.2 Hz, 1H), 0.89-0.97 (m, 2H), 0.76-0.84 (m, 2H). MS (ESI) m/z 414.1 [M+1].

Example 76: (S)-7-((3-amino-2-oxopyrazin-1(2H)-yl)methyl)-6-chloro-4-(cyclopropylethynyl)-3-methyl-4-(trifluoromethyl)-3,4-dihydroquinazolin-2 (1H)-one and (R)-7-((3-amino-2-oxopyrazin-1(2H)-yl)methyl)-6-chloro-4-(cyclopropylethynyl)-3-methyl-4-(trifluoromethyl)-3,4-dihydroquinazolin-2 (1H)-one

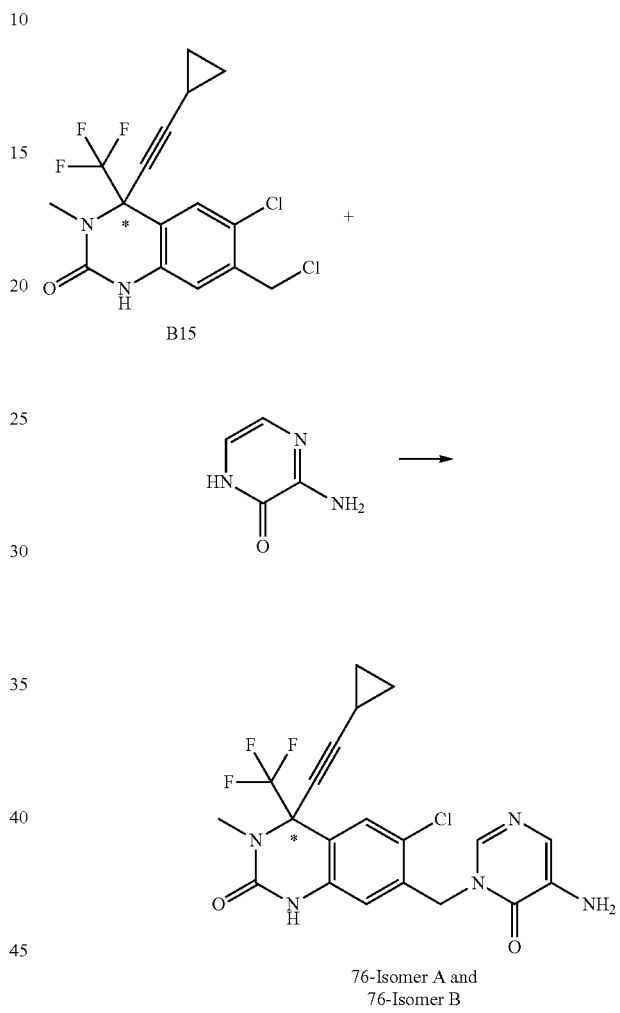

76-Isomer A and
76-Isomer B

Example 76 was prepared using a procedure analogous to Example 1 except that intermediate B12 was replaced by intermediate B15 and pyrimidin-4(3H)-one was replaced by 3-aminopyrazin-2(1H)-one and reaction was stirred at 50° C. for 2 h in DMF with LiBr (2 equiv). The racemic product was separated by SFC (WHELK-01; 55% EtOH (0.1% NH$_3$H$_2$O)/CO$_2$; 80 g/min; 40° C.; 100 bar) to give the title products: Isomer A (faster eluting): $^1$H NMR (400 MHz, MeOH-d$_4$) δ=7.58 (s, 1H), 6.80-6.75 (m, 2H), 6.58 (s, 1H), 5.17 (d, J=2.8 Hz, 2H), 3.21 (s, 3H), 1.59-1.49 (m, 1H), 1.02-0.96 (m, 2H), 0.85-0.80 (m, 2H). MS (ESI) m/z 452.1 [M+1]; and Isomer B (slower eluting): $^1$H NMR (400 MHz, MeOH-d$_4$) δ=7.58 (s, 1H), 6.80-6.75 (m, 2H), 6.58 (s, 1H), 5.17 (d, J=3.0 Hz, 2H), 3.21 (s, 3H), 1.57-1.50 (m, 1H), 1.01-0.96 (m, 2H), 0.85-0.80 (m, 2H). MS (ESI) m/z 452.1 [M+1].

Example 77: (S)-4-(3-methylbut-1-yn-1-yl)-7-((6-oxopyrimidin-1(6H)-yl)methyl)-4-(trifluoromethyl)-3,4-dihydroquinazolin-2(1H)-one and (R)-4-(3-methylbut-1-yn-1-yl)-7-((6-oxopyrimidin-1(6H)-yl)methyl)-4-(trifluoromethyl)-3,4-dihydroquinazolin-2(1H)-one Example 78: (S)-6-chloro-4-(cyclopropylethynyl)-3-methyl-7-((6-oxopyrimidin-1(6H)-yl)methyl)-4-(trifluoromethyl)-3,4-dihydroquinazolin-2(1H)-one and (R)-6-chloro-4-(cyclopropylethynyl)-3-methyl-7-((6-oxopyrimidin-1(6H)-yl)methyl)-4-(trifluoromethyl)-3,4-dihydroquinazolin-2(1H)-one

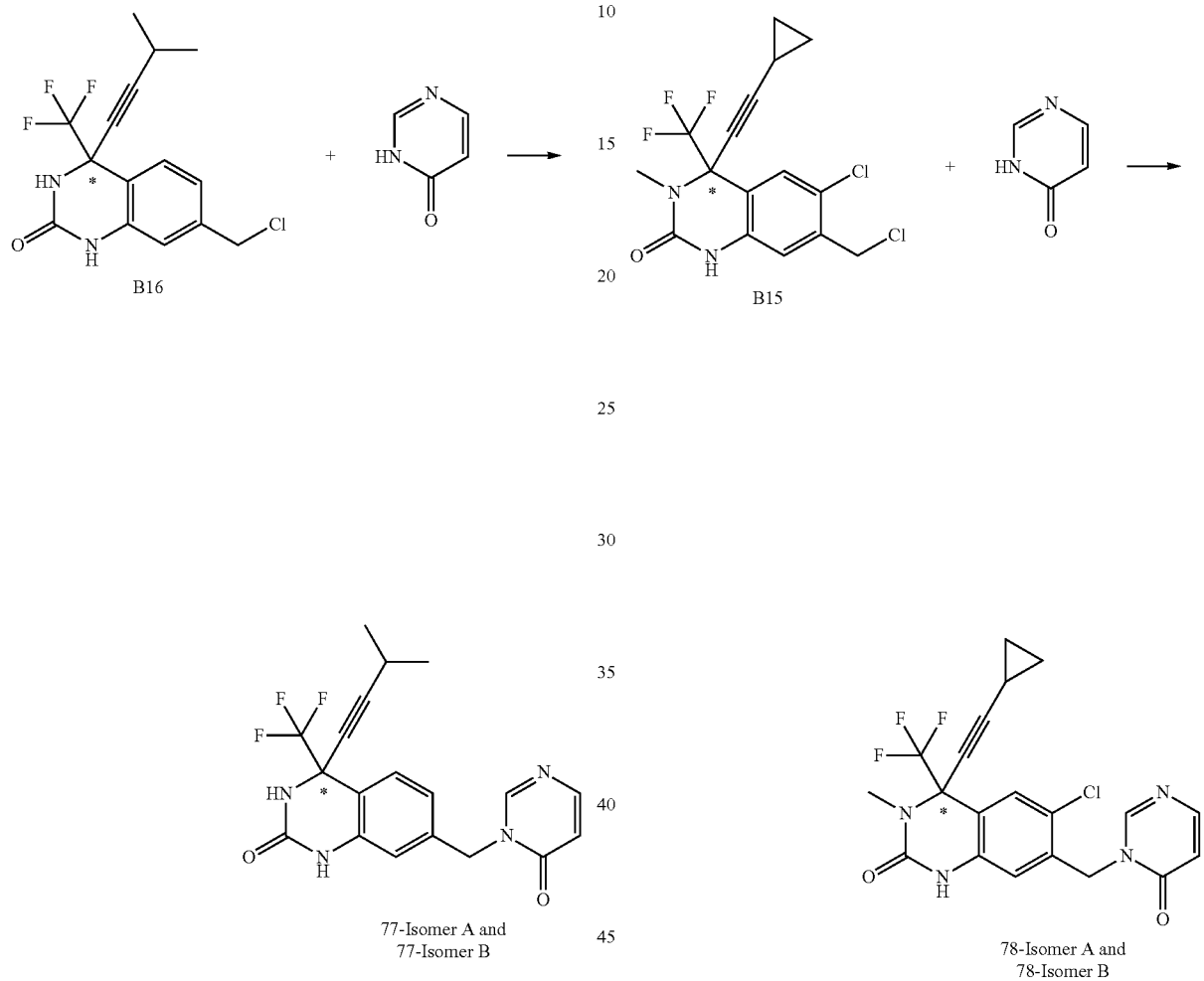

Example 77 was prepared using a procedure analogous to Example 1 except that intermediate B12 was replaced by intermediate B16 and reaction was stirred at 15° C. for 16 h in DMF with LiBr (2 equiv). The racemic product was separated by SFC (Chiralpak AD; 52% EtOH (0.1% $NH_3H_2O$)/$CO_2$; 70 g/min; 40° C.; 100 bar) to give the title products: Isomer A (faster eluting): $^1$H NMR (400 MHz, DMSO-$d_6$) δ ppm 9.71 (s, 1H), 8.64 (s, 1H), 8.39 (s, 1H), 7.96 (d, J=6.6 Hz, 1H), 7.43 (d, J=7.9 Hz, 1H), 6.93 (d, J=8.4 Hz, 1H), 6.75 (s, 1H), 6.45 (d, J=6.62 Hz, 1H), 5.07 (s, 2H), 2.69 (dt, J=13.8, 6.8 Hz, 1H), 1.16 (dd, J=6.8, 3.1 Hz, 6H). MS (ESI) m/z 391.0 [M+1]; and Isomer B (slower eluting): $^1$H NMR (400 MHz, DMSO-$d_6$) δ ppm 9.70 (s, 1H), 8.63 (s, 1H), 8.39 (s, 1H), 7.96 (d, J=6.6 Hz, 1H), 7.42 (d, J=7.9 Hz, 1H), 6.93 (d, J=8.2 Hz, 1H), 6.75 (s, 1H), 6.45 (d, J=6.8 Hz, 1H), 5.06 (s, 2H), 2.69 (dt, J=13.8, 6.8 Hz, 1H), 1.15 (dd, J=6.8, 3.1 Hz, 6H). MS (ESI) m/z 391.1 [M+1].

Example 78 was prepared using a procedure analogous to Example 1 except that intermediate B12 was replaced by intermediate B15 and reaction was stirred at 50° C. for 2 h in DMF with LiBr (2 equiv). The racemic product was separated by SFC (DAICEL CHIRALPAK AD-H; 45% EtOH (0.1% $NH_3H_2O$)/$CO_2$; 65 g/min; 40° C.; 100 bar) to give the title products: Isomer A (faster eluting): $^1$H NMR (400 MHz, MeOH-$d_4$) δ=8.53 (s, 1H), 8.02 (d, J=6.8 Hz, 1H), 7.58 (s, 1H), 6.67 (s, 1H), 6.54 (d, J=6.6 Hz, 1H), 5.32-5.17 (m, 2H), 3.22 (s, 3H), 1.60-1.48 (m, 1H), 1.03-0.93 (m, 2H), 0.86-0.75 (m, 2H). MS (ESI) m/z 437.0 [M+1]; and Isomer B (slower eluting): $^1$H NMR (400 MHz, MeOH-$d_4$) δ=8.53 (s, 1H), 8.01 (d, J=6.6 Hz, 1H), 7.58 (s, 1H), 6.67 (s, 1H), 6.53 (d, J=6.6 Hz, 1H), 5.30-5.19 (m, 2H), 3.21 (s, 3H), 1.58-1.49 (m, 1H), 1.02-0.94 (m, 2H), 0.86-0.78 (m, 2H). MS (ESI) m/z 437.0 [M+1].

Example 79: (S)-4-(4-methylpent-1-yn-1-yl)-7-((6-oxopyrimidin-1(6H)-yl)methyl)-4-(trifluoromethyl)-3,4-dihydroquinazolin-2(1H)-one and (R)-4-(4-methylpent-1-yn-1-yl)-7-((6-oxopyrimidin-1(6H)-yl)methyl)-4-(trifluoromethyl)-3,4-dihydroquinazolin-2(1H)-one

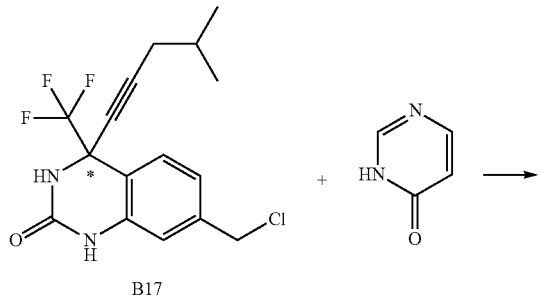

B17

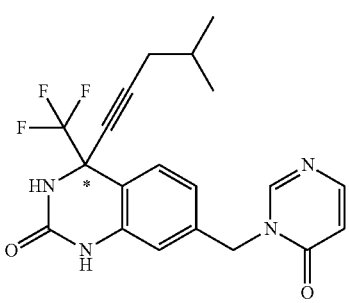

79-Isomer A and
79-Isomer B

Example 79 was prepared using a procedure analogous to Example 1 except that intermediate B12 was replaced by intermediate B17 and reaction was stirred at 50° C. for 2 h in DMF with LiBr (2 equiv). The racemic product was separated by SFC (DAICEL CHIRALCEL OD; 25% EtOH (0.1% NH$_3$H$_2$O)/CO$_2$; 60 mL/min; 40° C.; 100 bar) to give the title products: Isomer A (faster eluting): $^1$H NMR (400 MHz, DMSO-d$_6$) δ=9.71 (s, 1H), 8.64 (s, 1H), 8.45 (s, 1H), 7.96 (d, J=6.5 Hz, 1H), 7.43 (d, J=8.0 Hz, 1H), 6.94 (d, J=8.1 Hz, 1H), 6.75 (s, 1H), 6.45 (d, J=6.6 Hz, 1H), 5.07 (s, 2H), 2.23 (d, J=6.4 Hz, 2H), 1.82 (quint, J=6.5, 13.1 Hz, 1H), 0.96 (d, J=6.6 Hz, 6H). MS (ESI) m/z 405.1 [M+1]; and Isomer B (slower eluting): $^1$H NMR (400 MHz, DMSO-d$_6$) δ=9.71 (s, 1H), 8.64 (s, 1H), 8.45 (s, 1H), 7.96 (d, J=6.5 Hz, 1H), 7.43 (d, J=8.0 Hz, 1H), 6.94 (d, J=8.1 Hz, 1H), 6.75 (s, 1H), 6.45 (d, J=6.6 Hz, 1H), 5.07 (s, 2H), 2.23 (d, J=6.4 Hz, 2H), 1.82 (quint, J=6.5, 13.1 Hz, 1H), 0.96 (d, J=6.6 Hz, 6H). MS (ESI) m/z 405.1 [M+1].

Example 80: (S)-4-(cyclopropylethynyl)-6-methyl-7-((6-oxopyrimidin-1(6H)-yl)methyl)-4-(trifluoromethyl)-3,4-dihydroquinazolin-2(1H)-one

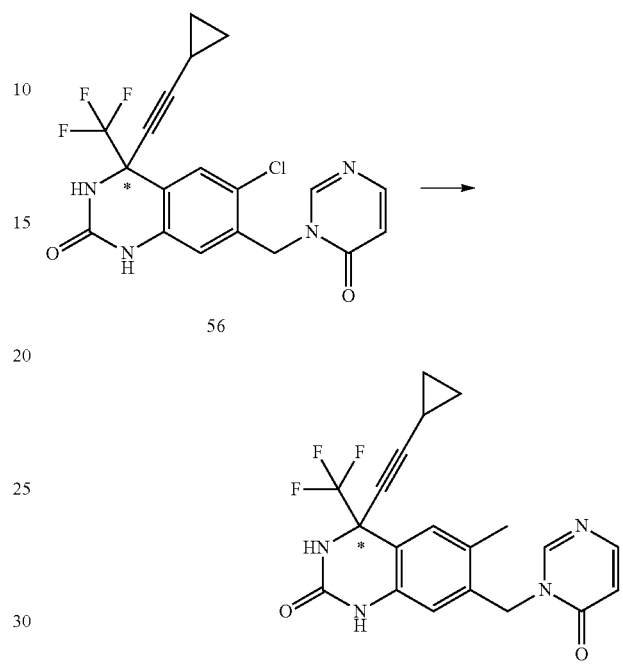

To a mixture of Example 56 (50 mg, 0.118 mmol) and trimethylboroxine (0.165 mL, 0.591 mmol) in THF (2 mL) and water (0.2 mL) was added K$_3$PO$_4$ (50.2 mg, 0.237 mmol) and XPhos Pd G2 (9.30 mg, 0.012 mmol) under N$_2$. The mixture was stirred at 90° C. for 15 h. Then, the mixture was filtered and purified by prep-HPLC (water:MeCN with 0.1% TFA) to give the title product. $^1$H NMR (400 MHz, MeOH-d$_4$) δ ppm 0.73-0.79 (m, 2H), 0.85-0.93 (m, 2H), 1.37-1.47 (m, 1H), 2.38 (s, 3H), 5.18 (s, 2H), 6.43 (s, 1H), 6.56 (d, J=6.6 Hz, 1H), 7.36 (s, 1H), 8.03 (d, J=6.7 Hz, 1H), 8.46 (s, 1H). MS (ESI) m/z 403.1 [M+1].

Example 81: (S)-7-((5-amino-4-(1,1-difluoroethyl)-6-oxopyrimidin-1(6H)-yl)methyl)-4-(cyclopropylethynyl)-4-(trifluoromethyl)-3,4-dihydroquinazolin-2(1H)-one

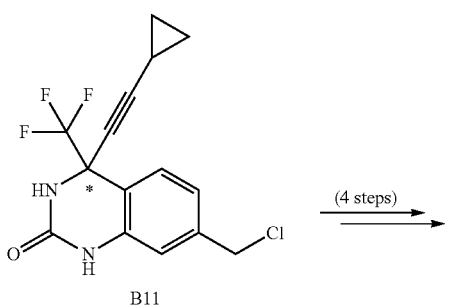

B11
(4 steps) →

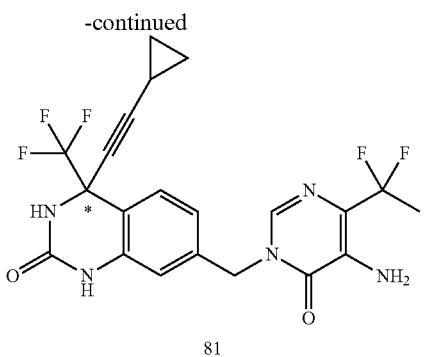

81

Step 1: (S)-7-((4-acetyl-5-fluoro-6-oxopyrimidin-1(6H)-yl)methyl)-4-(cyclopropylethynyl)-4-(trifluoromethyl)-3,4-dihydroquinazolin-2(1H)-one: To a solution of intermediate B11 (100 mg, 0.304 mmol), 6-acetyl-5-fluoropyrimidin-4(3H)-one (95 mg, 0.608 mmol) and $K_2CO_3$ (126 mg, 0.913 mmol) in DMF (2 mL) was stirred 25° C. for 16 h. The reaction mixture was diluted with water (15 mL), and then extracted with EtOAc (2×25 mL). The combined organic layer was washed with brine (3×10 mL), dried over $Na_2SO_4$, filtered and concentrated. The resulting residue was purified by prep-TLC ($SiO_2$, 50% EtOAc:PE) to give the title compound.

Step 2: (S)-7-((4-acetyl-5-((2,4-dimethoxybenzyl)amino)-6-oxopyrimidin-1(6H)-yl)methyl)-4-(cyclopropylethynyl)-4-(trifluoromethyl)-3,4-dihydroquinazolin-2(H)-one: To a solution of (S)-7-((4-acetyl-5-fluoro-6-oxopyrimidin-1(6H)-yl)methyl)-4-(cyclopropylethynyl)-4-(trifluoromethyl)-3,4-dihydroquinazolin-2(1H)-one (30 mg, 0.067 mmol) in DMF (1 mL) was added (2,4-dimethoxyphenyl)methanamine (33.6 mg, 0.201 mmol) and $K_2CO_3$ (18.49 mg, 0.134 mmol). The reaction was stirred at 50° C. for 2 h. The reaction mixture was diluted with water (5 mL), and then extracted with EtOAc (2×15 mL). The combined organic layer was washed with brine (3×10 mL), dried over $Na_2SO_4$, filtered and concentrated. The resulting residue was purified by prep-TLC ($SiO_2$, 50% EtOAc/PE) to give the title compound. MS (ESI) m/z 596.1 [M+1].

Step 3: (S)-7-((4-acetyl-5-amino-6-oxopyrimidin-1(6H)-yl)methyl)-4-(cyclopropylethynyl)-4-(trifluoromethyl)-3,4-dihydroquinazolin-2(1H)-one: A solution of (S)-7-((4-acetyl-5-((2,4-dimethoxybenzyl)amino)-6-oxopyrimidin-1(6H)-yl)methyl)-4-(cyclopropylethynyl)-4-(trifluoromethyl)-3,4-dihydroquinazolin-2(1H)-one (35 mg, 0.059 mmol) in DCM (1 mL) and TFA (0.3 mL) was stirred at 25° C. for 1 h. The reaction mixture was concentrated to give a crude product. The resulting residue was purified by prep-TLC ($SiO_2$, 50% EtOAc/PE) to give the title compound. MS (ESI) m/z 446.1 [M+1].

Step 4: (S)-7-((5-amino-4-(1,1-difluoroethyl)-6-oxopyrimidin-1(6H)-yl)methyl)-4-(cyclopropylethynyl)-4-(trifluoromethyl)-3,4-dihydroquinazolin-2(H)-one: To a solution of (S)-7-((4-acetyl-5-amino-6-oxopyrimidin-1(6H)-yl)methyl)-4-(cyclopropylethynyl)-4-(trifluoromethyl)-3,4-dihydroquinazolin-2(1H)-one (15 mg, 0.034 mmol) in DCM (1 mL) was added DAST (0.044 mL, 0.34 mmol) at 0° C. Then, the reaction was stirred at 25° C. for 5 h. The reaction mixture was diluted with water (5 mL), and then extracted with EtOAc (2×5 mL). The combined organic layer was washed with NaHCO₃ (5 mL) and brine (5 mL), dried over $Na_2SO_4$, filtered and concentrated. The residue was purified by prep-TLC ($SiO_2$, 50% EtOAc/PE) to give the title compound. ¹H NMR (400 MHz, MeOH-d₄) δ ppm 0.75 (td, J=4.4, 2.9 Hz, 2H), 0.85-0.90 (m, 2H), 1.37-1.44 (m, 1H), 1.94 (t, J=19.1 Hz, 3H), 5.16 (s, 2H), 6.77 (s, 1H), 7.02 (dd, J=8.16, 1.54 Hz, 1H), 7.51 (d, J=8.16 Hz, 1H), 7.85 (s, 1H). MS (ESI) m z 468.1 [M+1].

Example 82: (S)-4-(cyclopropylethynyl)-4-(1,1-difluoroethyl)-6-fluoro-7-((3-methoxy-6-oxopyridazin-1(6H)-yl)methyl)-3,4-dihydroquinazolin-2(1H)-one

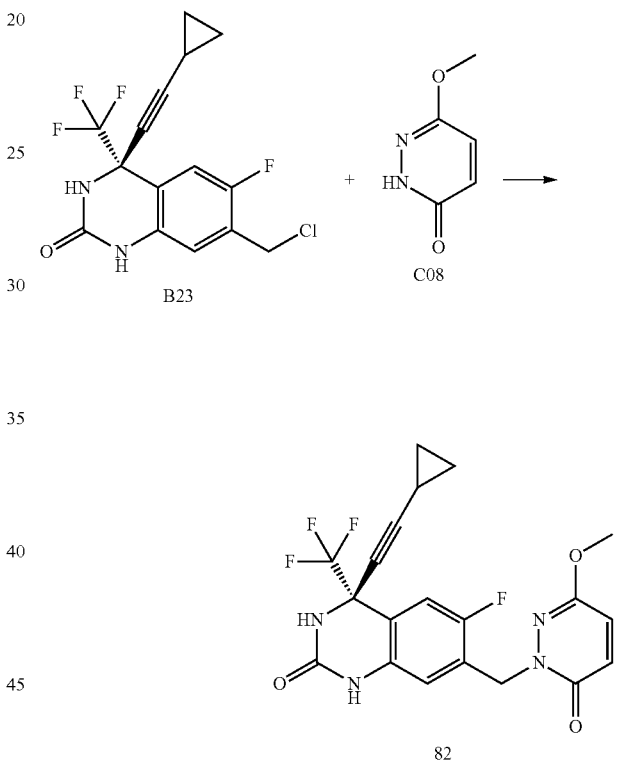

82

To a solution of intermediate B23 (30 mg, 0.088 mmol) in DMF (1 mL) was added $K_2CO_3$ (36.3 mg, 0.263 mmol) and intermediate C08 (11.04 mg, 0.088 mmol). The mixture was stirred at 40° C. for 3 h. The reaction mixture poured into water (40 mL) and extracted with EtOAc (30 mL×2). The combined organic layer was dried over $Na_2SO_4$, filtered and concentrated. The resulting crude was purified by prep-HPLC (water:MeCN with 0.1% TFA) to give the title product. ¹H NMR (400 MHz, ACETONITRILE-d₃) δ=7.63 (br s, 1H), 7.25-7.23 (d, J=10.3 Hz, 1H), 7.05-7.03 (d, J=9.9 Hz, 1H), 6.89-6.88 (d, J=9.8 Hz, 1H), 6.72-6.70 (d, J=6.3 Hz, 1H), 6.17 (br s, 1H), 5.15 (s, 2H), 3.77 (s, 3H), 1.66 (t, J=18.8 Hz, 3H), 1.37 (tt, J=5.0, 8.3 Hz, 1H), 0.91-0.81 (m, 2H), 0.75-0.67 (m, 2H). MS (ESI) m/z 433.3 [M+1].

Example 83: (S)-4-(cyclopropylethynyl)-4-(1,1-difluoroethyl)-6-fluoro-7-((4-methoxy-6-oxopyridazin-1(6H)-yl)methyl)-3,4-dihydroquinazolin-2(1H)-one Example 84: (S)-4-(cyclopropylethynyl)-4-(1,1-difluoroethyl)-6-fluoro-7-((4-methoxy-2-oxopyridin-1(2H)-yl)methyl)-3,4-dihydroquinazolin-2(1H)-one

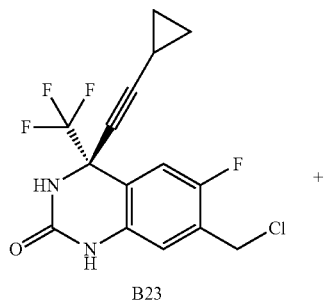

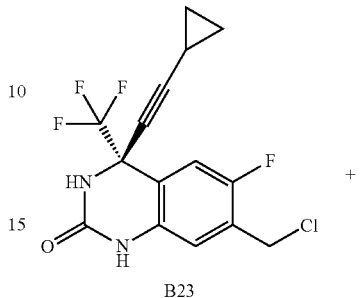

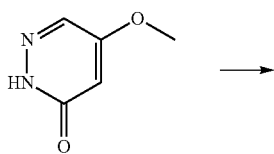

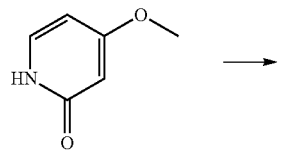

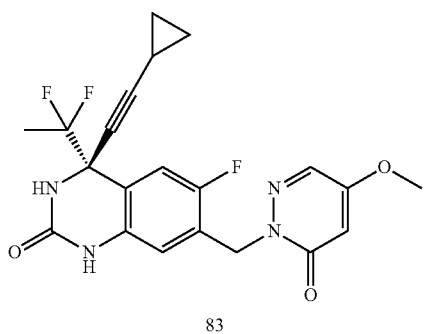

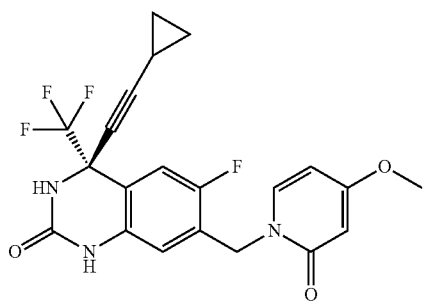

To a solution of intermediate B23 (30 mg, 0.088 mmol) in DMF (1 mL) was added K$_2$CO$_3$ (36.3 mg, 0.263 mmol) and 5-methoxypyridazin-3(2H)-one (11.04 mg, 0.088 mmol). The mixture was stirred at 40° C. for 3 h. The reaction mixture poured into water (40 mL) and extracted with EtOAc (30 mL×2). The combined organic layer was dried over Na$_2$SO$_4$, filtered and concentrated. The resulting crude was purified by prep-HPLC (water:MeCN with 0.1% TFA) to give the title product. $^1$H NMR (400 MHz, DMSO-d$_6$) δ=9.39 (s, 1H), 7.94 (s, 1H), 7.83-7.82 (d, J=2.9 Hz, 1H), 7.11-7.09 (d, J=10.1 Hz, 1H), 6.63-6.61 (d, J=6.5 Hz, 1H), 6.36-6.35 (d, J=2.9 Hz, 1H), 5.28-5.10 (m, 2H), 3.82 (s, 3H), 1.67 (t, J=18.8 Hz, 3H), 1.47-1.36 (m, 1H), 0.89-0.80 (m, 2H), 0.73-0.63 (m, 2H). MS (ESI) m/z 433.1 [M+1].

To a solution of intermediate B23 (40 mg, 0.117 mmol) in DMF (1.8 mL) was added K$_2$CO$_3$ (48.4 mg, 0.350 mmol) and 4-methoxypyridin-2(1H)-one (14.60 mg, 0.117 mmol). The mixture was stirred at 40° C. for 2 h. The reaction mixture was filtered and purified by prep-HPLC (water: MeCN with 0.1% TFA) to give the title product. $^1$H NMR (400 MHz, acetonitrile-d$_3$) δ=7.80 (br s, 1H), 7.42-7.44 (d, J=7.6 Hz, 1H), 7.24-7.26 (d, J=10.4 Hz, 1H), 6.68-6.70 (d, J=6.4 Hz, 1H), 6.18 (br s, 1H), 6.03-6.05 (dd, J=2.7, 7.6 Hz, 1H), 5.96-5.97 (d, J=2.7 Hz, 1H), 5.00-5.09 (m, 2H), 3.77 (s, 3H), 1.66 (t, J=18.8 Hz, 3H), 1.34-1.36 (m, 1H), 0.82-0.89 (m, 2H), 0.69-0.75 (m, 2H). MS (ESI) m/z 432.1 [M+1].

Example 85: (S)-7-((3-amino-5-methyl-2-oxopyrazin-1(2H)-yl)methyl)-4-(cyclopropylethynyl)-4-(1,1-difluoroethyl)-6-fluoro-3,4-dihydroquinazolin-2(1H)-one

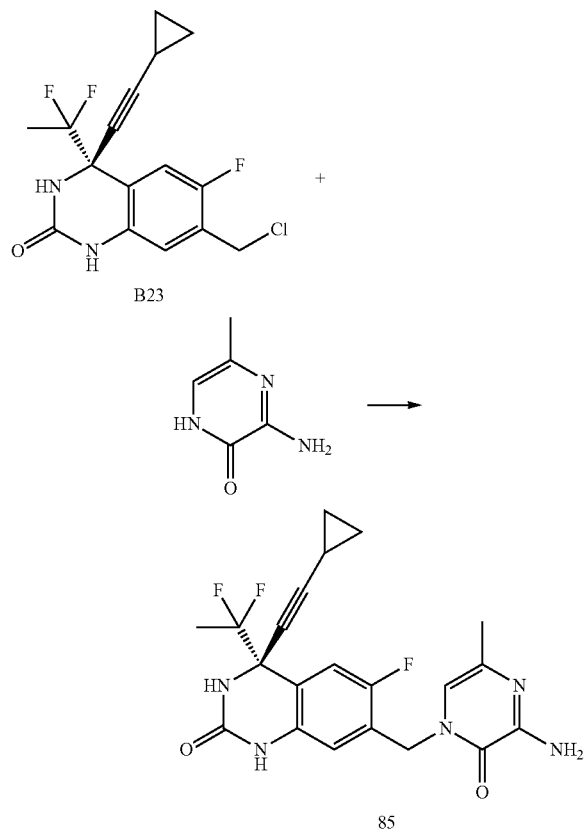

Step 1: tert-butyl (S)-(4-((4-(cyclopropylethynyl)-4-(1,1-difluoroethyl)-6-fluoro-2-oxo-1,2,3,4-tetrahydroquinazolin-7-yl)methyl)-6-methyl-3-oxo-3,4-dihydropyrazin-2-yl)carbamate: A mixture of intermediate B23 (30 mg, 0.088 mmol), tert-butyl (6-methyl-3-oxo-3,4-dihydropyrazin-2-yl)carbamate (40 mg, 0.142 mmol), LiBr (10 mg, 0.142 mmol) and $K_2CO_3$ (72.6 mg, 0.525 mmol) in DMF (2 ml) was stirred at 45° C. for 4 h. The mixture was filtered and purified by prep-HPLC (water:MeCN with 0.1% TFA) to give the title product.

Step 2: (S)-7-((3-amino-5-methyl-2-oxopyrazin-1(2H)-yl)methyl)-4-(cyclopropylethynyl)-4-(1,1-difluoroethyl)-6-fluoro-3,4-dihydroquinazolin-2(1H)-one: To a solution of tert-butyl (S)-(4-((4-(cyclopropylethynyl)-4-(1,1-difluoroethyl)-6-fluoro-2-oxo-1,2,3,4-tetrahydroquinazolin-7-yl)methyl)-6-methyl-3-oxo-3,4-dihydropyrazin-2-yl)carbamate (20 mg, 3.05 μmol) in DCM (1 ml) was added TFA (1 ml) at 25° C. The reaction was stirred at 25° C. for 1 h. The mixture was filtered and purified by prep-HPLC (water:MeCN with 0.1% TFA) to give the title product. $^1$H NMR (400 MHz, ACETONITRILE-d3) δ=7.72 (br s, 1H), 7.29-7.28 (d, J=10.1 Hz, 1H), 6.83-6.81 (d, J=6.2 Hz, 1H), 6.58 (s, 1H), 6.23 (s, 1H), 5.12-4.89 (m, 2H), 2.10 (s, 3H), 1.94-1.68 (t, J=18.8 Hz, 3H), 1.42-1.28 (m, 1H), 0.89-0.79 (m, 2H), 0.76-0.65 (m, 2H). MS (ESI) m/z 432.1 [M+1].

Determination of Cell Kill (HIV-TACK) Activity:

PBMCs derived from healthy donors were grown in complete media (RPMI 1640 with L-glutamine; 10% heat inactivated Fetal Bovine Serum; 100 U/mL Penicillin-Streptomycin) containing 5 μg/mL Phytohemagglutinin at about $2.5 \times 10^6$ cells/mL for 3 days at 5% $CO_2$, 37° C., and 90% humidity. On day 4, PHA stimulated cells were washed and resuspended at about $20 \times 10^6$ cells/mL in complete media with IL-2 (10 U/mL) with VSV-G pseudotyped HIV virus stock (VSV-G/pNLG1-P2A-ΔEnv—20 μg/mL p24) and incubated for 4 hours at 37° C., 5% $CO_2$ and 90% humidity. VSV-G/pNLG1-P2A-ΔEnv is a VSV-G pseudotyped virus derived from pNL43 with egfp inserted 5' of nef and eGFP expression driven off normal spliced RNA transcripts. Virus contained Vif truncated by 50 amino acids due to deletion of a single nucleotide causing a frameshift and does not express Nef due to a stop codon after gfp. HIV Env is not expressed due to a frameshift resulting in multiple stop codons. Infected cells were then washed with complete media plus 10 U/mL IL-2 3-times with centrifuging at 200×g for 3 minutes at 22° C. Cells were resuspended at $5 \times 10^6$ cells/mL in complete media plus 10 U/mL IL-2 and incubated overnight at 37° C., 5% $CO_2$ and 9000 humidity. For compound treatment infected PBMCs were diluted to $4 \times 10^5$ cells/mL with RPMI 1640 with L-glutamine, 50% Normal Human Serum (NHS), 100 U/mL Penicillin-Streptomycin plus IL-2 (10 U/mL) and 20,000 cells were transferred to each well in a 384-well poly-D-lysine coated compound plate containing compounds with final DMSO <0.5%. Compounds were tested with 10-point 3-fold titration. Plates were analyzed on an Acumen ex3 imager using the Blue Laser 488 nm and the number of GFP positive objects were collected with loss of GFP representing death of infected cells. Titration curves and $EC_{50}$ values were calculated using a four-parameter logistic fit. Results are shown in Table 2.

TABLE 2

| Ex. No. | $EC_{50}$ nM | Ex. No. | $EC_{50}$ nM | Ex. No. | EC50 nM | Ex. No. | EC50 nM | Ex. No. | EC50 nM |
|---|---|---|---|---|---|---|---|---|---|
| 1 | 22 | 21 | 181 | 41 | 60 | 61 | 38 | 81 | 166 |
| 2 | 15 | 22 | 288 | 42 | 52 | 62 | 41 | 82 | 66 |
| 3 | 26 | 23 | 250 | 43 | 50 | 63 | 145 | 83 | 51 |
| 4 | 16 | 24 | 210 | 44 | 47 | 64 | 93 | 84 | 30 |
| 5 | 35 | 25 | 194 | 45 | 50 | 65 | 45 | 85 | 14 |
| 6 | 38 | 26 | 226 | 46 | 101 | 66 | 188 | | |
| 7 | 44 | 27 | 190 | 47 | 135 | 67 | 12 | | |
| 8 | 46 | 28 | 171 | 48 | 12 | 68 | 71 | | |
| 9 | 30 | 29 | 161 | 49 | 96 | 69 | 29 | | |
| 10 | 31 | 30 | 152 | 50 | 32 | 70 | 93 | | |
| 11 | 33 | 31 | 146 | 51 | 54 | 71 | 41 | | |
| 12 | 33 | 32 | 141 | 52 | 69 | 72 | 193 | | |
| 13 | 46 | 33 | 126 | 53 | 18 | 73 | 275 | | |
| 14 | 31 | 34 | 117 | 54 | 284 | 74 | 263 | | |
| 15 | 65 | 35 | 101 | 55 | 96 | 75 | 221 | | |
| 16 | 38 | 36 | 101 | 56 | 35 | 76 | 42 | | |
| 17 | 17 | 37 | 89 | 57 | 127 | 77 | 87 | | |
| 18 | 15 | 38 | 87 | 58 | 41 | 78 | 38 | | |
| 19 | 14 | 39 | 72 | 59 | 78 | 79 | 230 | | |
| 20 | 47 | 40 | 65 | 60 | 156 | 80 | 57 | | |

What is claimed is:

1. A compound of Formula I:

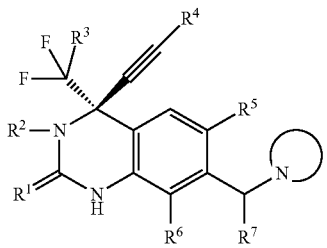

or a pharmaceutically acceptable salt thereof, wherein:
$R^1$ is O or S;
$R^2$ is —H or —$C_{1-8}$alkyl unsubstituted or substituted with 1 to 17 of F;
$R^3$ is halo or —$C_{1-8}$alkyl;
$R^4$ is —$C_{1-8}$alkyl or $C_{3-6}$cycloalkyl;
$R^5$ is —H, halo, —CN, —$C_{1-8}$alkyl, —$C_{2-8}$alkenyl, —C(O)O$C_{1-8}$alkyl, —C(O)$C_{1-8}$alkyl or —C(O)NR$^8$R$^9$;
$R^6$ is —H or halo;
$R^7$ is —H or halo;

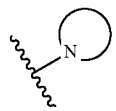

represents a 6-membered heterocyclic ring attached by a nitrogen atom in said ring to the carbon atom in —C(R$^7$)—, wherein the 6-membered heterocyclic ring is selected from pyridinone, pyrimidinone, pyrimidin-dione, pyrazinone, pyrazin-dione and pyridazinone, wherein each ring is unsubstituted or substituted with one or more substituents up to the maximum number allowed by valence, independently selected at each occurrence from:
(i) halo, (ii) —NR$^8$R$^9$, (iii) —CN,
(iv) —$C_{1-8}$alkyl unsubstituted or substituted with 1 to 8 substituents independently selected at each occurrence from —OH and halo,
(v) —$C_{1-4}$alkyl-O—$C_{1-4}$alkyl unsubstituted or substituted with 1 to 8 substituents independently selected at each occurrence from —OH or halo, and
(vi) —$C_{3-6}$cycloalkyl unsubstituted or substituted with 2 to 5 substituents independently selected at each occurrence from —OH or halo, and
(vii) —O$C_{1-8}$alkyl unsubstituted or substituted with 1 to 8 substituents independently selected at each occurrence from —OH and halo;
$R^8$ is —H or —$C_{1-8}$alkyl unsubstituted or substituted with 1 to 8 substituents independently selected at each occurrence from —OH and halo; and
$R^9$ is —H or —$C_{1-8}$alkyl unsubstituted or substituted with 1 to 8 substituents independently selected at each occurrence from —OH and halo.

2. The compound of claim 1 or a pharmaceutically acceptable salt thereof, wherein $R^2$ is —H or —$C_{1-6}$alkyl unsubstituted or substituted with 1 to 13 of F.

3. The compound of claim 2 or a pharmaceutically acceptable salt thereof, wherein $R^3$ is halo or —$C_{1-6}$alkyl.

4. The compound of claim 3 or a pharmaceutically acceptable salt thereof, wherein $R^4$ is —$C_{1-6}$alkyl or —$C_{3-6}$cycloalkyl.

5. The compound of claim 4 or a pharmaceutically acceptable salt thereof, wherein $R^5$ is —H, halo, —CN, —$C_{1-6}$alkyl, —$C_{2-6}$alkenyl, —C(O)O—$C_{1-6}$alkyl, —C(O)—$C_{1-6}$alkyl or —C(O)NR$^8$R$^9$.

6. The compound of claim 5 or a pharmaceutically acceptable salt thereof, wherein $R^6$ is —H, F, Cl or Br.

7. The compound of claim 6 or a pharmaceutically acceptable salt thereof, wherein $R^7$ is —H, F, Cl or Br.

8. The compound of claim 7 or a pharmaceutically acceptable salt thereof, wherein $R^8$ and $R^9$ are each independently selected from —H or —$C_{1-6}$alkyl unsubstituted or substituted with 1 to 6 substituents independently selected at each occurrence from —OH and halo.

9. The compound of claim 1 or a pharmaceutically acceptable salt thereof wherein $R^1$ is O.

10. The compound of claim 1 or a pharmaceutically acceptable salt thereof wherein $R^1$ is S.

11. The compound of claim 1 or a pharmaceutically acceptable salt thereof wherein $R^1$ is O; $R^2$ is —H or —$C_{1-6}$alkyl unsubstituted or substituted with 1 to 13 of —F; $R^3$ is halo or —$C_{1-6}$alkyl; $R^4$ is —$C_{1-6}$alkyl or —$C_{3-6}$cycloalkyl; $R^5$ is —H, halo, —CN, —$C_{1-6}$alkyl or —$C_{2-6}$alkenyl; $R^6$ is —H, F, Cl or Br; and $R^7$ is —H, F, Cl or Br.

12. The compound of claim 1 having Formula II

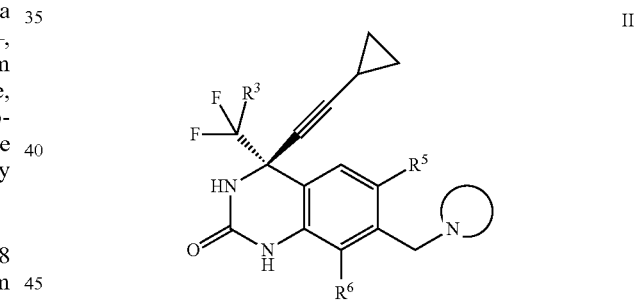

or a pharmaceutically acceptable salt thereof.

13. The compound of claim 12 or a pharmaceutically acceptable salt thereof, wherein $R^3$ is halo or —$C_{1-6}$alkyl.

14. The compound of claim 13 or a pharmaceutically acceptable salt thereof, wherein $R^5$ is —H, halo, —CN, —$C_{1-6}$alkyl or —$C_{2-6}$alkenyl.

15. The compound of claim 14 or a pharmaceutically acceptable salt thereof, wherein $R^6$ is —H, F, Cl or Br.

16. The compound of claim 1, or a pharmaceutically acceptable salt thereof, wherein:

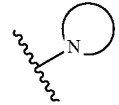

is selected from:

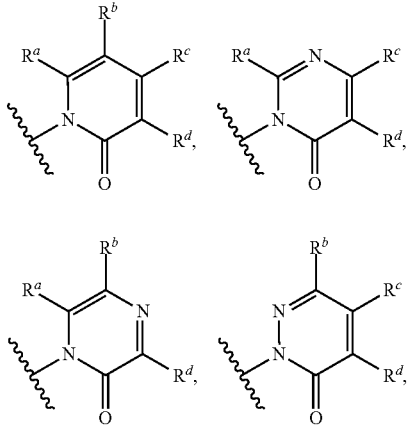

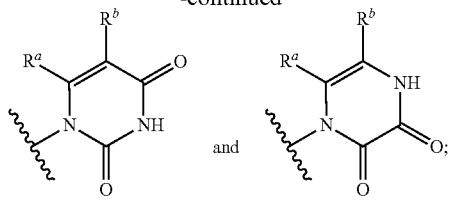

$R^a$ is —H or —$C_{1-6}$alkyl;
$R^b$ is (i) —H, (ii) halo, (iii) —$C_{1-6}$alkyl or (iv) —O$C_{1-6}$alkyl;
$R^c$ is (i) —H, (ii) halo, (iii) —$NR^8R^9$, (iv) —CN, (v) —$C_{1-6}$alkyl unsubstituted or substituted with —OH, (vi) —$C_{1-6}$alkyl substituted with 1 to 13 of F, (vii) —O$C_{1-6}$alkyl, (viii) —$C_{1-3}$alkyl-O—$C_{1-3}$alkyl, or (ix) —$C_{3-6}$cycloalkyl, (x) —C(O)O$R^8$, (xi) —CON$R^8R^9$ or (xii) —CO$R^8$; and
$R^d$ is (i) —H, (ii) —CN, (iii) halo, (iv) —$NR^8R^9$, (v) —$C_{1-6}$alkyl unsubstituted or substituted with —OH, or (vi) —O$C_{1-6}$alkyl.

17. The compound of claim 1 that is:

(S)-4-(cyclopropylethynyl)-6-fluoro-7-((6-oxopyrimidin-1(2H)-yl)methyl)-4-(trifluoromethyl)-3,4-dihydroquinazolin-2(1H)-one;
(S)-7-((3-amino-2-oxopyrazin-1(2H)-yl)methyl)-4-(cyclopropylethyny1)-6-fluoro-4-(trifluoromethyl)-3,4-dihydroquinazolin-2(1H)-one;
(S)-6-chloro-4-(cyclopropylethynyl)-7-((4-methyl-6-oxopyrimidin-1(2H)-yl)methyl)-4-(trifluoromethyl)-3,4-dihydroquinazolin-2(1H)-one;
(S)-4-(cyclopropylethynyl)-4-(1,1-difluoroethyl)-6-fluoro-7-((6-oxopyrimidin-1(2H)-yl)methyl)-3,4-dihydroquinazolin-2(1H)-one;
(S)-7-((5-amino-6-oxopyrimidin-1(6H)-yl)methyl)-4-(cyclopropylethyny1)-6-fluoro-4-(trifluoromethyl)-3,4-dihydroquinazolin-2(1H)-one;
(S)-4-(cyclopropylethynyl)-7-((4-(difluoromethyl)-6-oxopyrimidin-1(6H)-yl)methyl)-6-fluoro-4-(trifluoromethy1)-3,4-dihy droquinazolin-2( 1 H)-one ;
(S)-4-(cyclopropylethynyl)-6-fluoro-7-((4-(methoxymethyl)-6-oxopyrimidin-1(6H)-yl)methyl)-4-(trifluoromethyl)-3,4-dihydroquinazolin-2(1H)-one ;
(S)-7-((5-amino-4-chloro-6-oxopyrimidin-1(6H)-yl)methyl)-4-(cyclopropylethynyl)-6-fluoro-4-(trifluoromethyl)-3,4-dihydroquinazolin-2( 1 H)-one ;
(S)-7-((3-amino-2-oxopyrazin-1(2H)-yl)methyl)-4-(cyclopropylethyny1)-4-(trifluoromethyl)-3,4-dihydroquinazolin-2(1H)-one
(S)-7-((5-amino-6-oxopyrimidin-1(6H)-yl)methyl)-6-chloro-4-(cyclopropylethyny1)-4-(trifluoromethyl)-3,4-dihydroquinazolin-2(1H)-one ;
(S)-7-((5-amino-4-chloro-6-oxopyrimidin-1(6H)-yl)methyl)-6-chloro-4-(cyclopropylethynyl)-4-(trifluoromethy1)-3,4-dihydroquinazolin-2(1H)-one ;
(S)-6-chloro-7-((4-chloro-6-oxopyrimidin-1(6H)-yl)methyl)-4-(cyclopropylethyny1)-4-(trifluoromethyl)-3,4-dihydroquinazolin-2(1H)-one ;
(S)-7-((4-amino-6-oxopyrimidin-1(6H)-yl)methyl)-6-chloro-4-(cyclopropylethyny1)-4-(trifluoromethyl)-3,4-dihydroquinazolin-2(1H)-one ;
f59-6-bromo-4-(cyclopropylethynyl)-7-((6-oxopyrimidin-l(6J7)-yl)methyl)-4-(trifluoromethyl)-3,4-dihydroquinazolin-2(1H)-one ;
f59-4-(cyclopropylethynyl)-4-(1,l-difluoroethyl)-7-((4-(methoxymethyl)-6-oxopyrimidin-1(6H)-yl)methyl)-3,4-dihydroquinazolin-2(1H)-one ;
(S)-7-((3-amino-5-bromo-2-oxopyrazin-1(2H)-yl)methyl)-4-(cyclopropylethynyl)-6-fluoro-4-(trifluoromethyl)-3,4-dihydroquinazolin-2(1H)-one ;
(S)-7-((3-amino-2-oxopyrazin-1(2H)-yl)methyl)-6-chloro-4-(cyclopropylethynyl)-4-(1,1-difluoroethyl)-3,4-dihydroquinazolin-2(1H)-one;
(S)-6-chloro-4-(cyclopropylethynyl)-4-(1,1-difluoroethyl)-7-((4-methyl-6-oxopyrimidin-1(6H)-yl)methyl)-3,4-dihydroquinazolin-2(1H)-one ;
(S)-6-chloro-4-(cyclopropylethyny1)-4-(1,1-difluoroethyl)-7-((4-(methoxymethy1)-6-oxopyrimidin-1(6H)-yl)methyl)-3,4-dihydroquinazolin-2(1H)-one ;
(S)-7-((3-amino-2-oxopyrazin-1(2H)-yl)methyl)-4-(cyclopropylethyny1)-6,8-difluoro-4-(trifluoromethyl)-3,4-dihydroquinazolin-2(1H)-one ;
(S)-4-(cyclopropylethynyl)-7-((6-oxopyrimidin-1(6H)-yl)methyl)-4-(trifluoromethyl)-3,4-dihy droquinazolin-2( 1 H)-one;
(S)-7-((4-cyclopropyl-6-oxopyrimidin-1(6H)-yl)methyl)-4-(cyclopropylethyny1)-4-(trifluoromethyl)-3,4-dihydroquinazolin-2(1H)-one;
(S)-4-(cyclopropylethynyl)-7-((6-oxopyridazin-1(6H)-yl)methyl)-4-(trifluoromethy1)-3,4-dihy droquinazolin-2( 1 H)-one;
f59-7-((5-amino-6-oxopyridazin-l(6J7)-yl)methyl)-4-(cyclopropylethynyl)-4-(trifluoromethyl)-3,4-dihydroquinazolin-2(1H)-one;
(S)-4-(cyclopropylethynyl)-7-((6-oxo-4-(trifluoromethyl)pyrimidin-1(6H)-yl)methy1)-4-(trifluoromethyl)-3,4-dihydroquinazolin-2(1H)-one;
(S)-7-((5-amino-6-oxopyridazin-1(6H)-yl)methyl)-4-(cyclopropylethynyl)-6-fluoro-4-(trifluoromethyl)-3,4-dihydroquinazolin-2(1H)-one;
(S)-1-((4-(cyclopropylethynyl)-2-oxo-4-(trifluoromethyl)-1,2,3,4-tetrahydroquinazolin-7-yl)methyl)-6-oxo-1,6-dihydropyrimidine-4-carbonitrile;

(S)-7-((4-amino-6-oxopyrimidin-1(6H)-yl)methyl)-4-(cyclopropylethyny1)-4-(trifluoromethyl)-3,4-dihydroquinazolin-2(1H)-one;
f5J-7-((3-chloro-6-oxopyridazin-l(677)-yl)methyl)-4-(cyclopropylethynyl)-4-(trifluoromethyl)-3,4-dihydroquinazolin-2(1H)-one;
(S)-7-((3-amino-6-methyl-2-oxopyrazin-1(2H)-yl)methyl)-4-(cyclopropylethyny1)-4-(trifluoromethyl)-3,4-dihydroquinazolin-2(1H)-one;
(S)-4-(cyclopropylethynyl)-7-((4-(methoxymethyl)-6-oxopyrimidin-1(6H)-yl)methyl)-4-(trifluoromethyl)-3,4-dihydroquinazolin-2(1H)-one;
(S)-1-((4-(cyclopropylethynyl)-2-oxo-4-(trifluoromethyl)-1,2,3,4-tetrahydroquinazolin-7-yl)methyl)-6-oxo-1,6-dihydropyrimidin-4-aminium 2,2,2-trifluoroacetate;
(S)-7-((5-amino-6-oxo-4-(trifluoromethyl)pyrimidin-1(6H)-yl)methyl)-4-(cyclopropylethyny1)-4-(trifluoromethyl)-3,4-dihydroquinazolin-2(1H)-one;
(S)-4-(cyclopropylethynyl)-7-((4-methyl-6-oxopyrimidin-1(6H)-yl)methyl)-4-(trifluoromethyl)-3,4-dihydroquinazolin-2(1H)-one;
(S)-7-((4-chloro-6-oxopyrimidin-1(6H)-yl)methyl)-4-(cyclopropylethyny1)-4-(trifluoromethyl)-3,4-dihydroquinazolin-2(1H)-one;
(S)-4-(cyclopropylethynyl)-7-((4-(difluoromethyl)-6-oxopyrimidin-1(6H)-yl)methyl)-4-(trifluoromethyl)-3,4-dihydroquinazolin-2(1H)-one;
(S)-1-((4-(cyclopropylethynyl)-2-oxo-4-(trifluoromethyl)-1,2,3,4-tetrahydroquinazolin-7-yl)methyl)-6-oxo-l,6-dihydropyrimidin-5-aminium 2,2,2-trifluoroacetate;
(S)-4-(cyclopropylethynyl)-6-fluoro-7-((6-oxo-4-(trifluoromethyl)pyrimidin-1(6H)-yl)methyl)-4-(trifluoromethyl)-3,4-dihydroquinazolin-2(1H)-one;
(S)-7-((3-amino-2-oxopyridin-1(2H)-yl)methyl)-4-(cyclopropylethynyl)-6-fluoro-4-(trifluoromethyl)-3,4-dihydroquinazolin-2(777)-one;
(S)-7-((5-amino-4-chloro-6-oxopyrimidin-1(6H)-yl)methyl)-4-(cyclopropylethyny1)-4-(trifluoromethyl)-3,4-dihydroquinazolin-2(777)-one;
f59-7-((4-amino-6-oxopyrimidin-l(677)-yl)methyl)-4-(cyclopropylethynyl)-6-fluoro-4-(trifluoromethyl)-3,4-dihydroquinazolin-2(777)-one;
f5)-6-chloro-4-(cyclopropylethynyl)-7-((6-oxo-4-(trifluoromethyl)pyrimidin-l(677)-yl)methyl)-4-(trifluoromethyl)-3,4-dihydroquinazolin-2(777)-one;
f59-4-(cyclopropylethynyl)-6-fluoro-7-((4-methyl-6-oxopyrimidin-l(677)-yl)methyl)-4-(trifluoromethyl)-3,4-dihydroquinazolin-2(777)-one;
f59-7-((4-chloro-6-oxopyrimidin-l(677)-yl)methyl)-4-(cyclopropylethynyl)-6-fluoro-4-(trifluoromethyl)-3,4-dihydroquinazolin-2(777)-one;
(S)-7-((3-amino-2-oxopyrazin-1(2H)-yl)methyl)-6-bromo-4-(cyclopropylethyny1)-4-(trifluoromethyl)-3,4-dihydroquinazolin-2(1H)-one;
(S)-7-((3-amino-2-oxopyrazin-1(2H)-yl)methyl)-4-(cyclopropylethynyl)-3-methyl-4-(trifluoromethyl)-3,4-dihydroquinazolin-2(1H)-one;
(S)-1-((4-(cyclopropylethynyl)-2-oxo-4-(trifluoromethyl)-1,2,3,4-tetrahydroquinazolin-7-yl)methyl)-5-methylpyrimidine-2,4(1H,3H)-dione;
(S)-6-chloro-4-(cyclopropylethyny1)-4-(1,1-difluoroethyl)-7-((6-oxopyrimidin-1(6H)-yl)methyl)-3,4-dihydroquinazolin-2(1H)-one;
(S)-4-(cyclopropylethynyl)-6,8-difluoro-7-((6-oxopyrimidin-1(6H)-yl)methy1)-4-(trifluoromethyl)-3,4-dihydroquinazolin-2(1H)-one;
(S)-4-(cyclopropylethynyl)-4-(1,1-difluoroethyl)-6-fluoro-7-((6-oxopyridazin-1(6H)-yl)methyl)-3,4-dihydroquinazolin-2(1H)-one ;
(S)-4-(cyclopropylethynyl)-4-(1,1-difluoroethyl)-6-fluoro-7-((3-methyl-6-oxopyridazin-1(6H)-yl)methyl)-3,4-dihydroquinazolin-2(1H)-one ;
(S)-4-(cyclopropylethynyl)-4-(1,1-difluoroethyl)-6-fluoro-7-((3-methyl-6-oxopyridazin-1(6H)-yl)methyl)-3,4-dihydroquinazolin-2(1H)-one ;
(S)-7-((3-amino-2-oxopyrazin-1 (2H)-yl)methyl)-4-(cyclopropylethyny1)-4-( 1,1-difluoroethyl)-3,4-dihydroquinazolin-2(1H)-one ;
(S)-1-((4-(cyclopropylethynyl)-2-oxo-4-(trifluoromethyl)-1,2,3,4-tetrahydroquinazolin-7-yl)methyl)pyrimidine-2,4(1H,3H)-dione;
(S)- 4-(cyclopropylethynyl)-4-(1,1-difluoroethyl)-7-((6-oxopyrimidin-1(6H)-yl)methyl)-3,4-dihydroquinazolin-2(1H)-one ;
(S)-6-chloro-4-(cyclopropylethynyl)-7-((6-oxopyrimidin-1(6H)-yl)methyl)-4-(trifluoromethyl)-3,4-dihydroquinazolin-2(1H)-one;
(S)-5-amino-1-((4-(cyclopropylethynyl)-2-oxo-4-(trifluoromethyl)-1,2,3,4-tetrahydroquinazolin-7-yl)methyl)-6-oxo-l,6-dihydropyrimidine-4-carbonitrile;
(S)-7-((3-amino-2-oxopyrazin-1(2H)-yl)methyl)-6-chloro-4-(cyclopropylethynyl)-4-(trifluoromethyl)-3,4-dihydroquinazolin-2(1H)-one;
(S)-7-((3-amino-5-methyl-2-oxopyrazin-1(2H)-yl)methyl)-4-(cyclopropylethyny1)-4-(trifluoromethyl)-3,4-dihydroquinazolin-2(1H)-one;
(S)-7-((3-amino-5,6-dimethyl-2-oxopyrazin-1(2H)-yl)methyl)-4-(cyclopropylethyny1)-4-(trifluoromethyl)-3,4-dihydroquinazolin-2(1H)-one;
(S)- 6-chloro-4-(cyclopropylethynyl)-7-((4-(methoxymethyl)-6-oxopyrimidin-1(6H)-yl)methyl)-4-(trifluoromethyl)-3,4-dihydroquinazolin-2(1H)-one ;
(S)-6-chloro-4-(cyclopropylethyny1)-7-((4-(difluoromethyl)-6-oxopyrimidin-1(6H)-yl)methyl)-4-(trifluoromethyl)-3,4-dihydroquinazolin-2(1H)-one ;
(S)-4-(cyclopropylethynyl)-7-((4-(hydroxymethyl)-6-oxopyrimidin-1(6H)-yl)methy1-4-(trifluoromethyl)-3,4-dihydroquinazolin-2(1H)-one;
(S)-4-(cyclopropylethynyl)-4-(1,1-difluoroethyl)-7-((4-methyl-6-oxopyrimidin-1(6H)-yl)methyl)-3,4-dihydroquinazolin-2(1H)-one;
(S)-4-(cyclopropylethynyl)-6-fluoro-7-((4-(hydroxymethyl)-6-oxopyrimidin-1(6H)-yl)methyl)-4-(trifluoromethyl)-3,4-dihydroquinazolin-2(1H)-one ;
(S)-4-(cyclopropylethynyl)-6-fluoro-7-((5-(hydroxymethyl)-6-oxopyrimidin-1(6H)-yl)methyl)-4-(trifluoromethyl)-3,4-dihydroquinazolin-2(1H)-one;

-continued (S)-7-((3-amino-2-oxopyrazin-1 (2H)-yl)methyl)-4-(cyclopropylethynyl)-4-( 1,1-difluoroethyl)-6-fluoro-3,4-dihydroquinazolin-2(1H)-one;
(S)-7-((3-amino-5-chloro-2-oxopyrazin-1(2H)-yl)methyl)-4-(cyclopropylethynyl)-4-(trifluoromethyl)-3,4-dihydroquinazolin-2(1H)-one;
(S)-5-amino-1-((4-(cyclopropylethynyl)-6-fluoro-2-oxo-4-(trifluoromethyl)-1,2,3,4-tetrahydroquinazolin-7-yl)methyl)-6-oxo-1,6-dihydropyrimidine-4-carbonitrile;
(S)-3-((4-(cyclopropylethynyl)-2-thioxo-4-(trifluoromethyl)-1,2,3,4-tetrahydroquinazolin-7-yl)methyl)pyrimidin-4(3H)-one;
(S)-3 -amino-1 -((4-(cy cl opropylethynyl)-2-thioxo-4-(trifluorom ethyl)-1,2,3,4-tetrahydroquinazolin-7-yl)methyl)pyrazin-2(1H)-one;
f5)-7-((3-amino-2-oxo-4-(trifluoromethyl)pyridin-l(2J7)-yl)methyl)-4-(cyclopropylethynyl)-4-(trifluoromethyl)-3,4-dihydroquinazolin-2(7J7)-one;
(S)-4-(cyclopropylethynyl)-3-methyl-7-((6-oxopyrimidin-1(2H)-yl)methyl)-4-(trifluoromethyl)-3,4-dihydroquinazolin-2(1H)-one;
(S)-4-(cyclopropylethynyl)-3-ethyl-7-((6-oxopyrimidin-1(2H)-yl)methyl)-4-(trifluoromethyl)-3,4-dihydroquinazolin-2(1H)-one;
(S)-4-(cyclopropylethynyl)-6-methyl-7-((6-oxopyrimidin-1(2H)-yl)methyl)-4-(trifluoromethyl)-3,4-dihydroquinazolin-2(1H)-one;
(S)-7-((5-amino-4-(1,1-difluoroethyl)-6-oxopyrimidin-1(2H)-yl)methyl)-4-(cyclopropylethynyl)-4-(trifluoromethy1)-3,4-dihydroquinazolin-2(1H)-one;
(S)-4-(cyclopropylethyny1)-4-(1,1-difluoroethyl)-6-fluoro-7-((3-methoxy-6-oxopyridazin-1(6H)-yl)methyl)-3,4-dihydroquinazolin-2(1H)-one;
(S)-4-(cyclopropylethyny1)-4-(1,1-difluoroethyl)-6-fluoro-7-((4-methoxy-6-oxopyridazin-1(6H)-yl)methyl)-3,4-dihydroquinazolin-2(1H)-one;
(S)-4-(cyclopropylethyny1)-4-(1,1-difluoroethyl)-6-fluoro-7-((4-methoxy-2-oxopyridin-1(2H)-yl)methyl)-3,4-dihydroquinazolin-2(1H)-one;
(S)-7-((3-amino-5-methyl-2-oxopyrazin-1(2H)-yl)methyl)-4-(cyclopropylethynyl)-4-(1,1-difluoroethyl)-6-fluoro-3,4-dihydroquinazolin-2(1H)-one;

or a pharmaceutically acceptable salt thereof.

18. The compound of claim 1 that is:

4-(cyclopropylethynyl)-2-oxo-7-((6-oxopyrimidin-1(6H)-yl)methyl)-4-(trifluoromethyl)-1,2,3,4-tetrahydroquinazoline-6-carbonitrile, and the (S) and (R) stereoisomers thereof;
7-((3-amino-2-oxopyrazin-1(2H)-yl)methyl)-6-chloro-4-(cyclopropylethynyl)-3-methyl-4-(trifluoromethyl)-3,4-dihydroquinazolin-2(1H)-one, and the (S) and (R) stereoisomers thereof;
4-(3 -methylbut-1 -yn-1 -yl)-7-((6-oxopyrimidin-1 (6/7)-yl)methyl)-4-(trifluoromethyl)-3,4-dihydroquinazolin-2(1H)-one, and the (S) and (R) stereoisomers thereof;
6-chloro-4-(cyclopropylethynyl)-3-methyl-7-((6-oxopyrimidin-l(6/7)-yl)methyl)-4-(trifluoromethyl)-3,4-dihydroquinazolin-2(7J7)-one, and the (S) and (R) stereoisomers thereof; and
4-(4-methylpent-1-yn-1-yl)-7-((6-oxopyrimidin-1(6H)-yl)methyl)-4-(trifluoromethyl)-3,4-dihydroquinazolin-2(1H)-one, and the (S) and (R) stereoisomers thereof;

or a pharmaceutically acceptable salt thereof.

19. A pharmaceutical composition comprising an effective amount of the compound of claim 1, or a pharmaceutically acceptable salt thereof, and a pharmaceutically acceptable carrier.

20. The pharmaceutical composition of claim 19 further comprising an effective amount of one or more additional nucleoside or nucleotide HIV reverse transcriptase inhibitors, nucleoside or nucleotide reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

21. A method for the treatment or prophylaxis of infection by HIV, or for the treatment, prophylaxis or delay in the onset or progression of AIDS or ARC in a human subject in need thereof which comprises administering to the subject an effective amount of the compound according to claim 1, or a pharmaceutically acceptable salt thereof.

22. A method for eliciting GAG-POL dimerization in HIV-infected cells in a human subject in need thereof which comprises administering to the subject an effective amount of the compound according to claim 1, or a pharmaceutically acceptable salt thereof.

23. A method for selectively killing HIV infected GAG-POL expressing cells in a human subject which comprises administering to the subject an effective amount of the compound according to claim 1, or a pharmaceutically acceptable salt thereof.

24. A method for selectively killing HIV infected GAG-POL expressing cells without concomitant cytotoxicity to HIV naïve cells in a human subject which comprises administering to the human subject an effective amount of the compound according to claim 1, or a pharmaceutically acceptable salt thereof.

25. A method for augmenting the suppression of HIV viremia in a human subject whose viremia is being suppressed by administration of one or more compatible HIV antiviral agents, which comprises additionally administering to the subject an effective amount of the compound according to claim 1, or a pharmaceutically acceptable salt thereof.

26. The method of claim 21 further comprising administering to the human subject an effective amount of one or more additional compatible HIV antiviral agents selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

27. The method of claim 22 further comprising administering to the human subject an effective amount of one or more additional compatible HIV antiviral agents selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

28. The method of claim 23 further comprising administering to the human subject an effective amount of one or more additional compatible HIV antiviral agents selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

29. The method of claim 24 further comprising administering to the human subject an effective amount of one or more additional compatible HIV antiviral agents selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

30. The method of claim 25 further comprising administering to the human subject an effective amount of one or more additional compatible HIV antiviral agents selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

* * * * *